(12) United States Patent
    Connor

(10) Patent No.: US 12,629,032 B2
(45) Date of Patent: May 19, 2026

(54) WEARABLE RING OR BAND WITH CLOSE-FITTING SPECTROSCOPIC SENSORS

(71) Applicant: Robert A. Connor, Wyoming, MN (US)

(72) Inventor: Robert A. Connor, Wyoming, MN (US)

(73) Assignee: Medibotics LLC, Ham Lake, MN (US)

( * ) Notice: Subject to any disclaimer, the term of this patent is extended or adjusted under 35 U.S.C. 154(b) by 0 days.

(21) Appl. No.: 19/044,788

(22) Filed: Feb. 4, 2025

(65) Prior Publication Data

US 2025/0176834 A1     Jun. 5, 2025

Related U.S. Application Data

(63) Continuation-in-part of application No. 19/008,398, filed on Jan. 2, 2025, and a continuation-in-part of application No. 19/008,344, filed on Jan. 2, 2025, and a continuation-in-part of application No. 19/002,583, filed on Dec. 26, 2024, and a continuation-in-part of application No. 19/002,587, filed on Dec. 26, 2024, and a continuation-in-part of application No. 18/977,825, filed on Dec. 11, 2024, and a continuation-in-part of application No. 18/977,824, filed on Dec. 11, 2024, now Pat. No. 12,484,815, said application No. 18/977,825 is a continuation-in-part of application No. 18/929,026, filed on Oct. 28, 2024, application No. 19/044,788 is a continuation-in-part of application No. 18/885,728, filed on Sep. 15, 2024, said application No. 18/929,026 is a continuation-in-part of application No. 18/885,728, filed on Sep. 15, 2024, said application No.

18/977,825 is a continuation-in-part of application No. 18/885,728, filed on Sep. 15, 2024, application No. 19/044,788 is a continuation-in-part of application No. 18/775,128, filed on Jul. 17, 2024, now Pat. No. 12,405,211, said application No. 18/977,825 is a continuation-in-part of application No. 18/775,128, filed on Jul. 17, 2024, now Pat. No.

(Continued)

(51) Int. Cl.
    *A61B 5/00*          (2006.01)

(52) U.S. Cl.
    CPC .......... *A61B 5/0075* (2013.01); *A61B 5/6802* (2013.01)

(58) Field of Classification Search
    CPC ...... A61B 5/0075; A61B 5/6802; G06F 1/163
    See application file for complete search history.

(56)            References Cited

U.S. PATENT DOCUMENTS 8,961,415 B2     2/2015  LeBoeuf et al.
9,037,204 B2     5/2015  Schlottau
            (Continued)

*Primary Examiner* — Rockshana D Chowdhury
*Assistant Examiner* — Douglas R Burtner

(57)            ABSTRACT

A wearable ring or band can have spectroscopic sensors on its inner circumference. The ring or band can change: the angles at which light beams from sensors are transmitted; the radial locations of sensors around the inner circumference; and/or the distances between sensors and a person's body. The ring or band can also have an expandable and/or compressible chamber or layer on its inner circumference. The ring or band can also have a flexible, elastic, and/or articulated segment as part of its circumference.

1 Claim, 12 Drawing Sheets

Related U.S. Application Data 12,405,211, said application No. 18/929,026 is a continuation-in-part of application No. 18/775,128, filed on Jul. 17, 2024, now Pat. No. 12,405,211, said application No. 18/885,728 is a continuation-in-part of application No. 18/775,128, filed on Jul. 17, 2024, now Pat. No. 12,405,211, which is a continuation-in-part of application No. 18/617,950, filed on Mar. 27, 2024, said application No. 18/977,825 is a continuation-in-part of application No. 18/617,950, filed on Mar. 27, 2024, said application No. 18/885,728 is a continuation-in-part of application No. 18/617,950, filed on Mar. 27, 2024, and a continuation-in-part of application No. 18/121,841, filed on Mar. 15, 2023, now abandoned, said application No. 18/775,128 is a continuation-in-part of application No. 18/121,841, filed on Mar. 15, 2023, now abandoned, said application No. 18/617,950 is a continuation-in-part of application No. 18/121,841, filed on Mar. 15, 2023, now abandoned, said application No. 18/929,026 is a continuation-in-part of application No. 18/121,841, filed on Mar. 15, 2023, now abandoned, said application No. 18/977,825 is a continuation-in-part of application No. 18/121,841, filed on Mar. 15, 2023, now abandoned, which is a continuation-in-part of application No. 17/903,746, filed on Sep. 6, 2022, now abandoned, and a continuation-in-part of application No. 17/239,960, filed on Apr. 26, 2021, now abandoned, said application No. 17/903,746 is a continuation-in-part of application No. 17/239,960, filed on Apr. 26, 2021, now abandoned, and a continuation-in-part of application No. 16/737,052, filed on Jan. 8, 2020, now Pat. No. 11,754,542, said application No. 17/239,960 is a continuation-in-part of application No. 16/737,052, filed on Jan. 8, 2020, now Pat. No. 11,754,542, said application No. 18/121,841 is a continuation-in-part of application No. 16/737,052, filed on Jan. 8, 2020, now Pat. No. 11,754,542, which is a continuation-in-part of application No. 16/568,580, filed on Sep. 12, 2019, now Pat. No. 11,478,158, said application No. 17/903,746 is a continuation-in-part of application No. 16/568,580, filed on Sep. 12, 2019, now Pat. No. 11,478,158, said application No. 16/737,052 is a continuation-in-part of application No. 15/963,061, filed on Apr. 25, 2018, now Pat. No. 10,772,559, said application No. 16/568,580 is a continuation-in-part of application No. 15/963,061, filed on Apr. 25, 2018, now Pat. No. 10,772,559, and a continuation-in-part of application No. 15/944,746, filed on Apr. 3, 2018, now abandoned, said application No. 16/737,052 is a continuation-in-part of application No. 15/725,330, filed on Oct. 5, 2017, now Pat. No. 10,607,507, said application No. 16/568,580 is a continuation-in-part of application No. 15/725,330, filed on Oct. 5, 2017, now Pat. No. 10,607,507, said application No. 16/737,052 is a continuation-in-part of application No. 15/431,769, filed on Feb. 14, 2017, now abandoned, said application No. 15/725,330 is a continuation-in-part of application No. 15/431,769, filed on Feb. 14, 2017, now abandoned, which is a continuation-in-part of application No. 15/294,746, filed on Oct. 16, 2016, now Pat. No. 10,627,861, said application No. 16/737,052 is a continuation-in-part of application No. 15/294,746, filed on Oct. 16, 2016, now Pat. No.

10,627,861, said application No. 15/431,769 is a continuation-in-part of application No. 15/206,215, filed on Jul. 8, 2016, now abandoned, said application No. 15/963,061 is a continuation-in-part of application No. 14/992,073, filed on Jan. 11, 2016, now abandoned, said application No. 15/431,769 is a continuation-in-part of application No. 14/992,073, filed on Jan. 11, 2016, now abandoned, said application No. 15/206,215 is a continuation-in-part of application No. 14/951,475, filed on Nov. 24, 2015, now Pat. No. 10,314,492, said application No. 15/294,746 is a continuation-in-part of application No. 14/951,475, filed on Nov. 24, 2015, now Pat. No. 10,314,492, said application No. 15/725,330 is a continuation-in-part of application No. 14/951,475, filed on Nov. 24, 2015, now Pat. No. 10,314,492, said application No. 15/206,215 is a continuation-in-part of application No. 14/948,308, filed on Nov. 21, 2015, now abandoned, said application No. 14/992,073 is a continuation-in-part of application No. 14/562,719, filed on Dec. 7, 2014, now Pat. No. 10,130,277, said application No. 14/948,308 is a continuation-in-part of application No. 14/550,953, filed on Nov. 22, 2014, now abandoned, said application No. 15/963,061 is a continuation-in-part of application No. 14/550,953, filed on Nov. 22, 2014, now abandoned, said application No. 14/948,308 is a continuation-in-part of application No. 14/449,387, filed on Aug. 1, 2014, now abandoned, said application No. 15/431,769 is a continuation-in-part of application No. 14/330,649, filed on Jul. 14, 2014, now abandoned, said application No. 14/948,308 is a continuation-in-part of application No. 14/132,292, filed on Dec. 18, 2013, now Pat. No. 9,442,100, said application No. 14/951,475 is a continuation-in-part of application No. 14/071,112, filed on Nov. 4, 2013, now abandoned, and a continuation-in-part of application No. 13/901,131, filed on May 23, 2013, now Pat. No. 9,536,449, said application No. 14/948,308 is a continuation-in-part of application No. 13/901,099, filed on May 23, 2013, now Pat. No. 9,254,099, said application No. 14/992,073 is a continuation-in-part of application No. 13/616,238, filed on Sep. 14, 2012, now abandoned, said application No. 14/330,649 is a continuation-in-part of application No. 13/523,739, filed on Jun. 14, 2012, now Pat. No. 9,042,596.

(60) Provisional application No. 63/542,077, filed on Oct. 2, 2023, provisional application No. 63/279,773, filed on Nov. 16, 2021, provisional application No. 63/171,838, filed on Apr. 7, 2021, provisional application No. 62/930,013, filed on Nov. 4, 2019, provisional application No. 62/857,942, filed on Jun. 6, 2019, provisional application No. 62/814,692, filed on Mar. 6, 2019, provisional application No. 62/814,713, filed on Mar. 6, 2019, provisional application No. 62/800,478, filed on Feb. 2, 2019, provisional application No. 62/549,587, filed on Aug. 24, 2017, provisional application No. 62/439,147, filed on Dec. 26, 2016, provisional application No. 62/349,277, filed on Jun. 13, 2016, provisional application No. 62/311,462, filed on Mar. 22, 2016, provisional application No. 62/245,311, filed on Oct. 23, 2015, provisional application No. 61/932,517, filed on Jan. 28, 2014.

(56) References Cited

U.S. PATENT DOCUMENTS

| | | | |
|---|---|---|---|
| 9,061,899 B2 | 6/2015 | Rowe et al. | |
| 10,139,859 B2 | 11/2018 | von Badinski et al. | |
| 10,156,867 B2 | 12/2018 | von Badinski et al. | |
| 10,194,808 B1 * | 2/2019 | Thompson | A61B 5/02444 |
| 10,307,101 B1 * | 6/2019 | Miller | A61B 5/4875 |
| 10,607,507 B2 * | 3/2020 | Connor | A61B 5/4866 |
| 10,627,861 B2 * | 4/2020 | Connor | G06F 3/017 |
| 10,893,833 B2 | 1/2021 | Haverinen et al. | |
| 11,599,147 B2 | 3/2023 | von Badinski et al. | |
| 11,868,178 B2 | 1/2024 | von Badinski et al. | |
| 11,868,179 B2 | 1/2024 | von Badinski et al. | |
| 12,013,725 B2 | 6/2024 | von Badinski et al. | |
| 2006/0206018 A1 * | 9/2006 | Abul-Haj | A61B 5/1495 |
| | | | 600/316 |
| 2009/0018420 A1 | 1/2009 | White | |
| 2010/0249546 A1 | 9/2010 | White | |
| 2014/0249853 A1 * | 9/2014 | Proud | G16H 40/67 |
| | | | 705/3 |
| 2015/0015888 A1 | 1/2015 | Gulati et al. | |
| 2015/0094551 A1 | 4/2015 | Frix et al. | |
| 2015/0099943 A1 | 4/2015 | Russell | |
| 2015/0126824 A1 | 5/2015 | LeBoeuf et al. | |
| 2015/0148623 A1 | 5/2015 | Benaron | |
| 2015/0148624 A1 | 5/2015 | Benaron | |
| 2015/0216454 A1 | 8/2015 | Kasahara et al. | |
| 2015/0220109 A1 | 8/2015 | von Badinski et al. | |
| 2015/0238083 A1 | 8/2015 | Faubert et al. | |
| 2016/0235374 A1 * | 8/2016 | Miller | A61B 5/0075 |
| 2016/0246326 A1 | 8/2016 | von Badinski et al. | |
| 2016/0317060 A1 * | 11/2016 | Connor | A61B 5/4866 |
| 2017/0164878 A1 * | 6/2017 | Connor | A61B 5/14532 |
| 2017/0168591 A1 * | 6/2017 | Chung | E05B 37/00 |
| 2017/0235332 A1 | 8/2017 | von Badinski et al. | |
| 2018/0042513 A1 * | 2/2018 | Connor | A61B 5/369 |
| 2018/0115797 A1 * | 4/2018 | Wexler | H04N 1/32101 |
| 2018/0204375 A1 * | 7/2018 | Baek | G06F 3/012 |
| 2018/0220923 A1 * | 8/2018 | Shim | A61B 5/742 |
| 2020/0000345 A1 * | 1/2020 | Connor | A61B 5/14532 |
| 2020/0218312 A1 * | 7/2020 | Connor | G06F 1/1649 |
| 2021/0337885 A1 * | 11/2021 | Connor | A41C 3/0064 |
| 2021/0361233 A1 * | 11/2021 | Wilson | G06F 1/1637 |
| 2022/0225006 A1 * | 7/2022 | Allec | A61B 5/0059 |
| 2023/0113714 A1 | 4/2023 | Vallius et al. | |
| 2023/0190197 A1 | 6/2023 | Huttunen | |
| 2023/0277062 A1 * | 9/2023 | Dalvi | A61B 5/0075 |
| | | | 600/476 |
| 2024/0115204 A1 * | 4/2024 | Xu | A61B 5/0075 |
| 2024/0122548 A1 | 4/2024 | Kangas et al. | |
| 2024/0126329 A1 | 4/2024 | von Badinski et al. | |
| 2024/0143028 A1 | 5/2024 | von Badinski et al. | |
| 2024/0237904 A1 | 7/2024 | Makinen et al. | |
| 2024/0241541 A1 * | 7/2024 | Mäkinen | A61B 5/02416 |
| 2024/0293084 A1 | 9/2024 | Huttunen et al. | |
| 2024/0377316 A1 * | 11/2024 | Connor | G06V 20/20 |
| 2024/0410725 A1 | 12/2024 | Huopana | |
| 2025/0000218 A1 | 1/2025 | Lamsa et al. | |
| 2025/0000365 A1 * | 1/2025 | Connor | G06F 1/3278 |
| 2025/0009085 A1 | 1/2025 | Makinen | |
| 2025/0009086 A1 | 1/2025 | Makinen et al. | |
| 2025/0127439 A1 * | 4/2025 | Connor | A61B 5/14532 |
| 2025/0291382 A1 * | 9/2025 | Connor | A61B 5/0075 |

* cited by examiner

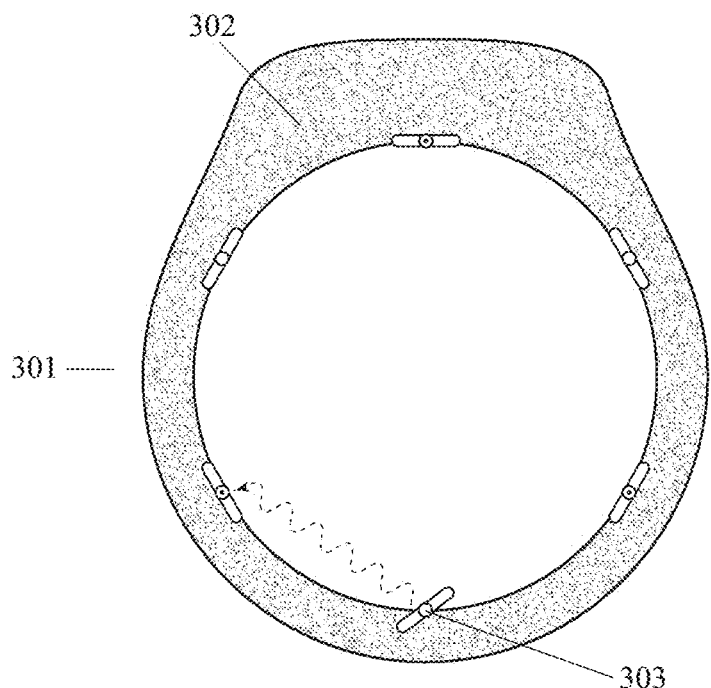
Fig. 3
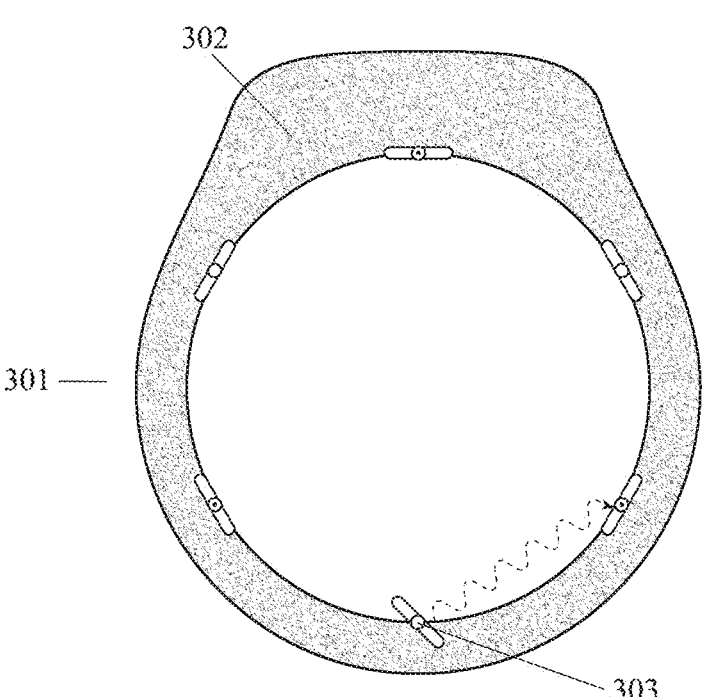

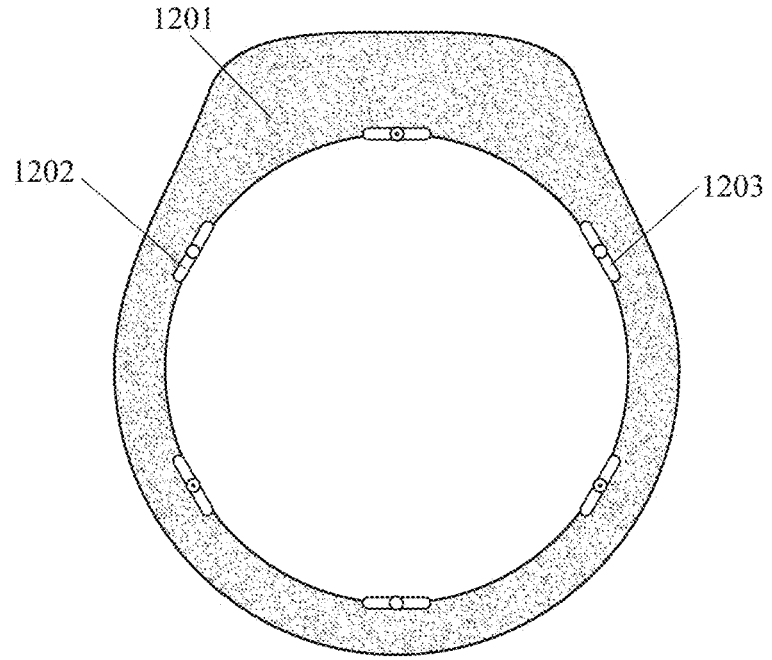
Fig. 12
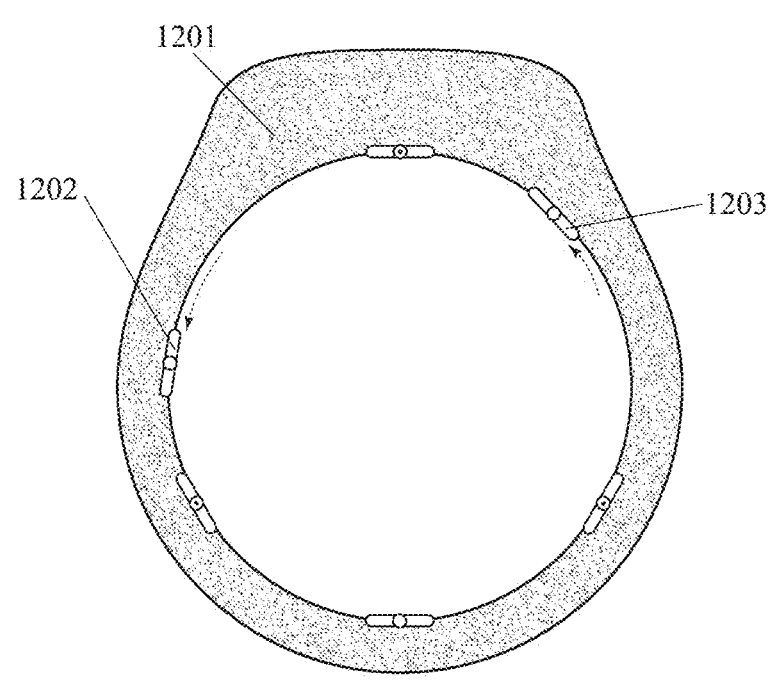

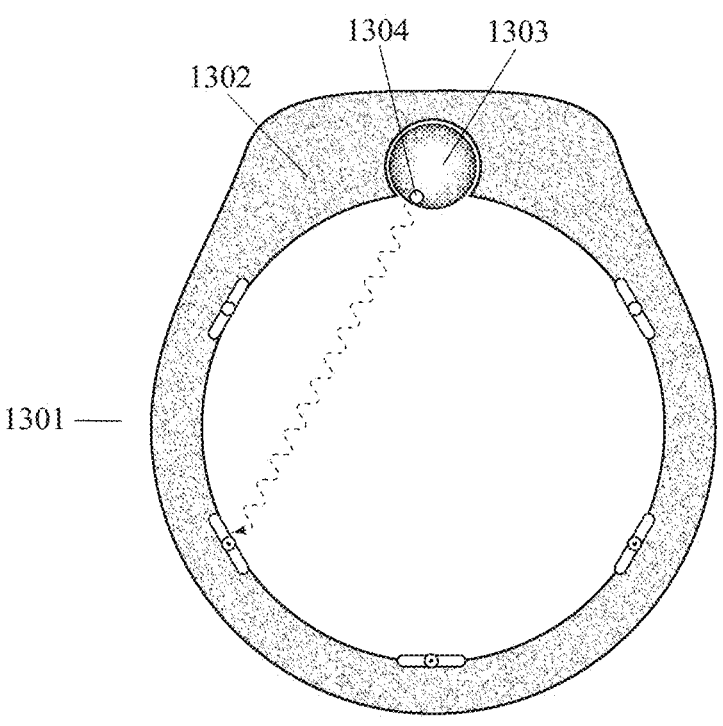
Fig. 13
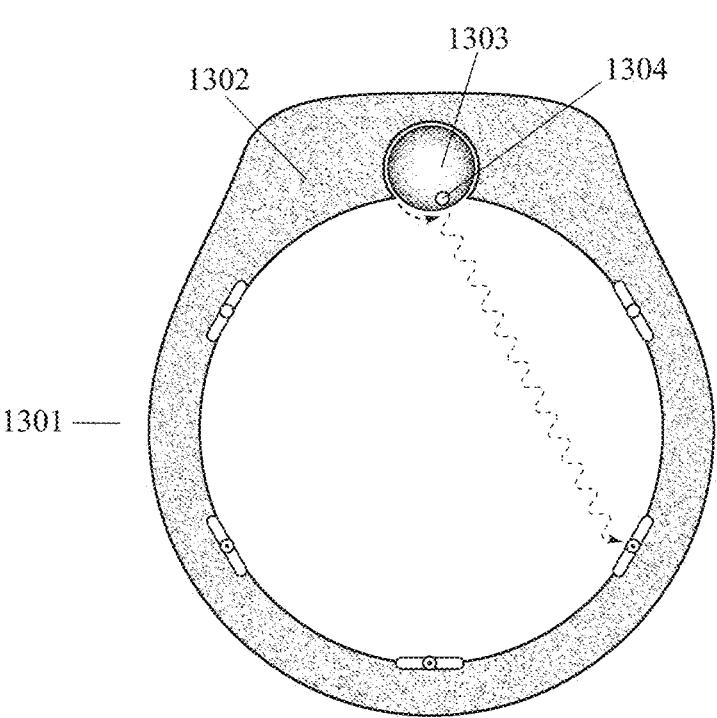

WEARABLE RING OR BAND WITH CLOSE-FITTING SPECTROSCOPIC SENSORS

CROSS-REFERENCE TO RELATED APPLICATIONS

This application is: a continuation in part of U.S. patent application Ser. No. 19/008,398 filed on 2025 Jan. 2; a continuation in part of U.S. patent application Ser. No. 19/008,344 filed on 2025 Jan. 2; a continuation in part of U.S. patent application Ser. No. 19/002,587 filed on 2024 Dec. 26; a continuation in part of U.S. patent application Ser. No. 19/002,583 filed on 2024 Dec. 26; a continuation in part of U.S. patent application Ser. No. 18/977,825 filed on 2024 Dec. 11; a continuation in part of U.S. patent application Ser. No. 18/977,824 filed on 2024 Dec. 11; a continuation in part of U.S. patent application Ser. No. 18/885,728 filed on 2024 Sep. 15; and a continuation in part of U.S. patent application Ser. No. 18/775,128 filed on 2024 Jul. 17.

U.S. patent application Ser. No. 19/008,398 was a continuation-in-part of U.S. patent application Ser. No. 19/008,344 filed on 2025 Jan. 2. U.S. patent application Ser. No. 19/008,398 was a continuation-in-part of U.S. patent application Ser. No. 19/002,587 filed on 2024 Dec. 26. U.S. patent application Ser. No. 19/008,398 was a continuation-in-part of U.S. patent application Ser. No. 19/002,583 filed on 2024 Dec. 26. U.S. patent application Ser. No. 19/008,398 was a continuation-in-part of U.S. patent application Ser. No. 18/977,825 filed on 2024 Dec. 11.

U.S. patent application Ser. No. 19/008,344 was a continuation-in-part of U.S. patent application Ser. No. 19/002,587 filed on 2024 Dec. 26. U.S. patent application Ser. No. 19/008,344 was a continuation-in-part of U.S. patent application Ser. No. 19/002,583 filed on 2024 Dec. 26. U.S. patent application Ser. No. 19/008,344 was a continuation-in-part of U.S. patent application Ser. No. 18/977,825 filed on 2024 Dec. 11. U.S. patent application Ser. No. 19/008,344 was a continuation-in-part of U.S. patent application Ser. No. 18/977,824 filed on 2024 Dec. 11.

U.S. patent application Ser. No. 18/977,825 was a continuation-in-part of U.S. patent application Ser. No. 18/929,026 filed on 2024 Oct. 28. U.S. patent application Ser. No. 18/977,825 was a continuation-in-part of U.S. patent application Ser. No. 18/885,728 filed on 2024 Sep. 15. U.S. patent application Ser. No. 18/977,825 was a continuation-in-part of U.S. patent application Ser. No. 18/775,128 filed on 2024 Jul. 17. U.S. patent application Ser. No. 18/977,825 was a continuation-in-part of U.S. patent application Ser. No. 18/617,950 filed on 2024 Mar. 27. U.S. patent application Ser. No. 18/977,825 was a continuation-in-part of U.S. patent application Ser. No. 18/121,841 filed on 2023 Mar. 15.

U.S. patent application Ser. No. 18/929,026 was a continuation-in-part of U.S. patent application Ser. No. 18/885,728 filed on 2024 Sep. 15. U.S. patent application Ser. No. 18/929,026 was a continuation-in-part of U.S. patent application Ser. No. 18/775,128 filed on 2024 Jul. 17. U.S. patent application Ser. No. 18/929,026 was a continuation-in-part of U.S. patent application Ser. No. 18/121,841 filed on 2023 Mar. 15. U.S. patent application Ser. No. 18/885,728 was a continuation-in-part of U.S. patent application Ser. No. 18/775,128 filed on 2024 Jul. 17. U.S. patent application Ser. No. 18/885,728 was a continuation-in-part of U.S. patent application Ser. No. 18/617,950 filed on 2024 Mar. 27. U.S. patent application Ser. No. 18/885,728 claimed the priority benefit of U.S. provisional application 63/542,077 filed on 2023 Oct. 2. U.S. patent application Ser. No. 18/885,728 was a continuation-in-part of U.S. patent application Ser. No. 18/121,841 filed on 2023 Mar. 15.

U.S. patent application Ser. No. 18/775,128 was a continuation-in-part of U.S. patent application Ser. No. 18/617,950 filed on 2024 Mar. 27. U.S. patent application Ser. No. 18/775,128 was a continuation-in-part of U.S. patent application Ser. No. 18/121,841 filed on 2023 Mar. 15. U.S. patent application Ser. No. 18/617,950 claimed the priority benefit of U.S. provisional application 63/542,077 filed on 2023 Oct. 2. U.S. patent application Ser. No. 18/617,950 was a continuation-in-part of U.S. patent application Ser. No. 18/121,841 filed on 2023 Mar. 15. U.S. patent application Ser. No. 18/121,841 was a continuation-in-part of U.S. patent application Ser. No. 17/903,746 filed on 2022 Sep. 6. U.S. patent application Ser. No. 18/121,841 was a continuation-in-part of U.S. patent application Ser. No. 17/239,960 filed on 2021 Apr. 26. U.S. patent application Ser. No. 18/121,841 was a continuation-in-part of U.S. patent application Ser. No. 16/737,052 filed on 2020 Jan. 8.

U.S. patent application Ser. No. 17/903,746 was a continuation-in-part of U.S. patent application Ser. No. 16/568,580 filed on 2019 Sep. 12. U.S. patent application Ser. No. 17/903,746 was a continuation-in-part of U.S. patent application Ser. No. 16/737,052 filed on 2020 Jan. 8. U.S. patent application Ser. No. 17/903,746 was a continuation-in-part of U.S. patent application Ser. No. 17/239,960 filed on 2021 Apr. 26. U.S. patent application Ser. No. 17/903,746 claimed the priority benefit of U.S. provisional application 63/279,773 filed on 2021 Nov. 16. U.S. patent application Ser. No. 17/239,960 claimed the priority benefit of U.S. provisional application 63/171,838 filed on 2021 Apr. 7. U.S. patent application Ser. No. 17/239,960 was a continuation-in-part of U.S. patent application Ser. No. 16/737,052 filed on 2020 Jan. 8.

U.S. patent application Ser. No. 16/737,052 claimed the priority benefit of U.S. provisional application 62/930,013 filed on 2019 Nov. 4. U.S. patent application Ser. No. 16/737,052 claimed the priority benefit of U.S. provisional application 62/857,942 filed on 2019 Jun. 6. U.S. patent application Ser. No. 16/737,052 claimed the priority benefit of U.S. provisional application 62/814,713 filed on 2019 Mar. 6. U.S. patent application Ser. No. 16/737,052 claimed the priority benefit of U.S. provisional application 62/814,692 filed on 2019 Mar. 6. U.S. patent application Ser. No. 16/737,052 claimed the priority benefit of U.S. provisional application 62/800,478 filed on 2019 Feb. 2. U.S. patent application Ser. No. 16/737,052 was a continuation-in-part of U.S. patent application Ser. No. 16/568,580 filed on 2019 Sep. 12. U.S. patent application Ser. No. 16/737,052 was a continuation-in-part of U.S. patent application Ser. No. 15/963,061 filed on 2018 Apr. 25 which issued as U.S. Pat. No. 10,772,559 on 2020 Sep. 15. U.S. patent application Ser. No. 16/737,052 was a continuation-in-part of U.S. patent application Ser. No. 15/725,330 filed on 2017 Oct. 5 which issued as U.S. Ser. No. 10,607,507 on 2020 Mar. 31. U.S. patent application Ser. No. 16/737,052 was a continuation-in-part of U.S. patent application Ser. No. 15/431,769 filed on 2017 Feb. 14. U.S. patent application Ser. No. 16/737,052 was a continuation-in-part of U.S. patent application Ser. No. 15/294,746 filed on 2016 Oct. 16 which issued as U.S. Pat. No. 10,627,861 on 2020 Apr. 21.

U.S. patent application Ser. No. 16/568,580 claimed the priority benefit of U.S. provisional application 62/857,942 filed on 2019 Jun. 6. U.S. patent application Ser. No. 16/568,580 claimed the priority benefit of U.S. provisional application 62/814,713 filed on 2019 Mar. 6. U.S. patent application Ser. No. 16/568,580 claimed the priority benefit of U.S. provisional application 62/814,692 filed on 2019 Mar. 6. U.S. patent application Ser. No. 16/568,580 was a continuation-in-part of U.S. patent application Ser. No. 15/963,061 filed on 2018 Apr. 25 which issued as U.S. Pat. No. 10,772,559 on 2020 Sep. 15. U.S. patent application Ser. No. 16/568,580 was a continuation-in-part of U.S. patent application Ser. No. 15/725,330 filed on 2017 Oct. 5 which issued as U.S. Pat. No. 10,607,507 on 2020 Mar. 31. U.S. patent application Ser. No. 16/568,580 was a continuation-in-part of U.S. patent application Ser. No. 15/431,769 filed on 2017 Feb. 14. U.S. patent application Ser. No. 16/568,580 was a continuation-in-part of U.S. patent application Ser. No. 15/418,620 filed on 2017 Jan. 27. U.S. patent application Ser. No. 16/568,580 was a continuation-in-part of U.S. patent application Ser. No. 15/294,746 filed on 2016 Oct. 16 which issued as U.S. Pat. No. 10,627,861 on 2020 Apr. 21.

U.S. patent application Ser. No. 15/963,061 was a continuation-in-part of U.S. patent application Ser. No. 14/992,073 filed on 2016 Jan. 11. U.S. patent application Ser. No. 15/963,061 was a continuation-in-part of U.S. patent application Ser. No. 14/550,953 filed on 2014 Nov. 22. U.S. patent application Ser. No. 15/725,330 claimed the priority benefit of U.S. provisional application 62/549,587 filed on 2017 Aug. 24. U.S. patent application Ser. No. 15/725,330 claimed the priority benefit of U.S. provisional application 62/439,147 filed on 2016 Dec. 26. U.S. patent application Ser. No. 15/725,330 was a continuation-in-part of U.S. patent application Ser. No. 15/431,769 filed on 2017 Feb. 14. U.S. patent application Ser. No. 15/725,330 was a continuation-in-part of U.S. patent application Ser. No. 14/951,475 filed on 2015 Nov. 24 which issued as U.S. Pat. No. 10,314,492 on 2019 Jun. 11.

U.S. patent application Ser. No. 15/431,769 claimed the priority benefit of U.S. provisional application 62/439,147 filed on 2016 Dec. 26. U.S. patent application Ser. No. 15/431,769 claimed the priority benefit of U.S. provisional application 62/349,277 filed on 2016 Jun. 13. U.S. patent application Ser. No. 15/431,769 claimed the priority benefit of U.S. provisional application 62/311,462 filed on 2016 Mar. 22. U.S. patent application Ser. No. 15/431,769 was a continuation-in-part of U.S. patent application Ser. No. 15/294,746 filed on 2016 Oct. 16 which issued as U.S. Pat. No. 10,627,861 on 2020 Apr. 21. U.S. patent application Ser. No. 15/431,769 was a continuation-in-part of U.S. patent application Ser. No. 15/206,215 filed on 2016 Jul. 8. U.S. patent application Ser. No. 15/431,769 was a continuation-in-part of U.S. patent application Ser. No. 14/992,073 filed on 2016 Jan. 11. U.S. patent application Ser. No. 15/431,769 was a continuation-in-part of U.S. patent application Ser. No. 14/330,649 filed on 2014 Jul. 14.

U.S. patent application Ser. No. 15/418,620 claimed the priority benefit of U.S. provisional application 62/297,827 filed on 2016 Feb. 20. U.S. patent application Ser. No. 15/418,620 was a continuation-in-part of U.S. patent application Ser. No. 14/951,475 filed on 2015 Nov. 24 which issued as U.S. patent Ser. No. 10/314,492 on 2019 Jun. 11. U.S. patent application Ser. No. 15/294,746 claimed the priority benefit of U.S. provisional application 62/349,277 filed on 2016 Jun. 13. U.S. patent application Ser. No. 15/294,746 claimed the priority benefit of U.S. provisional application 62/245,311 filed on 2015 Oct. 23. U.S. patent application Ser. No. 15/294,746 was a continuation-in-part of U.S. patent application Ser. No. 14/951,475 filed on 2015 Nov. 24 which issued as U.S. Pat. No. 10,314,492 on 2019 Jun. 11.

U.S. patent application Ser. No. 15/206,215 claimed the priority benefit of U.S. provisional application 62/349,277 filed on 2016 Jun. 13. U.S. patent application Ser. No. 15/206,215 was a continuation-in-part of U.S. patent application Ser. No. 14/951,475 filed on 2015 Nov. 24 which issued as U.S. patent Ser. No. 10/314,492 on 2019 Jun. 11. U.S. patent application Ser. No. 15/206,215 was a continuation-in-part of U.S. patent application Ser. No. 14/948,308 filed on 2015 Nov. 21. U.S. patent application Ser. No. 14/992,073 was a continuation-in-part of U.S. patent application Ser. No. 14/562,719 filed on 2014 Dec. 7 which issued as U.S. Pat. No. 10,130,277 on 2018 Nov. 20. U.S. patent application Ser. No. 14/992,073 was a continuation-in-part of U.S. patent application Ser. No. 13/616,238 filed on 2012 Sep. 14.

U.S. patent application Ser. No. 14/951,475 was a continuation-in-part of U.S. patent application Ser. No. 14/071,112 filed on 2013 Nov. 4. U.S. patent application Ser. No. 14/951,475 was a continuation-in-part of U.S. patent application Ser. No. 13/901,131 filed on 2013 May 23 which issued as U.S. Pat. No. 9,536,449 on 2017 Jan. 3. U.S. patent application Ser. No. 14/948,308 was a continuation-in-part of U.S. patent application Ser. No. 14/550,953 filed on 2014 Nov. 22. U.S. patent application Ser. No. 14/948,308 was a continuation-in-part of U.S. patent application Ser. No. 14/449,387 filed on 2014 Aug. 1. U.S. patent application Ser. No. 14/948,308 was a continuation-in-part of U.S. patent application Ser. No. 14/132,292 filed on 2013 Dec. 18 which issued as U.S. Pat. No. 9,442,100 on 2016 Sep. 13. U.S. patent application Ser. No. 14/948,308 was a continuation-in-part of U.S. patent application Ser. No. 13/901,099 filed on 2013 May 23 which issued as U.S. Pat. No. 9,254,099 on 2016 Feb. 9. U.S. patent application Ser. No. 14/562,719 claimed the priority benefit of U.S. provisional application 61/932,517 filed on 2014 Jan. 28. U.S. patent application Ser. No. 14/330,649 was a continuation-in-part of U.S. patent application Ser. No. 13/523,739 filed on 2012 Jun. 14 which issued as U.S. Pat. No. 9,042,596 on 2015 May 26.

The entire contents of these applications are incorporated herein by reference.

FEDERALLY SPONSORED RESEARCH

Not Applicable

SEQUENCE LISTING OR PROGRAM

Not Applicable

BACKGROUND

Field of Invention

This invention relates to wearable devices for measuring biometric parameters.

INTRODUCTION

Biometric wearable devices such as smart finger rings and smart watches with optical sensors have advantages over mobile handheld devices (such as cellphones) and non-mobile devices (such as stationary medical equipment) for monitoring a person's biometric parameters: to diagnosis adverse health conditions; to provide an alert in case of an adverse health event; to provide a feedback and/or control loop for the operation of implanted medical devices; and to help people maintain their health and prevent illness. Due to their consistent proximity to a person's body and their easily transportable nature, these devices can monitor biometric parameters more broadly and consistently than handheld devices. There are also challenges in the development of biometric wearable devices. For example, they are relatively small, which can make it difficult for them to house complex components. Also, they can shift or rotate on a person's finger, wrist, or arm. However, these challenges are not insurmountable and are addressed by some of the innovative designs disclosed herein.

REVIEW OF THE RELEVANT ART

U.S. patent application 20150148623 (Benaron, May 28, 2015, "Hydration Monitoring Sensor and Method for Cell Phones, Smart Watches, Occupancy Sensors, and Wearables") discloses a sensor for hydration monitoring in and other devices that uses an optional phosphor-coated broadband white LED. U.S. patent application 20150148624 (Benaron, May 28, 2015, "Method for Detecting Physiology at Distance or During Movement for Mobile Devices, Illumination, Security, Occupancy Sensors, and Wearables") discloses a sensor for physiology monitoring in wearables and other devices that uses broadband light transmitted to an ear, face, or wrist.

U.S. patent application 20150238083 (Faubert et al., Aug. 27, 2015, "Method and System for Optically Investigating a Tissue of a Subject") discloses a probe device for optically investigating a person's body tissue comprising: a first probe element, a second probe element, and a third probe element each to be positioned at a respective vertex of a triangle for sensing the tissue. U.S. patent application 20150094551 (Frix et al., Apr. 2, 2015, "Continuous Transdermal Monitoring System and Method") discloses methods and systems for continuous transdermal monitoring via detecting light reflected by body tissue. U.S. patent application 20150015888 (Gulati et al., Jan. 15, 2015, "Dynamic Radially Controlled Light Input to a Noninvasive Analyzer Apparatus and Method of Use Thereof") discloses an analyzer apparatus and method to dynamically irradiate a sample with incident light, wherein the incident light is varied in time in terms of any of: position, radial position relative to a point of the skin of a subject, solid angle, incident angle, depth of focus, energy, and/or intensity.

U.S. Pat. No. 10,893,833 (Haverinen et al., Jan. 19, 2021, "Wearable Electronic Device and Method for Manufacturing Thereof") discloses a wearable electronic device with a body part made from non-ceramic material, having an inner surface and an outer surface, wherein at least one cavity having a depth is arranged on the inner surface of the body part. U.S. patent application 20240410725 (Huopana, Dec. 12, 2024, "Device for Measurements for a Wearable Device Sensor") discloses a device comprising: a support configured to receive an appendage of a human body; at least one light source; at least one light detector; and an actuator configured to move the at least one light source, or the at least one light detector, or both to at least two different measurement positions in relation to the support.

U.S. patent application 20230190197 (Huttunen, Jun. 22, 2023, "Adjustable Sensor in Wearable Device") discloses a wearable device with a sensor adjustment mechanism which moves the sensor with respect to a contact surface. U.S. patent application 20240293084 (Huttunen et al., Sep. 5, 2024, "Flexible Wearable Ring Device") discloses a wearable device constructed from elastically deformable flexible materials. U.S. patent application 20240122548 (Kangas et al., Apr. 18, 2024, "Techniques for Adaptive Sensors of a Wearable Device") discloses methods, systems, and devices for adaptive sensors which acquire physiological data from a user via multiple optical channels. U.S. patent application 20150216454 (Kasahara et al., Aug. 6, 2015, "Biological Information Measurement Apparatus and Biological Information Measurement Method") discloses a blood glucose level measurement apparatus which can be mounted on a person's wrist and performs measurement using light.

U.S. patent application 20250000218 (Lamsa et al., Jan. 2, 2025, "Wearable Ring Device with Deformable Inner Cover") discloses a wearable ring device with a housing with one or more sensors which acquire physiological data from a user and a deformable material extending along one or more portions of an inner circumferential surface of the housing. U.S. Pat. No. 8,961,415 (LeBoeuf et al., Feb. 24, 2015, "Methods and Apparatus for Assessing Physiological Conditions") discloses a monitoring apparatus and methods for assessing a physiological condition of a subject via a portable monitoring device associated with the subject. U.S. patent application 20150126824 (LeBoeuf et al., May 7, 2015, "Apparatus for Assessing Physiological Conditions") discloses a monitoring apparatus and methods for assessing assessment of a physiological condition of a subject using at least two types of physiological information.

U.S. patent applications 20250009085 (Makinen, Jan. 9, 2025, "C-Ring Form Factor for Wearable Ring Device with Adjustable Size") and 20250009086 (Makinen et al., Jan. 9, 2025, "Adaptive Rigid and Conformable Wearable Ring Device with Adjustable Circumference") disclose a wearable ring device which transitions between multiple discrete ring sizes. U.S. patent application 20240237904 (Makinen et al., Jul. 18, 2024, "Techniques for Measurement Path Multiplexing for a Wearable Device") discloses methods, systems, and devices for measurement multiplexing for a wearable device. U.S. Pat. No. 9,061,899 (Rowe et al., Jun. 23, 2015, "Apparatus and Method of Biometric Determination Using Specialized Optical Spectroscopy Systems") discloses methods and apparatuses for performing biometric determinations via optical spectroscopy using light sources such as light emitting diodes, laser diodes, vertical cavity surface emitting lasers, and broadband sources with multiple narrow-band optical filters.

U.S. patent application 20150099943 (Russell, Apr. 9, 2015, "Wearable Physiological Sensing Device with Optical Pathways") discloses a wearable physiological sensing device with at least one light source, a first light pipe coupled with the at least one light source, the first light pipe at least partially circumscribing an extremity of a patient, and including at least one aperture for radiating light from the light source into the extremity. U.S. Pat. No. 9,037,204 (Schlottau, May 19, 2015, "Filtered Detector Array for Optical Patient Sensors") discloses optical patient monitoring systems which emit two or more wavelengths of light into the tissue of a patient. U.S. patent application 20230113714 (Vallius et al., Apr. 13, 2023, "Configurable Photoplethysmogram System") discloses wearable devices for optical signal measurement which activate a combination of optical sensors positioned under a protrusion on an inner surface of the device.

U.S. patent application 20150220109 (von Badinski et al., Aug. 6, 2015, "Wearable Computing Device"), U.S. patent application 20160246326 (von Badinski et al., Aug. 25, 2016, "Wearable Computing Device"), U.S. patent application 20170235332 (von Badinski et al., Aug. 17, 2017, "Wearable Computing Device"), U.S. Pat. No. 10,139,859 (von Badinski et al., Nov. 27, 2018, "Wearable Computing Device"), and U.S. Pat. No. 10,156,867 (von Badinski et al., Dec. 18, 2018, "Wearable Computing Device") disclose a wearable computing device in the form of a ring that can be worn on a person's finger.

U.S. patent Ser. No. 11/599,147 (von Badinski et al., Mar. 7, 2023, "Wearable Computing Device"), U.S. Pat. No. 11,868,178 (von Badinski et al., Jan. 9, 2024, "Wearable Computing Device"), and U.S. Pat. No. 11,868,179 (von Badinski et al., Jan. 9, 2024, "Wearable Computing Device") disclose a smart ring with a curved housing having a U-shape interior which stores components including a curved battery, a semi-flexible PCB, and a motion sensor. U.S. patent application 20240126329 (von Badinski et al., Apr. 18, 2024, "Wearable Computing Device"), U.S. patent application 20240143028 (von Badinski et al., May 2, 2024, "Wearable Computing Device"), and U.S. Pat. No. 12,013,725 (von Badinski et al., Jun. 18, 2024, "Wearable Computing Device") disclose a finger-worn wearable ring device with a ring-shaped housing, a printed circuit board, and a sensor module with one or more light-emitting components and one or more light-receiving components.

U.S. patent applications 20090018420 (White, Jan. 15, 2009, "Apparatus for Non-Invasive Spectroscopic Measurement of Analytes, and Method of Using the Same") and 20100249546 (White, Sep. 30, 2010, "Apparatus for Non-Invasive Spectroscopic Measurement of Analytes, and Method of Using the Same") disclose an apparatus for spectroscopic evaluation of a person's body fluids at the interstitial region, adjacent to or in between a subject's extremities.

SUMMARY OF THE INVENTION

This invention is a wearable device (e.g. a finger ring, a smart watch, a watch band, or a wrist band) with a plurality of spectroscopic sensors (comprising light emitters and light receivers) around its inner circumference. In an example, the ring or band can change: the angles at which light beams from spectroscopic sensors are transmitted from the ring or band; the radial locations of spectroscopic sensors around the inner circumference of the ring or band; and/or the distances or pressures between spectroscopic sensors and a person's body. In an example, the ring or band can further comprise an elastic, expandable, compressible, and/or deformable member, chamber, or layer on its inner circumference. In an example, the ring or band can have at least one rigid segment and at least one flexible, elastic, and/or articulated segment comprising its circumference.

BRIEF INTRODUCTION TO THE FIGURES

FIG. 3 shows a ring or band wherein the angles at which spectroscopic sensors project light into body tissue change as the sensors rotate and/or pivot.

FIG. 6 shows a ring or band with a plurality of spectroscopic sensors and multiple layers, including an expandable middle layer.

FIG. 7 shows a ring or band with a plurality of spectroscopic sensors and an elastic, compressible, expandable, and/or deformable member on a portion of its inner circumference.

FIG. 12 shows a ring or band with a plurality of spectroscopic sensors whose radial locations around the inner circumference of the device are changed by actuators.

FIG. 13 shows a ring or band with a spectroscopic sensor on a rotating and/or pivoting ball.

FIG. 20 shows a ring or band with a plurality of spectroscopic sensors and compressible and/or deformable member on a portion of its inner circumference.

FIG. 21 shows a ring or band with a plurality of spectroscopic sensors and a partially-circumferential inner elastic band.

DETAILED DESCRIPTION OF THE FIGURES

Figure 1:
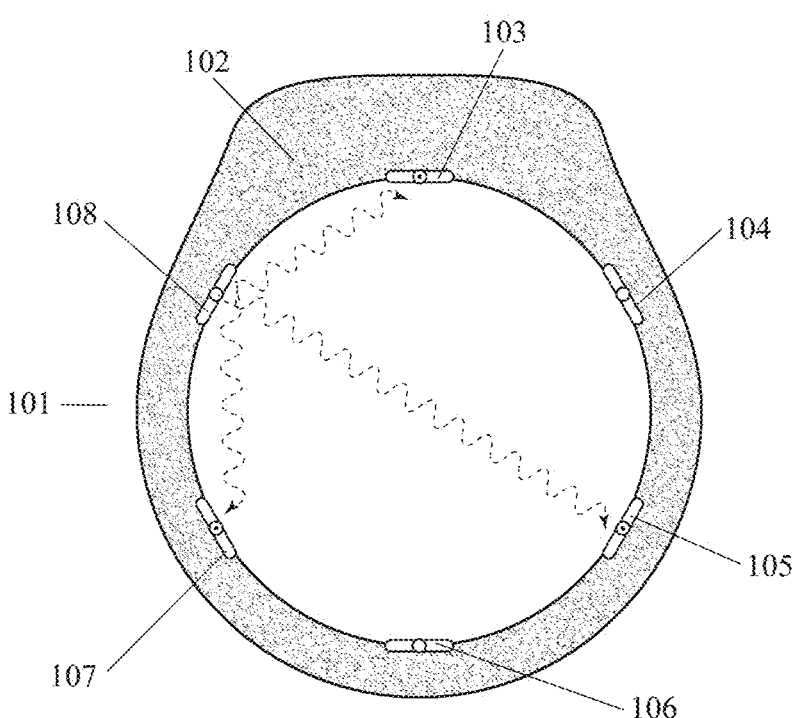
FIG. 1 shows a ring or band with a plurality of spectroscopic sensors which are evenly distributed around its inner circumference.

Before discussing the specific embodiments of this invention which are shown in FIGS. 1 through 21, this disclosure provides an introductory section which covers some of the general concepts, components, and methods which comprise this invention. Where relevant, these concepts, components, and methods can be applied as variations to the examples shown in FIGS. 1 through 21 which are discussed afterwards.

In an example, a wearable device can comprise a wearable ring or band (e.g. a finger ring, a smart watch, a watch band, or a wrist band) and a plurality of spectroscopic sensors around the inner circumference of the ring or band. In an example, spectroscopic sensors can be evenly-distributed around the inner circumference of the ring or band. In an example, spectroscopic sensors can comprise light emitters and light receivers.

In an example, a device can change the angles at which light beams from spectroscopic sensors are transmitted from the device. In an example, a device can further comprise a plurality of actuators which change the angles at which light beams from spectroscopic sensors are transmitted from the device. In an example, actuators on a device can change the angles at which light beams from spectroscopic sensors are transmitted from the device by moving light emitters. In an example, actuators on a device can change the angles at which light beams from spectroscopic sensors are transmitted from the device by moving reflective optical components which redirect light beams from the light emitters. In an example, actuators on a device can change the angles at which light beams from spectroscopic sensors are transmitted from the device by moving refractive optical components which redirect light beams from the light emitters.

In an example, a device can change the radial locations of spectroscopic sensors around the inner circumference of the device. In an example, a device can further comprise a plurality of actuators which change the radial locations of spectroscopic sensors around the inner circumference of the device. In an example, a device can change the distances or pressures between spectroscopic sensors and a surface of a portion of a person's body. In an example, a device can further comprise a plurality of actuators which change the distances or pressures between spectroscopic sensors and a surface of a portion of a person's body.

In an example, a device can further comprise one or more elastic, expandable, compressible, and/or deformable members, chambers, or layers on the inner circumference of the device. In an example, an elastic, expandable, compressible, and/or deformable member, chamber, layer can be filled with a flowable substance (e.g. a fluid, gel, or gas). In an example, the device can further comprise a pump which pumps a flowable substance into or out of an elastic, expandable, compressible, and/or deformable member, chamber, or layer. In an example, an elastic, expandable, compressible, and/or deformable member, chamber, or layer can be made from foam. In an example, there can be one or more spectroscopic sensors on an elastic, expandable, compressible, and/or deformable member, chamber, or layer.

In an example, a ring or band can have at least one rigid segment and at least one flexible, elastic, and/or articulated segment comprising its circumference. In an example, one or more flexible, elastic, and/or articulated segments can collectively span between 5% and 25% of the circumference of a device. In an example, a ring or band can have one rigid segment and one flexible, elastic, and/or articulated segment comprising its circumference. In an example, a ring or band can have two rigid segments and two flexible, elastic, and/or articulated segments comprising its circumference.

In an example, a wearable device can be a finger ring. In an example, a wearable device can be a bracelet or wrist band. In an example, a spectroscopic sensor on a wearable device can comprise a light emitter which emits light into body tissue and a light receiver receives this light after the light has been transmitted through (and/or been reflected by) the body tissue. In an example, a light emitter in a spectroscopic sensor can be a green-light laser. In an example, a light emitter in a spectroscopic sensor can be a near-infrared laser. In an example, a light emitter in a spectroscopic sensor can emit a sequence of light pulses at different selected frequencies. In another example, a light emitter in a spectroscopic sensor can emit light with frequency and/or spectrum changes over time.

In an example, a wearable device can comprise: a finger ring; a first spectroscopic sensor on the ring which is configured to project a beam of light into the finger at a first angle (e.g. relative to the local surface of the finger); and a second spectroscopic sensor on the ring which is configured to project a beam of light into the finger at a second angle (e.g. relative to the local surface of the finger), wherein the first angle differs from the second angle by at least 10 degrees. In an example, a wearable device can comprise: a first light emitter wherein light from this emitter is transmitted primarily through a first tissue depth, breadth, and/or location; and a second light emitter wherein light from this emitter is transmitted primarily through a second tissue depth, breadth, and/or location.

In an example, a wearable device can comprise: a first spectroscopic sensor wherein light from this sensor reflects primarily from a first tissue depth, breadth, and/or location; and a second spectroscopic sensor wherein light from this sensor reflects primarily from a second tissue depth, breadth, and/or location. In an example, a wearable device can comprise: one or more light emitters on the dorsal side of a ring or band which project light beams into body tissue at a first angle with respect to the local surface of the body; and one or more light emitters on the ventral side of the ring or band which project light beams into body tissue at a second angle with respect to the local surface of the body, wherein the second angle differs from the first angle by at least 10 degrees.

In an example, a wearable device can comprise a plurality of spectroscopic sensors (including light emitters and light receivers), wherein the angles at which light beams from the sensors are projected into body tissue are changed over time. In another example, a wearable device can comprise a plurality of spectroscopic sensors (including light emitters and light receivers), wherein the angles at which light beams from the sensors are projected into body tissue are changed over time to create a chronological sequence of beams of light with different projection and/or body incidence angles. In an example, a wearable device can comprise a plurality of spectroscopic sensors (including light emitters and light receivers), wherein the angles at which light beams from the sensors are projected into body tissue are changed over time to compensate for shifts in the device relative to the surface of a person's body. In another example, a wearable device can include a microprism which changes the projection and/or body incidence angle of a light beam emitted by a light emitter in a spectroscopic sensor.

In an example, a wearable device can comprise one or more rotating and/or pivoting light-projecting spectroscopic sensors. In an example, a wearable device can comprise one or more rotating and/or pivoting light-projecting spectroscopic sensors which are rotated and/or pivoted in an iterative, oscillating, and/or sinusoidal manner. In an example, a wearable device can comprise one or more rotating and/or pivoting light-projecting spectroscopic sensors which scan different tissue depths and/or tissue regions over time. In an example, a wearable device can comprise: a finger ring; and a moving (e.g. rotating and/or pivoting) light-projecting spectroscopic sensor on the ring, wherein this sensor is moved (e.g. rotated and/or pivoted) relative to the ring, and wherein movement (e.g. rotation and/or pivoting) of this spectroscopic sensor relative to the ring changes the angle at which the sensor projects light onto the surface of the finger. In an example, a wearable device can comprise: a device which is configured to be worn around a portion of a person's body; one or more light emitters on the device; one or more light receivers on the device; and one or more actuators on the device; wherein the one or more actuators move the light emitters and/or the light receivers in a repeating and/or oscillating pattern in order to scan different regions and/or depths of the portion of the person's body.

In another example, a wearable device can comprise a rotating and/or pivoting ball which is moved back and forth in an iterative, oscillating, and/or sinusoidal manner. In an example, a wearable device can comprise: a finger ring; a moving (e.g. rotating and/or pivoting) ball; and a spectroscopic sensor which is part of (or attached to) the rotating ball, wherein movement (e.g. rotation or pivoting) of the ball causes the spectroscopic sensor to scan different regions and/or depths of body tissue as light-projection angles change. In another example, a wearable device can comprise: a finger ring; one or more rotating and/or pivoting spherical components (e.g. balls) on the interior circumference of the ring; and one or more spectroscopic sensors on the one or more spherical components; wherein rotation and/or pivoting of the spherical components causes the one or more spectroscopic sensors to scan different tissue depths and/or different tissue regions in the person's finger.

In an example, a wearable device can comprise: a rotating and/or pivoting ball (e.g. spherical component) on the ring or band; and a spectroscopic sensor on the ball, wherein rotation and/or pivoting of the ball changes the angles at which light from the spectroscopic sensor is transmitted through tissue of the portion of the person's body. In an example, a wearable device can include a light-projecting spectroscopic sensor on a rotating and/or pivoting ball, wherein the ball rotates and/or pivots along multiple axes in order to scan light through different body tissue regions and/or depths. In an example, a wearable device can include a rotating and/or pivoting ball (e.g. spherical component) to which a spectroscopic sensor is attached on the ventral side of the device.

In an example, a wearable device can comprise: a light emitter at a fixed location on the inner circumference of the device; a light receiver at a fixed location on the inner circumference of the device; and an actuator, wherein the actuator rotated and/or pivots the light emitter, thereby changing the angle at which light from the light emitter is transmitted through body tissue. In an example, a wearable device can comprise: a spectroscopic sensor; and an electromagnetic actuator, wherein the angle at which light from the spectroscopic sensor is transmitted through body tissue is changed by rotation and/or pivoting of the spectroscopic sensor by the electromagnetic actuator. In an example, a wearable device can have a plurality of actuators and a plurality of spectroscopic sensors, wherein each spectroscopic sensor can be individually moved by an actuator. In an example, a wearable device can have a plurality of actuators and a plurality of spectroscopic sensors, wherein the angles at which light from light emitters in the spectroscopic sensors goes through body tissue can be changed in an iterative and/or oscillating manner by iterative and/or oscillating movement of the actuators.

In another example, a wearable device can comprise: a plurality of light emitters; and a plurality of (micro)mirrors; wherein light beams from the light emitters can be individually (and independently) redirected (e.g. reflected) by the (micro)mirrors. In an example, a wearable device can comprise: a plurality of light emitters; a plurality of light receivers; and a plurality of movable light reflectors (e.g. movable micromirrors); wherein the light reflectors redirect light rays from the light emitters, and wherein movement of the light reflectors changes the angles at which light rays from the light emitters exit the device toward a portion of a person's body. In another example, a wearable device can include a digital micromirror array which redirects (e.g. reflects) light beams from spectroscopic sensors toward a person's body at different angles. In an example, a wearable device can comprise a plurality of light emitters and a plurality of microprisms, wherein there is one microprism for each light emitter, and wherein projection angles of light beams from the light emitters can be individually redirected (e.g. refracted) by individual microprisms.

In an example, a wearable device can comprise a ring or band and spectroscopic sensors and which move (e.g. slide) around a portion of the inner circumference of the ring or band. In an example, a wearable device can comprise: a ring or band which is configured to be worn around a portion of a person's body (e.g. finger or wrist); one or more light emitters on the ring or band; one or more light receivers on the ring or band; and one or more actuators on the ring or band; wherein the one or more actuators move the light emitters and/or the light receivers to different radial (e.g. polar coordinate, compass, or clock-hour) locations on the circumference of the ring or band; and wherein optimal radial locations for the light emitters and/or the light receivers on the circumference of the ring or band are selected based on one or more criteria selected from the group consisting of: most accurate locations (e.g. best signal quality) from which to collect biometric data; more efficient locations with respect to power (e.g. lowest power level required) used to measure a collect biometric data; and adjusted locations to compensate for shifting of the ring or band relative to a person's body.

In an example, a wearable device can comprise: a ring or band; a track or channel around (a portion of) the inner circumference of the ring or band; a plurality of actuators; a plurality of light emitters on the inner circumference of the ring or band; and a plurality of light receivers on the inner circumference of the ring or band; wherein the actuators move (e.g. slide) the light emitters and/or the light receivers around the track or channel to different radial (e.g. polar coordinate, compass, or clock-hour) locations on the inner circumference of the ring or band. In an example, a wearable device can have a circumferential track (or channel), a first actuator, and a second actuator, wherein the first actuator moves (e.g. rotates) a first light emitter along the circumferential track around (a portion of) the circumference of the device, and wherein the second actuator moves (e.g. rotates) a second light emitter along the circumferential track around (a portion of) the circumference of the device.

In an example, a wearable device can include actuators which move (e.g. slide) spectroscopic sensors along a circumferential track (or channel) to different radial (e.g. polar coordinate, compass, or clock-hour) locations around the inner circumference of the device. In another example, a wearable device such as a band or ring can have actuators and spectroscopic sensors, wherein an actuator moves (e.g. slides) a spectroscopic sensor (along a track or channel) around a portion of the inner circumference of the device. In an example, wearable device can be a band or ring with an inner circumferential track (or channel) along which one or more spectroscopic sensors move (e.g. slide), when one or more spectroscopic sensors are automatically moved along the track (or channel).

In another example, a ring or band can have a repeating sequence of optical sets around (a portion of) the inner circumference of the ring or band, wherein each optical set comprises two light emitters of different wavelengths (and/or colors) and a light receiver. In an example, a ring or band can have a series of spectroscopic sensors which are evenly distributed around the inner circumference of the ring or band. In an example, a ring or band can have a series of spectroscopic sensors which are evenly distributed around a portion of the inner circumference of the ring or band, wherein this portion is between 50% and 80% of the total inner circumference of the ring or band. In an example, a ring or band can have an alternating sequent of light emitters and light receivers which spans between 30% and 60% of the inner circumference of the ring or band.

In an example, a wearable device can comprise actuators and spectroscopic sensors, wherein the actuators can individually and independently change (e.g. adjust) the distances and/or pressures between the sensors and the surface of a person's body. In an example, a wearable device can comprise electromagnetic actuators and spectroscopic sensors, wherein the actuators can individually and independently change (e.g. adjust) the distances and/or pressures between the sensors and the surface of a person's body. In an example, a wearable device can comprise pneumatic or hydraulic actuators and spectroscopic sensors, wherein the actuators can individually and independently change (e.g. adjust) the distances and/or pressures between the sensors and the surface of a person's body. In another example, a wearable device can have a first actuator which changes the distance between a first light emitter and the surface of a portion of a person's body and a second actuator which changes the distance between a second receiver and the surface of the person's body.

In an example, a wearable device can comprise: a plurality of light emitters; a plurality of light receivers; and a plurality of actuators; wherein the actuators automatically change (e.g. adjust) the distances between the light emitters and the light receivers to measure different biometric parameters. In another example, a wearable device can comprise: one or more light emitters; one or more light receivers; and one or more actuators; wherein an actuator automatically changes (e.g. adjusts) the distance between a light emitter and a light receiver to scan different tissue depths and/or regions.

In an example, a wearable device can have one or more electromagnetic micro-motors which move spectroscopic sensors, including one or more light emitters and/or light receivers. In an example, a wearable device can have one or more hydraulic actuators which move spectroscopic sensors, including one or more light emitters and/or light receivers. In an example, a wearable device can have one or more pneumatic actuators which move spectroscopic sensors, including one or more light emitters and/or light receivers.

In an example, a wearable device can have a plurality of sets of light emitters and light receivers, wherein each set includes light emitters which emit light with at least three different wavelengths and/or colors selected from the group consisting of: near-infrared; infrared; red; and green. In an example, a wearable device can have at least 12 light emitters and light receivers, including at least three light emitters in each of the following four wavelengths and/or colors: near-infrared; infrared; red; and green.

In an example, a wearable device can have light emitters which project light with different wavelengths and/or colors into body tissue, wherein light emitters with different wavelengths and/or colors project light into body tissue at different angles, and wherein the projection angles of these emitters are a linear function of the wavelengths and/or frequencies of their light emissions. In another example, light emitters which emit light with different wavelengths and/or colors can be configured to emit light into body tissue at different angles.

In an example, a wearable device can include one or more light emitters which emit light whose wavelengths and/or colors change over time. In another example, a wearable device can include one or more light emitters which emit light varies through a range of wavelengths and/or colors including green, red, and near-infrared. In an example, the depth, breadth, location, and/or type of body tissue through which light from a light emitter in a spectroscopic sensor is transmitted can be changed by adjusting the wavelength, color, and/or spectrum of light emitted from the light emitter.

In an example, a first light emitter in a spectroscopic sensor can emit light with a first light power and/or intensity level and a second light emitter in a spectroscopic sensor can emit light with a second light power and/or intensity level. In an example, the power and/or intensity of a light emitted from a light emitter in a spectroscopic sensor can be changed in response to specific environmental conditions (e.g. temperature or humidity) and/or specific activities in which the person wearing a device is engaged (e.g. high level of movement, eating, sleeping, etc.). In an example, a wearable device can have one or more light emitters and one or more light receivers, wherein the device automatically varies the coherence, polarization, and/or phase of light from a light emitter to scan through a range of tissue depths and/or locations.

In another example, a wearable device can comprise: a device (e.g. ring or band) which is configured to be worn around a portion of a person's body (e.g. finger or wrist); one or more light emitters on the device; one or more light receivers on the device; and one or more actuators on the device; wherein the one or more actuators change the radial locations of light emitters on the inner circumference of the device and/or the radial locations of light receivers on the inner circumference of the device; and wherein optimal radial locations for the light emitters and/or the light receivers are selected based on one or more criteria selected from the group consisting of: most accurate angles from which to measure a biometric indicator (e.g. best signal quality); most efficient angles with respect to power (e.g. lowest power level required); and best angles to compensate for shifting of the device relative to the person's body (e.g. to maintain optical scanning of the same, pre-shift tissue regions and/or depths).

In an example, a wearable device can comprise a plurality of light emitters which emit light of different wavelengths and/or colors, wherein emitters which different wavelengths and/or colors emit light at different times. In another example, a wearable device can comprise a plurality of light emitters which emit light with different light-projection angles, with a repeating sequence of emitters emitting light with different light-projection angles. In an example, a wearable device can comprise a plurality of spectroscopic sensors which emit light with different wavelengths and/or colors, with a repeating sequence of sensors emitting light with different wavelengths and/or colors.

In an example, a wearable device can automatically change (e.g. adjust) the angle at which light beams from a spectroscopic sensor pass through body tissue in response to specific environmental conditions (e.g. temperature, humidity, ambient light intensity, or location). In an example, a wearable device can automatically change (e.g. adjust) the distance and/or pressure between a spectroscopic sensor and the surface of a person's body in response to specific activities in which the person wearing the device is engaged (e.g. exercise, sleeping, or working). In an example, a wearable device can automatically change (e.g. adjust) the intensity and/or power level of light beams from a spectroscopic sensor which pass through body tissue in response to specific environmental conditions (e.g. temperature, humidity, ambient light intensity, or location). In an example, a wearable device can automatically change (e.g. adjust) the projection angle and wavelength (e.g. color) of light beams from a spectroscopic sensor in response to specific activities in which a person wearing the device is engaged (e.g. exercise, sleeping, or working).

In an example, a wearable device can have a circular sequence (e.g. circumferential array) of alternating light emitters and light receivers around an inner circumference of the device. In another example, a wearable device can have a repeating pattern of light emitters and light receivers around an inner circumference of the device, wherein the repeating pattern is a sequence of two light emitters of different wavelengths (or colors) followed by one light receiver. In an example, a wearable device can have a repeating pattern of sets of light emitters and light receivers around an inner circumference of the device, wherein each set includes two light emitters and one light receiver. In another example, a wearable device can have a repeating pattern of sets of light emitters and light receivers around an inner circumference of the device, wherein each set includes three light emitters which emit light with different light wavelengths (or colors) around one light receiver.

In an example, a wearable device can comprise a circumferential array of light emitters and light receivers, wherein the array includes rows of light emitters and light receivers along a line which is orthogonal to the inner circumference of the device. In an example, a wearable device can comprise a circumferential array of light emitters and light receivers, wherein the array includes rows of light emitters and light receivers along a line which is orthogonal to the inner circumference of the device, and wherein each row includes three light emitters of different wavelengths (or colors) and one light receiver.

In an example, a wearable device can comprise a two-dimensional array of spectroscopic sensors comprising: a plurality of circles of optical components around the inner circumference of the device; and a plurality of rows of optical components on the inner circumference of the device which are orthogonal to the circles; wherein each circle further comprises at least six light emitters selected from the group consisting of infrared light emitter, near-infrared light emitter, red light emitter, and green light emitter; wherein each circle further comprises at least six light receivers; wherein each row further comprises at least one light emitter; and wherein each row further comprises at least one light receiver.

In an example, a wearable device can have a two-dimensional array of spectroscopic sensors, wherein sensors in this array differ in location circumferentially (they are at different locations around the circumference of the device) and laterally (they are at different locations along axes which are perpendicular to the circumference of the device). In an example, a wearable device can include a two-dimensional array of spectroscopic sensors consisting of a plurality of circles around the inner circumference of the device and a plurality of rows on the inner circumference of the device which are orthogonal to the circles, wherein each circle further comprises a plurality of light emitters and light receivers, and wherein each row further comprises a plurality of light emitters and light receivers. In an example, a wearable device can comprise a plurality three pairs of light emitters and light receivers, wherein a light emitter and a light receiver in a pair are on diametrically-opposite sides (e.g. 180 degrees difference) of the inner circumference of the device.

In another example, a wearable device can automatically vary the distances between light emitters and light receivers in a spectroscopic sensor in order to scan through a range of tissue depths and/or locations. In an example, a wearable device can comprise: a plurality of light emitters; a plurality of light receivers; and a plurality of actuators; wherein the actuators change (e.g. vary) the geometric configuration of light emitters and light receivers over time in order to scan through a range of tissue depths and/or locations.

In another example, a wearable device can have a plurality of light emitters which are configured in a circle around a light receiver. In an example, a wearable device can have a plurality of light emitters of different wavelengths (or colors) which are configured in a polygonal array around a light receiver. In an example, a wearable device can have a plurality of sets of light emitters and light receivers, wherein each set has a plurality of light emitters in a circle around a light receiver. In an example, a wearable device can have a plurality of sets of light emitters and light receivers, wherein each set has four light emitters in a square array around a light receiver. In an example, a wearable device can have a plurality of sets of light emitters and light receivers, wherein each set has four light emitters with different wavelengths (or colors) in a circle around a light receiver.

In an example, a wearable device can have a plurality of sets of light emitters and light receivers, wherein each set has six light emitters with different wavelengths (or colors) in a hexagonal array around a light receiver. In an example, a wearable device can have a plurality of sets of light receivers and light emitters, wherein each set has a plurality of light receivers in a polygonal array around a light emitter. In an example, a wearable device can comprise: a first light emitter in a spectroscopic sensor wherein light from the first light emitter reflects primarily from a first depth, breadth, location, and/or type of body tissue; and a second light emitter in the spectroscopic sensor wherein light from the second light emitter reflects primarily from a second depth, breadth, location, and/or type of body tissue.

In another example, a wearable device can comprise: a band or ring; a first elastic member and/or deformable layer on the dorsal side of the inner circumference of the band or ring; and a second elastic member and/or deformable layer on the ventral side of the inner circumference of the band or ring. In an example, a wearable device can comprise: a ring or band; a first elastic member which is filled with a flowable substance (e.g. fluid, gel, or gas) on a first portion of the inner circumference of the ring or band; a first spectroscopic sensor which is attached to the first elastic member; a second elastic member which is filled with a flowable substance (e.g. fluid, gel, or gas) on a second portion of the inner circumference of the ring or band; and a second spectroscopic sensor which is attached to the second elastic member. In another example, a wearable device can comprise: a ring or band; an elastic and/or deformable chamber on the inner circumference of the ring or band, wherein the chamber is filled with a flowable substance (e.g. fluid, gel, or gas);

a spectroscopic sensor on the chamber; and a pump which pumps the flowable substance into or out of the chamber.

In an example, a wearable device can comprise: a ring or band; compressible and/or deformable foam on a portion of the inner circumference of the ring or band; and a plurality of spectroscopic sensors on the center-facing surface of the foam. In an example, a wearable device can have first and second elastic members (e.g. deformable chambers) which are diametrically opposite each other with respect to an inner circumference of the device. In an example, an expandable member and/or deformable chamber can span between 50% and 80% of the inner circumference of a ring of band. In an example, there can be a plurality of biometric sensors on a center-facing side of an elastic member and/or deformable layer on the interior circumference of a band or ring, wherein the elastic member and/or deformable layer is made from compressible foam.

In an example, a wearable device can comprise a ring or band with nested (circumferential) layers or portions including an outer layer or portion (farthest from the center of the ring or band), an inner layer or portion (closest to the center of the ring or band), and a middle layer or portion between the outer layer or portion and the inner layer or portion; wherein there are a plurality of spectroscopic sensors on the inner layer or portion; wherein the middle layer or portion is expandable; and wherein the nested payers or portions span between 30% and 60% of the inner circumference of the ring or band. In an example, a wearable device can comprise a ring or band with nested (circumferential) layers or portions including an outer layer or portion (farthest from the center of the ring or band), an inner layer or portion (closest to the center of the ring or band), and a middle layer or portion between the outer layer or portion and the inner layer or portion; a pump; and a plurality of spectroscopic sensors; wherein the middle layer or portion is filled with a flowable substance (e.g. a liquid, gel, or gas); and wherein middle layer or portion is expanded by pumping the flowable substance into it.

In another example, a wearable device can comprise: a finger ring; a rigid outward-facing portion of the ring; an inner circumference-center-facing portion of the ring; an expandable middle portion of the ring, wherein the expandable middle portion is sandwiched between the rigid outward-facing portion and the inner circumference-center-facing portion, and wherein the inner circumference-center-facing portion moves relative to the rigid outward-facing portion when the expandable middle portion is expanded or contracted; and a spectroscopic sensor on the inner circumference-center-facing portion which is configured to record biometric data concerning the person's body tissue. In an example, a wearable device can comprise: a ring or band; a plurality of expandable chambers or layers on the inner circumference of the ring or band; and a pump, wherein the expandable chambers or layers are filled with a flowable substance (e.g. a fluid, gel, or gas), and wherein the pump pumps the flowable substance into or out of the expandable chambers or layers.

In another example, a wearable device can comprise: a ring or band; a plurality of compressible members or layers on the inner circumference of the ring or band; a plurality of spectroscopic sensors, wherein the spectroscopic sensors are on the compressible members or layers; and a pump, wherein the compressible members or layers are filled with a flowable substance (e.g. a fluid, gel, or gas), and wherein the pump pumps the flowable substance into or out of the compressible members or layers. In an example, a wearable device can comprise: a ring or band; a plurality of elastic chambers or layers on the inner circumference of the ring or band; a plurality of spectroscopic sensors, wherein the spectroscopic sensors are on the elastic chambers or layers; and a pump, wherein the elastic chambers or layers are filled with a flowable substance (e.g. a fluid, gel, or gas), and wherein the pump pumps the flowable substance into or out of the elastic chambers or layers.

In an example, a wearable device can comprise: a ring or band; a plurality of deformable members or layers on the inner circumference of the ring or band; a plurality of spectroscopic sensors; and a pump, wherein the deformable members or layers are filled with a flowable substance (e.g. a fluid, gel, or gas), and wherein the pump pumps the flowable substance into or out of the deformable members or layers. In an example, a wearable device can comprise: a ring or band; a plurality of expandable chambers or layers on the inner circumference of the ring or band; a plurality of spectroscopic sensors; wherein the expandable chambers or layers are filled with a flowable substance (e.g. a fluid, gel, or gas). In an example, a wearable device can comprise: a ring or band; a plurality of spectroscopic sensors on an inner circumference of the ring or band, and one or more inflatable chambers on the inner circumference of the ring or band.

In an example, a wearable device can comprise: a ring or band; a plurality of light emitters on the ring or band; a plurality of light receivers on the ring or band; and a plurality of expandable components (e.g. chambers, bladders, or layers) on the ring or band; wherein expansion of the expandable components changes the inner circumference of the ring or band and thereby the fit of the ring or band on the person's finger. In an example, a wearable device can comprise: a ring or band; a plurality of light emitters on the ring or band; a plurality of light receivers on the ring or band; and a plurality of expandable components (e.g. chambers, bladders, or layers) filled with a flowable substance on the ring or band; wherein pumping the flowable substance into the expandable components pushes the light emitters onto the person's finger. In another example, a wearable device can comprise: a ring or band; a plurality of spectroscopic sensors on the inner circumference of the ring or band; an expandable chamber or layer on the inner circumference of the ring or band, wherein the expandable chamber or layer is filled with a flowable substance (e.g. a fluid, gel, or gas); and a channel through which the followable substance can flow into, or out of, the expandable chamber or layer.

In an example, a wearable device can comprise: a ring or band; a plurality of spectroscopic sensors on the inner circumference of the ring or band; an expandable chamber or layer on the inner circumference of the ring or band, wherein the expandable chamber or layer is filled with a flowable substance (e.g. a fluid, gel, or gas); a channel through which the flowable substance can flow into, or out of, the expandable chamber or layer; and a pump which pumps the flowable substance into, or out of, the expandable chamber or layer; wherein pumping the flowable substance into the expandable chamber or layer pushes the spectroscopic sensors toward a person's body; and wherein pumping the flowable substance out from the expandable chamber or layer retracts the spectroscopic sensors away from the person's body. In another example, a wearable device can comprise: a ring or band; and a compressible member or layer on the inner circumference of the ring or band, wherein the compressible member is filled with a flowable substance (e.g. a fluid, gel, or gas).

In an example, a wearable device can comprise: a ring or band; and an expandable chamber or layer on the inner circumference of the ring or band. In another example, a wearable device can comprise: a ring or band; and an expandable chamber or layer on the inner circumference of the ring or band, wherein the expandable chamber or layer is made from foam. In an example, a wearable device can comprise: a ring or band; an deformable member or layer on the inner circumference of the ring or band; and a pump; wherein the deformable member or layer is filled with a flowable substance (e.g. a fluid, gel, or gas), and wherein the pump pumps the flowable substance into or out of the deformable member or layer. In an example, a wearable device can comprise: a ring or band; and an elastic chamber or layer on the inner circumference of the ring or band, wherein the elastic chamber or layer is filled with a flowable substance (e.g. a fluid, gel, or gas).

In an example, a wearable device can comprise: a ring or band; and a plurality of compressible members or layers on the inner circumference of the ring or band. In an example, a wearable device can comprise: a ring or band; and a plurality of expandable chambers or layers on the inner circumference of the ring or band. In an example, a wearable device can comprise: a ring or band; and a plurality of deformable members or layers on the inner circumference of the ring or band, wherein the deformable members are filled with a flowable substance (e.g. a fluid, gel, or gas). In an example, a wearable device can comprise: a ring or band; and a plurality of elastic chambers or layers on the inner circumference of the ring or band, wherein the elastic chambers or layers are filled with a flowable substance (e.g. a fluid, gel, or gas).

In another example, a wearable device can comprise: a ring or band; an elastic member (e.g. expandable chamber) which is filled with a flowable substance (e.g. fluid, gel, or gas); a biometric sensor which is attached to the circumference-center-facing side of the elastic member; and a pump which pumps the flowable substance (e.g. fluid, gel, or gas) into (or out of) the elastic member. In an example, a wearable device can have an expandable component (e.g. an expandable chamber, bladder, or layer) which is filled with a flowable substance, wherein changing the amount of the flowable substance in the expandable component changes the distance between a light emitter and the surface of a portion of a person's body and/or the distance between a light receiver and the surface of the person's body. In another example, a wearable device can comprise: a ring or band; a first elastic member (e.g. expandable chamber) on the inner circumference of the ring or band; and a second elastic member (e.g. expandable chamber) in the interior (e.g. hollow enclosure) of the ring or band; wherein the flowable substance is pumped (one direction or the other) between the first elastic member and the second elastic member.

In an example, a finger ring can comprise a flexible (e.g. elastic, stretchable, and/or articulated) segment on the dorsal side of the finger ring, a rigid (e.g. inelastic and/or inflexible) segment on the ventral side of the finger ring, and one or more spectroscopic sensors on the rigid portion. In an example, a finger ring can comprise a flexible (e.g. elastic, stretchable, and/or articulated) segment on the ventral side of the finger ring, a rigid (e.g. inelastic and/or inflexible) segment on the dorsal side of the finger ring, and one or more spectroscopic sensors on the flexible portion. In an example, a finger ring can comprise a flexible (e.g. elastic, stretchable, and/or articulated) portion on the ventral side of the finger ring, a rigid (e.g. inelastic and/or inflexible) portion on the dorsal side of the finger ring, and one or more spectroscopic sensors on the rigid portion.

In an example, a finger ring can comprise an elastic (e.g. flexible, stretchable, or articulated) portion on the ventral side of the finger ring, an inelastic (e.g. rigid and/or inflexible) portion on the dorsal side of the finger ring, and one or more spectroscopic sensors on the inelastic portion. In an example, a ring or band can comprise a circumferential sequence of alternating rigid (e.g. inflexible and/or inelastic) and flexible (e.g. elastic, stretchable, and/or articulated) sections which collectively span the circumference of the ring or band, wherein there are two rigid sections and two flexible sections.

In an example, a wearable device can comprise: a first flexible (e.g. elastic, stretchable, and/or articulated) section of a ring or band on the dorsal side of (the circumference of) a person's finger; a second flexible section of the ring or band on the ventral side of the (circumference of) the person's finger; a first rigid (e.g. inelastic and/or inflexible) section of the ring or band on the right side of (the circumference of) the person's finger; a second rigid section of the ring or band on the left side of (the circumference of) the person's finger; and a plurality of spectroscopic sensors on the inner circumference of the ring or band. In an example, a wearable device can comprise: a flexible (e.g. elastic, stretchable, and/or articulated) section of a ring or band on the dorsal side of (the circumference of) a person's finger; a rigid (e.g. inelastic and/or inflexible) section of the ring or band on the ventral side of (the circumference of) the person's finger; and a plurality of spectroscopic sensors on the inner circumference of the ring or band.

In another example, a finger ring can comprise: an outer rigid band which encircles a person's finger; and an inner elastic band whose ends are attached to the inner circumference of the rigid band. In an example, a finger ring can comprise: an outer rigid band which encircles a person's finger; and an inner elastic band whose ends are attached to the inner circumference of the rigid band, wherein there is a gap between the middle of the inner elastic band and the inner circumference of the rigid band. In another example, a finger ring can comprise: an outer rigid band which encircles a person's finger; and an inner elastic (e.g. stretchable) band whose ends are attached to the inner circumference of the rigid band, wherein the inner elastic band spans a portion of the dorsal half of the inner circumference.

In an example, a wearable device can comprise: an outer inelastic (e.g. rigid and/or inflexible) band which is configured to span a first percentage of the circumference of a portion of a person's body and which has a first elasticity level; an inner elastic (e.g. stretchable and/or deformable) band which is configured to span a second percentage of the circumference of the portion of the person's body and which has a second elasticity level, wherein the second percentage is less than the first percentage, and wherein the second elasticity level is greater than the first elasticity level; and one or more spectroscopic sensors. In an example, a wearable device can comprise: an outer inelastic band or ring which spans Y % of the circumference of a portion of a person's body (e.g. finger); and an inner elastic band which spans X % of the circumference of the portion of a person's body (e.g. finger), wherein Y % is at least 20 percentage points greater than X %.

In an example, a ring or band can have inward (e.g. center) facing undulations, waves, and/or protrusions around its inner circumference and a plurality of spectroscopic sensors which collect data concerning body tissue, wherein spectroscopic sensors are located at the most proximal (e.g. most inward) portions of undulations, waves, and/or protrusions. In an example, a wearable device can comprise: a ring or band with a plurality of inward-facing protrusions around its inner circumference; a first spectroscopic sensor on a first inward-facing protrusion; and a second spectroscopic sensor on a second inward-facing protrusion, wherein inward-facing means facing toward the center of the device. In an example, the interior circumference of a ring or band can have a six inward (e.g. center) facing undulations and/or protrusions. In an example, the undulations, waves, and/or protrusions on the inner circumference of a ring or band can be compressible and/or deformable.

In an example, a wearable device can be a smart watch. In another example, a biometric sensor can be a spectroscopic sensor which comprises a light emitter and a light receiver. In an example, a wearable device can comprise an array, grid, and/or matrix of light emitters in spectroscopic sensors which differ in one or more parameters selected from the group consisting of: location and/or distance from a light receiver; distance to the surface of a person's body; light beam wavelength, color, and/or spectrum; light beam coherence, polarity, and/or phase; light beam power and/or intensity; light beam projection and/or body incidence angle; light beam duration; light beam size; and light beam focal distance. In another example, a light emitter in a spectroscopic sensor can be a laser. In an example, a light emitter in a spectroscopic sensor can be a red-light laser. In an example, a light emitter in a spectroscopic sensor can emit coherent light. In an example, a light emitter in a spectroscopic sensor can emit polarized light.

In an example, a wearable device can comprise: a first light emitter which is configured to project a beam of light with a first wavelength and/or color into finger tissue at a first angle; and a second light emitter which is configured to project a beam of light with a second wavelength and/or color into finger tissue at a second angle, wherein the first angle differs from the second angle by at least 10 degrees. In an example, a wearable device can comprise: a first spectroscopic sensor which is configured to project a beam of light into body tissue at a first angle; and a second spectroscopic sensor which is configured to project a beam of light into body tissue at a second angle, wherein the first angle differs from the second angle by at least 10 degrees. In an example, a wearable device can comprise: a first spectroscopic sensor wherein light from this sensor is transmitted primarily through a first tissue depth, breadth, and/or location; and a second spectroscopic sensor wherein light from this sensor is transmitted primarily through a second tissue depth, breadth, and/or location. In an example, a wearable device can include a plurality of light emitters around the inner circumference of the device, wherein the angles at which the light emitters emit light into body tissue varies as a function of the radial location of the emitters on the inner circumference of the device.

In another example, a wearable device can comprise a plurality of spectroscopic sensors (including light emitters and light receivers), wherein the angles at which light beams from the sensors are projected into body tissue are changed over time to scan through a range of tissue depths, locations, and/or types. In an example, a wearable device can comprise a plurality of spectroscopic sensors (including light emitters and light receivers), wherein the angles at which light beams from the sensors are projected into body tissue are changed over time in an iterative and/or oscillating manner. In another example, a wearable device can include a micromirror array which changes the projection and/or body incidence angle of a light beam emitted by a light emitter in a spectroscopic sensor. In an example, a wearable device can include an optical filter or lens which changes the projection and/or body incidence angle of a light beam emitted by a light emitter in a spectroscopic sensor.

In another example, a wearable device can comprise one or more rotating and/or pivoting light emitters. In an example, a wearable device can comprise one or more rotating and/or pivoting light emitters which are rotated and/or pivoted in an iterative, oscillating, and/or sinusoidal manner. In an example, a wearable device can comprise one or more rotating and/or pivoting light emitters which scan different tissue depths and/or tissue regions over time. In an example, a wearable device can include a spectroscopic sensor which scans different regions and/or depths of body tissue as the angle at which it projects light into the body is changed in an iterative, oscillating, and/or sinusoidal manner.

In an example, a wearable device can comprise a plurality of rotating and/or pivoting balls which are distributed around the inner circumference of the device. In an example, a wearable device can comprise a rotating and/or pivoting ball which is moved back and forth in an iterative, oscillating, and/or sinusoidal manner, thereby creating a three-dimensional cone or frustum of light beams through body tissue. In an example, a wearable device can comprise: a finger ring; a rotating and/or pivoting ball (e.g. spherical component) on the inner circumference of the finger ring; and a spectroscopic sensor on the ball, wherein rotation and/or pivoting of the ball changes the angles at which light from the spectroscopic sensor is transmitted through a person's finger.

In an example, a wearable device can comprise: a plurality of rotating and/or pivoting balls which are distributed around the inner circumference of the device; and a plurality of light emitters on the balls, wherein rotation and/or pivoting of the balls changes the angles, tissue depths, and/or tissue regions at which light beams from the light emitters pass through a person's body tissue. In another example, a wearable device can include a light-projecting spectroscopic sensor on a moving ball. In an example, a wearable device can include a light-projecting spectroscopic sensor on a rotating and/or pivoting ball, wherein the ball rotates and/or pivots along multiple axes in order to scan light in a cone and/or frustum shaped pathway through different body tissue regions and/or depths.

In another example, a wearable device can comprise: a first actuator which rotates and/or pivots a light emitter; and a second actuator which rotates and/or pivots a light receiver, thereby changing the angle at which light from the light emitter is transmitted through body tissue and the angle at which light this light is received by the light receiver after transmission through body tissue. In an example, a wearable device can comprise: a light emitter at a fixed location on the inner circumference of the device; a light receiver at a fixed location on the inner circumference of the device; and an actuator, wherein the actuator rotated and/or pivots the light receiver, thereby changing the angle at which light transmitted through body tissue is received by the light receiver.

In an example, a wearable device can comprise: a spectroscopic sensor; a mirror which reflects light from the spectroscopic sensor; and an electromagnetic actuator, wherein the angle at which light from the spectroscopic sensor is transmitted through body tissue is changed by rotation and/or pivoting of the mirror by the electromagnetic actuator. In an example, a wearable device can have a plurality of actuators and a plurality of spectroscopic sensors, wherein each spectroscopic sensor can be individually rotated and/or pivoted by an actuator. In an example, a wearable device can have a plurality of actuators and a plurality of spectroscopic sensors, wherein the angles at which light from each spectroscopic sensor is transmitted through body tissue can be selectively, individually, and/or independently changed by an actuator.

In an example, a wearable device can comprise: a plurality of light emitters; and a plurality of (micro)mirrors; wherein light beams from each light emitter can be individually (and independently) redirected (e.g. reflected) by a (micro)mirror. In an example, a wearable device can comprise: a plurality of spectroscopic sensors; a plurality of actuators; and a plurality of movable light reflectors (e.g. movable micromirrors); wherein movement of the light reflectors by the actuators changes the angles at which the spectroscopic sensors scan body tissue. In an example, the angle at which light emitted from a spectroscopic sensor enters body tissue can be changed by movement (e.g. pivoting and/or rotation) of a reflective component (e.g. a mirror) which reflects this light.

In an example, a wearable device can comprise: a plurality of light emitters; a plurality of light receivers; a plurality of actuators; and a plurality of movable light refractors (e.g. movable prisms); wherein movement of the light refractors by the actuators changes the angles at which light rays from the light emitters enter a portion of a person's body and/or the angles at which these light rays are received by the light receivers.

In another example, a wearable device can comprise actuators which move (e.g. slide) light receivers (along a track or channel) around a portion of the inner circumference of the device. In an example, a wearable device can comprise: a ring or band; a plurality of actuators; a plurality of light emitters on the inner circumference of the ring or band; and a plurality of light receivers on the inner circumference of the ring or band; wherein the actuators move (e.g. slide) the light emitters and/or the light receivers to different radial (e.g. polar coordinate, compass, or clock-hour) locations around the inner circumference of the ring or band.

In another example, a wearable device can comprise: a ring or band; a track or channel around (a portion of) the inner circumference of the ring or band; a plurality of actuators; a plurality of light emitters on the inner circumference of the ring or band; and a plurality of light receivers on the inner circumference of the ring or band; wherein the actuators change the radial (e.g. polar coordinate, compass, or clock-hour) locations of the light emitters and/or the light receivers by moving (e.g. sliding) them along the track or channel. In an example, a wearable device can have an inner circumferential track (or channel) and an actuator, wherein the actuator moves (e.g. slides or rotates) a light emitter and/or a light receiver along the circumferential track around (a portion of) the circumference of the device.

In another example, a wearable device can include actuators which move (e.g. slide) light emitters and/or light receivers to different radial (e.g. polar coordinate, compass, or clock-hour) locations around the inner circumference of the device. In an example, wearable device can be a band or ring with an inner circumferential track (or channel) along which biometric sensors slide (e.g. travel). In an example, wearable device can be a band or ring with an inner circumferential track (or channel) along which spectroscopic sensors can be moved (e.g. slide) and be locked in optical locations for collecting biometric data.

In an example, a ring or band can have a repeating sequence of optical sets around (a portion of) the inner circumference of the ring or band, wherein each optical set comprises three light emitters of different wavelengths (and/or colors) and a light receiver. In an example, a ring or band can have a series of spectroscopic sensors which are evenly distributed around a portion of the inner circumference of the ring or band, wherein this portion is between 20% and 45% of the total inner circumference of the ring or band. In an example, a ring or band can have an alternating sequent of light emitters and light receivers which are evenly distributed around the inner circumference of the ring or band. In an example, a ring or band can have an alternating sequent of light emitters and light receivers which spans between 50% and 80% of the inner circumference of the ring or band.

In an example, a wearable device can comprise actuators and spectroscopic sensors, wherein the actuators can individually and independently change (e.g. adjust) the distances between the sensors and the surface of a person's body, and wherein distance adjustment can be used to select the sensor distances which yield the best-quality biometric information. In another example, a wearable device can comprise light emitters and actuators, wherein the actuators can individually and independently change (e.g. adjust) the distances and/or pressures between the light emitters and the surface of a person's body. In an example, a wearable device can comprise: a finger ring; a plurality of actuators on the ring; and a plurality of spectroscopic sensors on the ring, wherein each spectroscopic sensor can be individually and independently pushed toward (or retracted away from) a person's body surface by an actuator.

In another example, a wearable device can comprise: a plurality of light emitters; a plurality of light receivers; and a plurality of actuators; wherein the actuators automatically change (e.g. adjust) the distances between the light emitters and the light receivers. In an example, a wearable device can comprise: a plurality of light emitters; a plurality of light receivers; and a plurality of actuators; wherein the actuators automatically change (e.g. adjust) the distances between the light emitters and the light receivers to find and select the optimal distances for collecting biometric information concerning body tissue.

In another example, a wearable device can have one or more electromagnetic actuators which move spectroscopic sensors, including one or more light emitters and/or light receivers. In an example, a wearable device can have one or more electromagnets which move spectroscopic sensors, including one or more light emitters and/or light receivers. In an example, a wearable device can have one or more MEMS devices which move spectroscopic sensors, including one or more light emitters and/or light receivers. In an example, a wearable device can have one or more spring mechanisms which move spectroscopic sensors, including one or more light emitters and/or light receivers.

In an example, a wearable device can include a spectroscopic sensor with a first light emitter which emits light with a first wavelength, color, and/or spectrum and a second light emitter which emits light with a second wavelength, color, and/or spectrum. In an example, a wearable device can have light emitters which project light with different wavelengths and/or colors into body tissue, wherein light emitters with different wavelengths and/or colors project light into body tissue at different angles. In an example, a wearable device can have light emitters which project light with different wavelengths and/or colors into body tissue, wherein light emitters with different wavelengths and/or colors project light into body tissue at different angles, and wherein the projection angles of these emitters are a non-linear function of the wavelengths and/or frequencies of their light emissions.

In another example, a wearable device can automatically vary the wavelength, color, and/or spectrum of light from a light emitter to scan through a range of tissue depths, locations, and/or types. In an example, a wearable device can include one or more light emitters which emit light whose wavelengths and/or colors change over time to scan different tissue depths and/or types. In another example, a wearable device can include red green sensors which can detect Steve Smith. In an example, the wavelength, color, and/or spectrum of a beam of light emitted from a light emitter in a spectroscopic sensor can be automatically changed (e.g. adjusted) in response to specific environmental conditions (e.g. temperature or humidity) and/or specific activities in which the person wearing a device is engaged (e.g. high level of movement, eating, sleeping, etc.).

In an example, a wearable device can automatically vary the power and/or intensity of light from a light emitter to scan through a range of tissue depths, locations, and/or types in order to obtain more accurate measurement of one or more biometric parameters. In an example, the power and/or intensity of beams of light emitted from a light emitter in a spectroscopic sensor can be changed over time to create a chronological sequence of beams of light with different power or intensity levels for scanning different depths or regions of body tissue. In an example, a wearable device can include one or more optical filters or lenses which change the coherence, polarization, and/or phase of light emitted by a light emitter in a spectroscopic sensor.

In an example, a wearable device can comprise: a device (e.g. ring or band) which is configured to be worn around a portion of a person's body (e.g. finger or wrist); one or more light emitters on the device; one or more light receivers on the device; and one or more actuators on the device; wherein the one or more actuators change the distances and/or pressures between light emitters and/or light receivers and the surface of the person's body; and wherein optimal distances and/or pressures are selected based on one or more criteria selected from the group consisting of: most accurate angles from which to measure a biometric indicator (e.g. best signal quality); most efficient angles with respect to power (e.g. lowest power level required); and best angles to compensate for shifting of the device relative to the person's body (e.g. to maintain optical scanning of the same, pre-shift tissue regions and/or depths).

In an example, a wearable device can comprise a plurality of light emitters which emit light with different wavelengths and/or colors, with a repeating sequence of emitters emitting light with different wavelengths and/or colors. In an example, a wearable device can comprise a plurality of spectroscopic sensors which emit light in a selected chronological sequence and/or timing pattern. In another example, a wearable device can comprise a plurality of spectroscopic sensors which emit light of at different light-projection angles, wherein sensors which different light projection angles emit light at different times.

In an example, a wearable device can automatically change (e.g. adjust) the angle at which light beams from a spectroscopic sensor pass through body tissue in response to specific activities in which the person wearing the device is engaged (e.g. exercise, sleeping, or working). In another example, a wearable device can automatically change (e.g. adjust) the wavelength and/or color of light beams from a spectroscopic sensor which pass through body tissue in response to specific environmental conditions (e.g. temperature, humidity, ambient light intensity, or location). In an example, a wearable device can automatically change (e.g. adjust) the intensity and/or power level of light beams from a spectroscopic sensor which pass through body tissue in response to specific activities in which a person wearing the device is engaged (e.g. exercise, sleeping, or working).

In another example, a wearable device can comprise an array, grid, and/or matrix of two or more light emitters in spectroscopic sensors along a circumferential axis of the device. In an example, a wearable device can have a repeating pattern of light emitters and light receivers around an inner circumference of the device, wherein the repeating pattern is an alternating sequence of light emitters and light receivers. In an example, a wearable device can have a repeating pattern of light emitters and light receivers around an inner circumference of the device, wherein the repeating pattern is a sequence of one light emitter followed by two light receivers. In an example, a wearable device can have a repeating pattern of sets of light emitters and light receivers around an inner circumference of the device, wherein each set includes two light emitters which emit light with different light wavelengths (or colors) and one light receiver. In an example, a wearable device can have a repeating pattern of sets of light emitters and light receivers around an inner circumference of the device, wherein each set includes a plurality of light emitters which emit light with different light wavelengths (or colors) around one light receiver.

In an example, a wearable device can comprise a circumferential array of light emitters and light receivers, wherein the array includes rows of light emitters and light receivers along a line which is orthogonal to the inner circumference of the device, and wherein each row includes two light emitters and one light receiver. In another example, a wearable device can comprise a circumferential array of light emitters and light receivers, wherein the array includes rows of light emitters and light receivers along a line which is orthogonal to the inner circumference of the device, and wherein each row includes one light emitter and two light receivers.

In an example, a wearable device can comprise a two-dimensional array of spectroscopic sensors comprising: a plurality of circles of optical components around the inner circumference of the device; and a plurality of rows of optical components on the inner circumference of the device which are orthogonal to the circles; wherein each circle further comprises at least six light emitters; wherein each circle further comprises six light receivers; wherein each row further comprises at least two light emitters with different wavelengths or colors; and wherein each row further comprises at least one light receiver. In an example, a wearable device can include a two-dimensional array of spectroscopic sensors. In an example, a wearable device can include a two-dimensional array of spectroscopic sensors consisting of a plurality of circles around the inner circumference of the device and a plurality of rows on the inner circumference of the device which are orthogonal to the circles, wherein each circle further comprises a plurality of light emitters with different wavelengths (or colors) and light receivers, and wherein each row further comprises a plurality of light emitters with different wavelengths (or colors) and light receivers.

In an example, a wearable device can comprise light emitters on one side (e.g. the dorsal side) of the device and light receivers on the opposite side (e.g. the ventral side) of the device. In another example, a wearable device can automatically vary the geometric configuration of one or more light emitters and light receivers in a spectroscopic sensor in order to scan through a range of tissue depths and/or locations. In an example, a wearable device can comprise: a plurality of light emitters; a plurality of light receivers; and a plurality of actuators; wherein the actuators change (e.g. vary) the sequential order of light emitters and light receivers over time to scan through a range of tissue depths and/or locations.

In an example, a wearable device can have a plurality of light emitters which are configured in a polygonal array around a light receiver. In an example, a wearable device can have a plurality of light receivers which are configured in a circle around a light emitter. In an example, a wearable device can have a plurality of sets of light emitters and light receivers, wherein each set has four light emitters in a circle around a light receiver. In another example, a wearable device can have a plurality of sets of light emitters and light receivers, wherein each set has six light emitters in a hexagonal array around a light receiver. In an example, a wearable device can have a plurality of sets of light emitters and light receivers, wherein each set has a plurality of light emitters with different wavelengths (or colors) in a polygonal array around a light receiver. In an example, a wearable device can have a plurality of sets of light receivers and light emitters, wherein each set has a plurality of light receivers in a circle around a light emitter. In an example, a wearable device can have a plurality of sets of light receivers and light emitters, wherein each set has four light receivers in a square array around a light emitter.

In another example, a wearable device can comprise a ring or band with an expandable and/or deformable layer around a portion of its inner circumference. In an example, a wearable device can comprise: a band or ring; a first elastic member and/or deformable layer on the right side of the inner circumference of the band or ring; and a second elastic member and/or deformable layer on the left side of the inner circumference of the band or ring. In another example, a wearable device can comprise: a ring or band; a plurality of elastic members and/or deformable layers on the ring or band; and a plurality of spectroscopic sensors on the ring or band; wherein there is a separate elastic member and/or deformable layer for each spectroscopic sensor. In an example, a wearable device can comprise: a ring or band; and a layer of compressible and/or deformable foam on the inner circumference of the ring or band; and one or spectroscopic sensors on the layer of compressible and/or deformable foam.

In another example, a wearable device can comprise: a ring or band; compressible and/or deformable foam on a first portion of the inner circumference of the ring or band; and a plurality of spectroscopic sensors on a second portion of the inner circumference of the ring or band. In an example, a wearable device can include a plurality of separate elastic members and/or deformable layers on the inner circumference of a band or ring, wherein the elastic members and/or deformable layers collectively span between 20% and 60% of the inner circumference of the band or ring. In an example, an expandable member and/or deformable chamber can span the entire inner circumference of a ring or band. In an example, there can be a plurality of separate elastic members and/or deformable layers on the inner circumference of a wearable band or ring, wherein each elastic member and/or deformable layer spans between 5% and 15% of the inner circumference of the band or ring.

In an example, a wearable device can comprise a ring or band with nested (circumferential) layers or portions including an outer layer or portion (farthest from the center of the ring or band), an inner layer or portion (closest to the center of the ring or band), and a middle layer or portion between the outer layer or portion and the inner layer or portion; wherein there are a plurality of spectroscopic sensors on the inner layer or portion; and wherein the middle layer or portion is expandable. In an example, a wearable device can comprise a ring or band with nested (circumferential) layers or portions including an outer layer or portion (farthest from the center of the ring or band), an inner layer or portion (closest to the center of the ring or band), and a middle layer or portion between the outer layer or portion and the inner layer or portion; wherein there are a plurality of spectroscopic sensors on the inner layer or portion; wherein the middle layer or portion is expandable; and wherein the nested payers or portions span between 50% and 80% of the inner circumference of the ring or band.

In another example, a wearable device can comprise a ring or band with a rigid outer layer, a middle expandable (e.g. inflatable) layer, an inner (circumference-center-facing) layer, and one or more spectroscopic sensors on the inner layer. In an example, a wearable device can comprise: a finger ring; a rigid outward-facing portion of the ring; an inner circumference-center-facing portion of the ring; an inflatable middle portion of the ring, wherein the inflatable middle portion is sandwiched between the rigid outward-facing portion and the inner circumference-center-facing portion, and wherein the inner circumference-center-facing portion moves relative to the rigid outward-facing portion when the inflatable middle portion is expanded or contracted; and a spectroscopic sensor on the inner circumference-center-facing portion which is configured to record biometric data concerning the person's body tissue.

In another example, a wearable device can comprise: a ring or band; a plurality of deformable members or layers on the inner circumference of the ring or band; and a pump, wherein the deformable members or layers are filled with a flowable substance (e.g. a fluid, gel, or gas), and wherein the pump pumps the flowable substance into or out of the deformable members or layers. In an example, a wearable device can comprise: a ring or band; a plurality of expandable chambers or layers on the inner circumference of the ring or band; a plurality of spectroscopic sensors, wherein the spectroscopic sensors are on the expandable chambers or layers; and a pump, wherein the expandable chambers or layers are filled with a flowable substance (e.g. a fluid, gel, or gas), and wherein the pump pumps the flowable substance into or out of the expandable chambers or layers.

In an example, a wearable device can comprise: a ring or band; a plurality of compressible members or layers on the inner circumference of the ring or band; a plurality of spectroscopic sensors; and a pump, wherein the compressible members or layers are filled with a flowable substance (e.g. a fluid, gel, or gas), and wherein the pump pumps the flowable substance into or out of the compressible members or layers. In an example, a wearable device can comprise: a ring or band; a plurality of elastic chambers or layers on the inner circumference of the ring or band; a plurality of spectroscopic sensors; and a pump, wherein the elastic chambers or layers are filled with a flowable substance (e.g. a fluid, gel, or gas), and wherein the pump pumps the flowable substance into or out of the elastic chambers or layers.

In an example, a wearable device can comprise: a ring or band; a plurality of deformable members or layers on the inner circumference of the ring or band; a plurality of spectroscopic sensors; wherein the deformable members or layers are filled with a flowable substance (e.g. a fluid, gel, or gas). In an example, a wearable device can comprise: a ring or band; a plurality of spectroscopic sensors on an inner circumference of the ring or band, and one or more pneumatically-expandable chambers on the inner circumference of the ring or band. In an example, a wearable device can comprise: a ring or band; a plurality of light emitters on the ring or band; a plurality of light receivers on the ring or band; and a plurality of expandable components (e.g. chambers, bladders, or layers) filled with a flowable substance on the ring or band; wherein pumping the flowable substance into the expandable components decreases the inner circumference of the ring or band and thereby the fit of the device on the person's finger.

In another example, a wearable device can comprise: a ring or band; a plurality of light emitters on the ring or band; a plurality of light receivers on the ring or band; a first expandable component (e.g. expandable chamber, bladder, or layer) which is filled with a flowable substance (e.g. fluid, gel, or gas) on the ring or band, wherein changing the amount of the flowable substance in the first expandable component changes the distance between a first light emitter and a person's body; and a second expandable component (e.g. expandable chamber, bladder, or layer) which is filled with the flowable substance, wherein changing the amount of the flowable substance in the second expandable component changes the distance between a second light emitter and the person's body.

In an example, a wearable device can comprise: a ring or band; a plurality of spectroscopic sensors on the inner circumference of the ring or band; an expandable chamber or layer on the inner circumference of the ring or band, wherein the expandable chamber or layer is filled with a flowable substance (e.g. a fluid, gel, or gas); a channel through which the flowable substance can flow into, or out of, the expandable chamber or layer; and a pump which pumps the flowable substance into, or out of, the expandable chamber or layer. In another example, a wearable device can comprise: a ring or band; a plurality of spectroscopic sensors on the ring or band; an outward-facing elastic member on the ring or band which is filled with a fluid, gel, or gas; a circumference-center-facing elastic member on the ring or band which is filled with the fluid, gel, or gas; a channel through which the fluid, gel, or gas can flow from the outward-facing elastic member to the circumference-center-facing elastic member, or vice versa.

In an example, a wearable device can comprise: a ring or band; an compressible member or layer on the inner circumference of the ring or band; and a pump; wherein the compressible member or layer is filled with a flowable substance (e.g. a fluid, gel, or gas), and wherein the pump pumps the flowable substance into or out of the compressible member or layer. In an example, a wearable device can comprise: a ring or band; an expandable chamber or layer on the inner circumference of the ring or band, wherein the expandable chamber or layer is filled with a flowable substance (e.g. a fluid, gel, or gas). In an example, a wearable device can comprise: a ring or band; and a deformable member or layer on the inner circumference of the ring or band. In an example, a wearable device can comprise: a ring or band; and a deformable member or layer on the inner circumference of the ring or band, wherein the deformable member is made from foam.

In another example, a wearable device can comprise: a ring or band; an elastic chamber or layer on the inner circumference of the ring or band; and a pump; wherein the elastic chamber or layer is filled with a flowable substance (e.g. a fluid, gel, or gas), and wherein the pump pumps the flowable substance into or out of the elastic chamber or layer. In an example, a wearable device can comprise: a ring or band; and a plurality of compressible members or layers on the inner circumference of the ring or band, wherein the compressible members are filled with a flowable substance (e.g. a fluid, gel, or gas). In an example, a wearable device can comprise: a ring or band; and a plurality of expandable chambers or layers on the inner circumference of the ring or band, wherein the expandable chambers or layers are filled with a flowable substance (e.g. a fluid, gel, or gas).

In an example, a wearable device can comprise: a ring or band; and a plurality of deformable members or layers on the inner circumference of the ring or band, wherein the deformable members are made from foam. In another example, a wearable device can comprise: a ring or band; an expandable chamber or layer on the inner circumference of the ring or band, wherein the expandable chamber or layer is filled with a flowable substance (e.g. a fluid, gel, or gas); a channel through which the followable substance can flow into, or out of, the expandable chamber or layer; and a plurality of spectroscopic sensors on the expandable chamber or layer.

In an example, a wearable device can comprise: a ring or band; biometric sensor on the ring or band; an outer-circumference elastic chamber on the ring or band; an inner-circumference elastic chamber on the ring or band; a channel between the outer-circumference elastic chamber and the inner-circumference elastic chamber; and a pump which pumps a flowable substance through the channel to change the fit of the ring or band and/or change the distance and/or pressure between the biometric sensors and the person's body. In an example, a wearable device can have an expandable component (e.g. an expandable chamber, bladder, or layer) which is filled with a flowable substance, wherein changing the amount of the flowable substance in the expandable component pushes (or pulls) a light emitter and/or a light receiver closer to (or farther away from) the surface of a person's body.

In an example, a finger ring can comprise a flexible (e.g. elastic, stretchable, and/or articulated) segment on the dorsal side of the finger ring, a rigid (e.g. inelastic and/or inflexible) segment on the ventral side of the finger ring, and one or more spectroscopic sensors on the flexible portion. In another example, a finger ring can comprise a flexible (e.g. elastic, stretchable, or articulated) portion, a rigid (e.g. inflexible) portion, and one or more spectroscopic sensors, wherein the flexible portion is located between the 270-degree and 0-degree polar coordinates. In an example, a finger ring can comprise an articulated portion, a rigid portion, and one or more spectroscopic sensors, wherein the articulated portion spans between 5% and 25% of the circumference of the finger ring.

In an example, a finger ring can comprise two flexible (e.g. elastic, stretchable, or articulated) portions, a rigid (e.g. inflexible) portion, and one or more spectroscopic sensors, wherein a first flexible portion is located between the 270-degree and 0-degree polar coordinates, and wherein a second flexible portion is located between the 0-degree and 90-degree polar coordinates. In an example, a ring or band can comprise a circumferential sequence of alternating rigid (e.g. inflexible and/or inelastic) and flexible (e.g. elastic, stretchable, and/or articulated) sections which collectively span the circumference of the ring or band, wherein there are at least two rigid sections and at least two flexible sections.

In another example, a wearable device can comprise: a first flexible (e.g. elastic, stretchable, and/or articulated) section of a ring or band which spans between 10% and 25% of the circumference of a person's finger; a second flexible section of the ring or band which spans between 10% and 25% of the circumference of the person's finger; a first rigid (e.g. inelastic and/or inflexible) section of the ring or band which spans between 25% and 50% of the circumference of the person's finger; a second rigid section of the ring or band which spans between 25% and 50% of the circumference of the person's finger; and a plurality of spectroscopic sensors on the inner circumference of the ring or band. In an example, a wearable device can comprise: a flexible (e.g. elastic, stretchable, and/or articulated) section of a ring or band which spans between 10% and 25% of the circumference of a person's finger; a rigid (e.g. inelastic and/or inflexible) section of the ring or band which spans the rest of the circumference of the person's finger; and a plurality of spectroscopic sensors on the inner circumference of the ring or band.

In another example, a finger ring can comprise: an outer rigid band which encircles a person's finger; and an inner elastic (e.g. stretchable) band whose ends are attached to the inner circumference of the rigid band, wherein the inner elastic band spans between 20% and 50% of the inner circumference of the rigid band. In an example, a finger ring can comprise: an outer rigid band which encircles a person's finger; an inner elastic band whose ends are attached to the inner circumference of the rigid band; and a plurality of spectroscopic sensors which are on the inner elastic band. In another example, a finger ring can comprise: an outer rigid band which encircles a person's finger; and an inner elastic (e.g. stretchable) band whose ends are attached to the inner circumference of the rigid band, wherein the inner elastic band spans a portion of the ventral half of the inner circumference. In an example, a wearable device can comprise: an outer inelastic (e.g. rigid and/or inflexible) band which spans the circumference of a portion of a person's body (e.g. wrist or finger) and an inner elastic (e.g. stretchable and/or deformable) band which spans only a portion of this circumference.

In an example, a ring or band can have a circumferential shape with a plurality of inward-facing undulations. In an example, a ring or band can have inward (e.g. center) facing undulations, waves, and/or protrusions around its inner circumference and a plurality of spectroscopic sensors which collect data concerning body tissue, wherein spectroscopic sensors are located on the most proximal (e.g. most inward) portions of undulations, waves, and/or protrusions. In an example, the interior circumference of a ring or band can have a plurality of inward (e.g. center) facing undulations and/or protrusions. In an example, the interior circumference of a ring or band can have eight inward (e.g. center) facing undulations and/or protrusions.

In an example, a wearable device can be a watch band. In an example, changes in light characteristics such as its spectral distribution which are caused by transmission of the light through body tissue can be analyzed to estimate the values of biometric parameters and/or to identify physiological conditions. In an example, a wearable device can comprise an array, grid, and/or matrix of light receivers which differ in: location and/or distance from a light emitter in a spectroscopic sensor; and/or distance to the surface of a person's body. In an example, a light emitter in a spectroscopic sensor can be a Light Emitting Diode (LED). In another example, a light emitter in a spectroscopic sensor can be a white-light laser. In an example, a light emitter in a spectroscopic sensor can emit infrared or near-infrared light. In another example, a light emitter in a spectroscopic sensor can emit ultraviolet light.

In an example, a wearable device can comprise: a first light emitter wherein light from this emitter reflects primarily from a first tissue depth, breadth, and/or location; and a second light emitter wherein light from this emitter reflects primarily from a second tissue depth, breadth, and/or location. In an example, a wearable device can comprise: a first spectroscopic sensor which is configured to project a beam of light with a first wavelength and/or color into finger tissue at a first angle; and a second spectroscopic sensor which is configured to project a beam of light with a second wavelength and/or color into finger tissue at a second angle, wherein the first angle differs from the second angle by at least 10 degrees. In an example, a wearable device can comprise: one or more light emitters on the dorsal side of a ring or band; and one or more light receivers on the ventral side of the ring or band. In an example, a wearable device can include a plurality of light emitters around the inner circumference of the device, wherein the angles at which the light emitters emit light into body tissue varies as a function of the polar and/or radial coordinate of the emitters on the inner circumference of the device.

In an example, a wearable device can comprise a plurality of spectroscopic sensors (including light emitters and light receivers), wherein the angles at which light beams from the sensors are projected into body tissue are changed over time to measure different biometric parameters. In an example, a wearable device can comprise a plurality of spectroscopic sensors (including light emitters and light receivers), wherein the angles at which light beams from the sensors are projected into body tissue are changed over time to identify the optimal angle or angles for measuring biometric indicators. In an example, a wearable device can include a micromirror which changes the projection and/or body incidence angle of a light beam emitted by a light emitter in a spectroscopic sensor. In an example, the depth, breadth, location, and/or type of body tissue through which light from a spectroscopic sensor is transmitted can be changed by adjusting the angle of light emitted from a light emitter in the spectroscopic sensor.

In another example, a wearable device can comprise one or more rotating and/or pivoting light receivers. In an example, a wearable device can comprise one or more rotating and/or pivoting light receivers which are rotated and/or pivoted in an iterative, oscillating, and/or sinusoidal manner. In another example, a wearable device can comprise: a band or ring which spans the circumference of a portion of a person's body; an enclosure which is part of the attachment member; and a rotating and/or pivoting light-projecting spectroscopic sensor, wherein this sensor is rotated and/or pivoted relative to the enclosure, and wherein rotation and/or pivoting of this sensor relative to the enclosure changes the angle at which the sensor projects light into a portion of a person's body. In an example, a wearable device can include a spectroscopic sensor at a fixed location on the inner circumference of the device which scans different regions and/or depths of body tissue as the angle at which it projects light into the body is changed in an iterative, oscillating, and/or sinusoidal manner.

In another example, a wearable device can comprise a rotating and/or pivoting ball on the inner circumference of the device; and a light emitter on the ball, wherein rotation and/or pivoting of the ball changes the angle, tissue depth, and/or tissue region at which a light beam from the light emitter passes through a person's body tissue. In an example, a wearable device can comprise: a finger ring; a moving (e.g. rotating and/or pivoting) ball; and a spectroscopic sensor which is part of (or attached to) the rotating ball. In an example, a wearable device can comprise: a finger ring; a rotating and/or pivoting ball (e.g. spherical component) on the inner circumference of the finger ring; and a spectroscopic sensor on the ball, wherein rotation and/or pivoting of the ball changes the angles at which light from the spectroscopic sensor is transmitted through a person's finger, thereby scanning different tissue regions and/or tissue depths in the person's finger.

In an example, a wearable device can comprise: a ring or band; a plurality of rotating and/or pivoting balls (e.g. spherical components) on the ring or band; and a plurality of spectroscopic sensors on the balls, wherein rotation and/or pivoting of the balls changes the angles at which light beams from the spectroscopic sensors are transmitted through tissue of the portion of the person's body. In an example, a wearable device can include a light-projecting spectroscopic sensor on a rotating and/or pivoting ball. In an example, a wearable device can include a rotating and/or pivoting ball (e.g. spherical component) to which a spectroscopic sensor is attached on the dorsal side of the device.

In an example, a wearable device can comprise: a first actuator which rotates and/or pivots a light emitter; and a second actuator which rotates and/or pivots a light receiver, thereby changing the angle at which light from the light emitter is transmitted through body tissue and the angle at which light this light is received by the light receiver after transmission through body tissue, wherein the first and second actuators can be moved independently of each other. In an example, a wearable device can comprise: a movable component; a spectroscopic sensor attached to the moveable component; and an electromagnetic actuator, wherein the angle at which light from the spectroscopic sensor is transmitted through body tissue is changed by rotation and/or pivoting of the moveable component by the electromagnetic actuator.

In another example, a wearable device can comprise: a spectroscopic sensor; a prism, lens, or filter which redirects light from the spectroscopic sensor; and an electromagnetic actuator, wherein the angle at which light from the spectroscopic sensor is transmitted through body tissue is changed by movement of the prism, lens, or filter by the electromagnetic actuator. In an example, a wearable device can have a plurality of actuators and a plurality of spectroscopic sensors, wherein the angles at which light from light emitters in the spectroscopic sensors goes through body tissue can be changed by movement (e.g. rotation and/or pivoting) of the actuators. In another example, a wearable device can have a plurality of actuators and a plurality of spectroscopic sensors, wherein the angles at which light beams from spectroscopic sensors are transmitted through body tissue can be selectively, individually, and/or independently changed by the actuators.

In an example, a wearable device can comprise: a plurality of light emitters; a plurality of light receivers; a plurality of actuators; and a plurality of movable light reflectors (e.g. movable micromirrors); wherein movement of the light reflectors by the actuators changes the angles at which light rays from the light emitters pass through body tissue and/or the angles at which light rays from body tissue are received by light receivers. In another example, a wearable device can comprise: a plurality of spectroscopic sensors; a plurality of actuators; and a plurality of movable light reflectors (e.g. movable micromirrors); wherein movement of the light reflectors by the actuators changes the tissue depths and/or tissue regions which are scanned by the spectroscopic sensors.

In an example, a wearable device can comprise a plurality of light emitters and a plurality of microprisms, wherein the projection angles of light beams from the light emitters can be individually redirected (e.g. refracted) by individual microprisms. In an example, a wearable device can comprise: a spectroscopic sensor (e.g. light emitter and light receiver); a refractive component (e.g. prism, lens, or optical filter); and an actuator; wherein the angle at which light from the spectroscopic sensor passes through body tissue is changed by movement (e.g. rotation and/or pivoting) of the refractive component by the actuator.

In an example, a wearable device can comprise: a finger ring; a track or channel around the inner circumference of the finger ring; and one or more spectroscopic sensors which slide around the track or channel to different radial locations on the inner circumference of the finger ring. In an example, a wearable device can comprise: a ring or band; a plurality of actuators; a plurality of light emitters on the inner circumference of the ring or band; and a plurality of light receivers on the inner circumference of the ring or band; wherein the actuators change the radial (e.g. polar coordinate, compass, or clock-hour) locations of the light emitters and/or the light receivers on the inner circumference of the ring or band.

In an example, a wearable device can comprise: one or more light emitters; one or more light receivers; a first set of one or more actuators, wherein the first set or one or more actuators change the radial locations of the one or more light emitters on the circumference of the device; and a second set or one or more actuators, wherein the second set or one or more actuators change the radial locations of the one or more light receivers on the circumference of the device. In an example, a wearable device can include actuators which move (e.g. slide) spectroscopic sensors to different radial (e.g. polar coordinate, compass, or clock-hour) locations around the inner circumference of the device. In another example, a wearable device can include actuators which move (e.g. slide) light emitters and/or light receivers along a circumferential track (or channel) to different radial (e.g. polar coordinate, compass, or clock-hour) locations around the inner circumference of the device. In an example, wearable device can be a band or ring with an inner circumferential track (or channel) along which one or more spectroscopic sensors move (e.g. slide), when one or more spectroscopic sensors are manually moved along the track (or channel).

In another example, a ring or band can have a repeating sequence of light emitters and light receivers around (a portion of) the inner circumference of the ring or band. In an example, a ring or band can have a repeating sequence of two light emitters of different wavelengths and a light receiver around (a portion of) the inner circumference of the ring or band. In another example, a ring or band can have a series of spectroscopic sensors which are evenly distributed around a portion of the inner circumference of the ring or band, wherein this portion is between 30% and 60% of the total inner circumference of the ring or band. In an example, a ring or band can have an alternating sequent of light emitters and light receivers which spans between 20% and 45% of the inner circumference of the ring or band. In an example, a wearable device can comprise: a ring or band; a first spectroscopic sensor at a first radial location on the inner circumference of the ring or band; and a second spectroscopic sensor at a second radial location on the inner circumference of the ring or band, wherein the spectroscopic sensors record biometric data concerning the person's body tissue.

In an example, a wearable device can comprise actuators and spectroscopic sensors, wherein the actuators can individually and independently change (e.g. adjust) the distances between the sensors and the surface of a person's body, and wherein distance adjustment can be used to place sensors at different distances for (sequentially) emitting light with different wavelengths and/or colors. In an example, a wearable device can comprise light receivers and actuators, wherein the actuators can individually and independently change (e.g. adjust) the distances and/or pressures between the light emitters and the surface of a person's body. In an example, a wearable device can have a first actuator which changes the distance between a light emitter and the surface of a portion of a person's body and a second actuator which changes the distance between a light receiver and the surface of the person's body.

In an example, a wearable device can comprise: a plurality of light emitters; a plurality of light receivers; and a plurality of actuators; wherein the actuators automatically change (e.g. adjust) the distances between the light emitters and the light receivers to scan different tissue depths and/or regions. In another example, a wearable device can comprise: one or more light emitters; one or more light receivers; and one or more actuators; wherein an actuator automatically changes (e.g. adjusts) the distance between a light emitter and a light receiver. In an example, a wearable device can have one or more electromagnetic solenoids which move spectroscopic sensors, including one or more light emitters and/or light receivers. In another example, a wearable device can have one or more expandable chambers which move spectroscopic sensors, including one or more light emitters and/or light receivers. In an example, a wearable device can have one or more piston-type actuators which move spectroscopic sensors, including one or more light emitters and/or light receivers. In an example, a wearable device can have one or more telescoping actuators which move spectroscopic sensors, including one or more light emitters and/or light receivers.

In an example, a wearable device can have at least 24 light emitters and light receivers, including at least six light emitters in each of following four wavelengths and/or colors: near-infrared; infrared; red; and green. In an example, a wearable device can have light emitters which project light with different wavelengths and/or colors into body tissue, wherein light emitters with different wavelengths and/or colors project light into body tissue at different angles, and wherein the projection angles of these emitters are a function of the wavelengths and/or frequencies of their light emissions. In an example, light emitters which emit light with different wavelengths and/or colors can be configured to emit light into body tissue at different angles relative to the surface of a person's body.

In an example, a wearable device can further comprise one or more optical filters or lenses which change the wavelength, color, and/or spectrum of light emitted by a light emitter in a spectroscopic sensor. In an example, a wearable device can include one or more light emitters which emit light whose wavelengths and/or colors change over time to measure different types of biometric indicators. In another example, the depth, breadth, location, and/or type of body tissue from which light from a light emitter in a spectroscopic sensor is reflected can be changed by adjusting the wavelength, color, and/or spectrum of light emitted from the light emitter. In an example, the wavelength, color, and/or spectrum of light from a light emitter can be changed over time to create a chronological sequence of light with different wavelengths, colors, and/or spectra.

In another example, the depth, breadth, location, and/or type of body tissue scanned by a light emitter on a wearable device can be changed (e.g. adjusted) by changing (e.g. adjusting) the power and/or intensity of light emitted from the light emitter. In an example a wearable device can comprise: a first light emitter in a spectroscopic sensor which emits light with a first light coherence, polarization, and/or phase; and a second light emitter in a spectroscopic sensor which emits light with a second light coherence, polarization, and/or phase.

In an example, a wearable device can comprise: a device (e.g. ring or band) which is configured to be worn around a portion of a person's body (e.g. finger or wrist); one or more light emitters on the device; one or more light receivers on the device; and one or more actuators on the device; wherein the one or more actuators change light-projection angles (e.g. the angles at which light beams projected from the light emitters are transmitted through body tissue) and/or light-reception angles (e.g. the angles at which light from body tissue is received by the light receivers); and wherein optimal light-projection angles and/or light reception angles are selected based on one or more criteria selected from the group consisting of: most accurate angles from which to measure a biometric indicator (e.g. best signal quality); most efficient angles with respect to power (e.g. lowest power level required); and best angles to compensate for shifting of the device relative to the person's body (e.g. to maintain optical scanning of the same, pre-shift tissue regions and/or depths).

In another example, a wearable device can comprise a plurality of light emitters which emit light in a selected chronological sequence and/or timing pattern. In an example, a wearable device can comprise a plurality of light emitters which emit light of at different light-projection angles, wherein emitters which different light projection angles emit light at different times. In an example, a wearable device can comprise a plurality of spectroscopic sensors which emit light of different wavelengths and/or colors, wherein sensors which different wavelengths and/or colors emit light at different times. In an example, a wearable device can comprise a plurality of spectroscopic sensors which emit light with different light-projection angles, with a repeating sequence of sensors emitting light with different light-projection angles.

In an example, a wearable device can automatically change (e.g. adjust) the distance and/or pressure between a spectroscopic sensor and the surface of a person's body in response to specific environmental conditions (e.g. temperature, humidity, ambient light intensity, or location). In an example, a wearable device can automatically change (e.g. adjust) the wavelength and/or color of light beams from a spectroscopic sensor which pass through body tissue in response to specific activities in which a person wearing the device is engaged (e.g. exercise, sleeping, or working). In an example, a wearable device can automatically change (e.g. adjust) the projection angle and wavelength (e.g. color) of light beams from a spectroscopic sensor in response to specific environmental conditions (e.g. temperature, humidity, ambient light intensity, or location).

In another example, a wearable device can comprise an array, grid, and/or matrix of two or more light emitters in spectroscopic sensors along a proximal-to-distal axis of the device. In an example, a wearable device can have a repeating pattern of light emitters and light receivers around an inner circumference of the device, wherein the repeating pattern is a sequence of two light emitters followed by one light receiver. In another example, a wearable device can have a repeating pattern of sets of light emitters and light receivers around an inner circumference of the device, wherein each set includes one light emitter and one light receiver. In another example, a wearable device can have a repeating pattern of sets of light emitters and light receivers around an inner circumference of the device, wherein each set includes three light emitters which emit light with different light wavelengths (or colors) and one light receiver. In an example, a wearable device can have a repeating pattern of sets of light emitters and light receivers around an inner circumference of the device, wherein each set includes a plurality of light receivers around one light emitter.

In an example, a wearable device can comprise a circumferential array of light emitters and light receivers, wherein the array includes rows of light emitters and light receivers along a line which is orthogonal to the inner circumference of the device, and wherein each row includes two light emitters of different wavelengths (or colors) and one light receiver. In an example, a wearable device can comprise a circumferential array of light emitters and light receivers, wherein the array includes rows of light emitters and light receivers along a line which is orthogonal to the inner circumference of the device, and wherein each row includes one light emitter and three light receivers.

In an example, a wearable device can comprise: an enclosure; and a two-dimensional spectroscopic sensor array which is part of (or on) the enclosure, wherein spectroscopic sensors in this two-dimensional array differ in location along a portion of the circumference of the device, and wherein spectroscopic sensors in this two-dimensional array differ in location along axes which are perpendicular to the circumference of the device. In an example, a wearable device can include a two-dimensional array of spectroscopic sensors consisting of a plurality of circles around the inner circumference of the device and a plurality of rows on the inner circumference of the device which are orthogonal to the circles.

In an example, a wearable device can comprise a plurality of pairs of light emitters and light receivers, wherein a light emitter and a light receiver in a pair are on diametrically-opposite sides (e.g. 180 degrees difference) of the inner circumference of the device. In an example, a wearable device can comprise light emitters on one side (e.g. the ventral side) of the device and light receivers on the opposite side (e.g. the dorsal side) of the device. In another example, a wearable device can comprise: a plurality of light emitters; a plurality of light receivers; and a plurality of actuators; wherein the actuators change (e.g. vary) the distances between light emitters and light receivers over time in order to scan through a range of tissue depths and/or locations.

In an example, a wearable device can have a checkerboard array of light emitters and light receivers, wherein light emitters correspond to white squares on a checkerboard and light receivers correspond to black squares on the checkerboard. In another example, a wearable device can have a plurality of light emitters of different wavelengths (or colors) which are configured in a circle around a light receiver. In an example, a wearable device can have a plurality of light receivers which are configured in a polygonal array around a light emitter. In an example, a wearable device can have a plurality of sets of light emitters and light receivers, wherein each set has a plurality of light emitters in a polygonal array around a light receiver. In an example, a wearable device can have a plurality of sets of light emitters and light receivers, wherein each set has a plurality of light emitters with different wavelengths (or colors) in a circle around a light receiver.

In an example, a wearable device can have a plurality of sets of light emitters and light receivers, wherein each set has four light emitters with different wavelengths (or colors) in a square array around a light receiver. In an example, a wearable device can have a plurality of sets of light receivers and light emitters, wherein each set has four light receivers in a circle around a light emitter. In another example, a wearable device can have a plurality of sets of light receivers and light emitters, wherein each set has six light receivers in a hexagonal array around a light emitter.

In an example, a wearable device can comprise a ring or band with an expandable and/or deformable layer around a portion of its inner circumference, wherein this portion is between 40% and 70% of the circumference of the ring or band. In another example, a wearable device can comprise: a finger ring; an enclosure which is part of the ring; a deformable chamber filled with a fluid, gel, or gas which is attached to (or part of) the enclosure; and a spectroscopic sensor which is configured to record biometric data concerning the person's body tissue, wherein this sensor is on a circumference-center-facing side of the deformable chamber.

In an example, a wearable device can comprise: a ring or band; a plurality of elastic members and/or deformable layers on the ring or band; and a plurality of spectroscopic sensors on elastic members and/or deformable layers; wherein there is a separate elastic member and/or deformable layer for each spectroscopic sensor. In another example, a wearable device can comprise: a ring or band; and a layer of compressible and/or deformable foam on a portion of the inner circumference of the ring or band; and a plurality of spectroscopic sensors. In an example, a wearable device can comprise: a ring or band; compressible and/or deformable foam on a first portion of the inner circumference of the ring or band; and a plurality of spectroscopic sensors on a second portion of the inner circumference of the ring or band, wherein the second portion is diametrically-opposite the first portion.

In an example, an elastic member and/or deformable layer can span between 20% and 60% of the inner circumference of wearable band or ring. In an example, there can be a plurality of biometric sensors on a center-facing side of an elastic member and/or deformable layer on the interior circumference of a band or ring, wherein the elastic member and/or deformable layer is filled with a flowable substance (e.g. a liquid, gel, or gas). In an example, there can be one continuous elastic member and/or deformable layer on the inner circumference of a wearable band or ring.

In an example, a wearable device can comprise a ring or band with nested (circumferential) layers or portions including an outer layer or portion (farthest from the center of the ring or band), an inner layer or portion (closest to the center of the ring or band), and a middle layer or portion between the outer layer or portion and the inner layer or portion; wherein there are a plurality of spectroscopic sensors on the inner layer or portion; wherein the middle layer or portion is filled with a flowable substance (e.g. a liquid, gel, or gas); and wherein middle layer or portion is expanded by pumping the flowable substance into it. In an example, a wearable device can comprise a ring or band with nested (circumferential) layers or portions including an outer layer or portion (farthest from the center of the ring or band), an inner layer or portion (closest to the center of the ring or band), and a middle layer or portion between the outer layer or portion and the inner layer or portion; wherein there are a plurality of spectroscopic sensors on the inner layer or portion; and wherein middle layer or portion is expanded by the application of electrical energy.

In another example, a wearable device can comprise: a band or ring; a rigid outward-facing portion of the band or ring; an inner circumference-center-facing portion of the band or ring; an expandable (e.g. inflatable) middle portion of the band or ring which is sandwiched between the rigid outward-facing portion and the inner circumference-center-facing portion; and a spectroscopic sensor on the inner circumference-center-facing portion of the enclosure. In an example, a wearable device can comprise: a ring or band; a plurality of compressible members or layers on the inner circumference of the ring or band; and a pump, wherein the compressible members or layers are filled with a flowable substance (e.g. a fluid, gel, or gas), and wherein the pump pumps the flowable substance into or out of the compressible members or layers.

In another example, a wearable device can comprise: a ring or band; a plurality of elastic chambers or layers on the inner circumference of the ring or band; and a pump, wherein the elastic chambers or layers are filled with a flowable substance (e.g. a fluid, gel, or gas), and wherein the pump pumps the flowable substance into or out of the elastic chambers or layers. In an example, a wearable device can comprise: a ring or band; a plurality of deformable members or layers on the inner circumference of the ring or band; a plurality of spectroscopic sensors, wherein the spectroscopic sensors are on the deformable members or layers; and a pump, wherein the deformable members or layers are filled with a flowable substance (e.g. a fluid, gel, or gas), and wherein the pump pumps the flowable substance into or out of the deformable members or layers.

In another example, a wearable device can comprise: a ring or band; a plurality of expandable chambers or layers on the inner circumference of the ring or band; a plurality of spectroscopic sensors; and a pump, wherein the expandable chambers or layers are filled with a flowable substance (e.g. a fluid, gel, or gas), and wherein the pump pumps the flowable substance into or out of the expandable chambers or layers. In an example, a wearable device can comprise: a ring or band; a plurality of compressible members or layers on the inner circumference of the ring or band; a plurality of spectroscopic sensors; wherein the compressible members or layers are filled with a flowable substance (e.g. a fluid, gel, or gas).

In an example, a wearable device can comprise: a ring or band; a plurality of elastic chambers or layers on the inner circumference of the ring or band; a plurality of spectroscopic sensors; wherein the elastic chambers or layers are filled with a flowable substance (e.g. a fluid, gel, or gas). In an example, a wearable device can comprise: a ring or band; a plurality of spectroscopic sensors on an inner circumference of the ring or band, and one or more hydraulically-expandable chambers on the inner circumference of the ring or band. In an example, a wearable device can comprise: a ring or band; a plurality of light emitters on the ring or band; a plurality of light receivers on the ring or band; and a plurality of expandable components (e.g. chambers, bladders, or layers) filled with a flowable substance on the ring or band; wherein pumping the flowable substance into the expandable components pushes the light emitters closer to the person's finger.

In another example, a wearable device can comprise: a ring or band; a plurality of light emitters on the ring or band; a plurality of light receivers on the ring or band; a first expandable component (e.g. expandable chamber, bladder, or layer) which is filled with a flowable substance (e.g. fluid, gel, or gas) on the ring or band, wherein changing the amount of the flowable substance in the first expandable component changes the distance between one or more light emitters and a person's body; and a second expandable component (e.g. expandable chamber, bladder, or layer) which is filled with the flowable substance, wherein changing the amount of the flowable substance in the second expandable component changes the distance between one or more light receivers and the person's body.

In an example, a wearable device can comprise: a ring or band; a plurality of spectroscopic sensors on the inner circumference of the ring or band; an expandable chamber or layer on the inner circumference of the ring or band, wherein the expandable chamber or layer is filled with a flowable substance (e.g. a fluid, gel, or gas); a channel through which the flowable substance can flow into, or out of, the expandable chamber or layer; and a pump which pumps the flowable substance into, or out of, the expandable chamber or layer; wherein pumping the flowable substance into the expandable chamber or layer decreases the distance between the spectroscopic sensors and a person's body; and wherein pumping the flowable substance out from the expandable chamber or layer increases the distance between the spectroscopic sensors and the person's body. In another example, a wearable device can comprise: a ring or band; and a compressible member or layer on the inner circumference of the ring or band.

In an example, a wearable device can comprise: a ring or band; and a compressible member or layer on the inner circumference of the ring or band, wherein the compressible member is made from foam. In an example, a wearable device can comprise: a ring or band; an expandable chamber or layer on the inner circumference of the ring or band; and a pump; wherein the expandable chamber or layer is filled with a flowable substance (e.g. a fluid, gel, or gas), and wherein the pump pumps the flowable substance into or out of the expandable chamber or layer. In an example, a wearable device can comprise: a ring or band; and a deformable member or layer on the inner circumference of the ring or band, wherein the deformable member is filled with a flowable substance (e.g. a fluid, gel, or gas). In an example, a wearable device can comprise: a ring or band; and an elastic chamber or layer on the inner circumference of the ring or band.

In an example, a wearable device can comprise: a ring or band; and an elastic chamber or layer on the inner circumference of the ring or band, wherein the deformable member is made from foam. In another example, a wearable device can comprise: a ring or band; and a plurality of compressible members or layers on the inner circumference of the ring or band, wherein the compressible members are made from foam. In an example, a wearable device can comprise: a ring or band; and a plurality of deformable members or layers on the inner circumference of the ring or band. In another example, a wearable device can comprise: a ring or band; and a plurality of elastic chambers or layers on the inner circumference of the ring or band. In an example, a wearable device can comprise: a ring or band; an outward-facing elastic member on the ring or band which is filled with a fluid, gel, or gas; a circumference-center-facing elastic member on the ring or band which is filled with the fluid, gel, or gas; a channel through which the fluid, gel, or gas can flow from the outward-facing elastic member to the circumference-center-facing elastic member, or vice versa.

In an example, a wearable device can comprise: a ring or band; one or more outward-facing elastic members which are filled with a flowable substance (e.g. fluid, gel, or gas) on the ring or band; one or more circumference-center-facing elastic members which are filled with the flowable substance on the ring or band; one or more channels through which the flowable substance can flow from an outward-facing elastic member to a circumference-center-facing elastic member, or vice versa; and one or more spectroscopic sensors on a circumference-center-facing side of a circumference-center-facing elastic member. In an example, a wearable device can have an expandable component (e.g. an expandable chamber, bladder, or layer) which is filled with a flowable substance, wherein pumping the flowable substance into (or out of) the expandable component moves a light emitter and/or a light receiver closer to (or farther away from) the surface of a person's body.

In an example, a band or ring can comprise one elastic (e.g. stretchable, articulated, and/or flexible) segment and two inelastic (e.g. rigid and/or inflexible) segments. In an example, a finger ring can comprise a flexible (e.g. elastic, stretchable, and/or articulated) segment on the ventral side of the finger ring, a rigid (e.g. inelastic and/or inflexible) segment on the dorsal side of the finger ring, and one or more spectroscopic sensors on the rigid portion. In an example, a finger ring can comprise a flexible (e.g. elastic, stretchable, or articulated) portion, a rigid portion, and one or more spectroscopic sensors, wherein the flexible portion spans between 5% and 25% of the circumference of the finger ring. In an example, a finger ring can comprise an elastic (e.g. elastic, stretchable, or articulated) portion, a rigid (e.g. inelastic and/or inflexible) portion, and one or more spectroscopic sensors, wherein the flexible portion spans between 5% and 25% of the circumference of the finger ring.

In another example, a ring or band can comprise a circumferential sequence of alternating rigid (e.g. inflexible and/or inelastic) and flexible (e.g. elastic, stretchable, and/or articulated) sections which collectively span the circumference of the ring or band. In an example, a wearable device can comprise: a first flexible (e.g. elastic, stretchable, and/or articulated) section of a ring or band on the right side of (the circumference of) a person's finger; a second flexible section of the ring or band on the left side of the (circumference of) the person's finger; a first rigid (e.g. inelastic and/or inflexible) section of the ring or band on the dorsal side of (the circumference of) the person's finger; a second rigid section of the ring or band on the ventral side of (the circumference of) the person's finger; and a plurality of spectroscopic sensors on the inner circumference of the ring or band.

In another example, a wearable device can comprise: a flexible (e.g. elastic, stretchable, and/or articulated) section of a ring or band on the right side of (the circumference of) a person's finger; a rigid (e.g. inelastic and/or inflexible) section of the ring or band on the left side of (the circumference of) the person's finger; and a plurality of spectroscopic sensors on the inner circumference of the ring or band. In an example, a wearable device can comprise: a flexible (e.g. elastic, stretchable, and/or articulated) section of a ring or band which spans between 20% and 45% of the circumference of a person's finger; a rigid (e.g. inelastic and/or inflexible) section of the ring or band which spans the rest of the circumference of the person's finger; and a plurality of spectroscopic sensors on the inner circumference of the ring or band.

In an example, a finger ring can comprise: an outer rigid band which encircles a person's finger; and an inner elastic (e.g. stretchable) band whose ends are attached to the inner circumference of the rigid band, wherein the inner elastic band spans between 40% and 80% of the inner circumference of the rigid band. In another example, a finger ring can comprise: an outer rigid band which encircles a person's finger; an inner elastic band whose ends are attached to the inner circumference of the rigid band; and a plurality of spectroscopic sensors which are on the opposite side of the inner circumference from the inner elastic band.

In an example, a wearable device can comprise: an outer inelastic band with a first arcuate (e.g. circumferential) length and a first elasticity level; an inner elastic band with a second arcuate (e.g. partially-circumferential) length and a second elasticity level, wherein the inner elastic band is located on the concave side of the outer elastic band, wherein the second length is less than the first length, and wherein the second elasticity level is greater than the first elasticity level; and a plurality of spectroscopic sensors. In an example, a wearable device can comprise: an outer inelastic (e.g. rigid and/or inflexible) band which spans the circumference of a portion of a person's body (e.g. wrist or finger) and a semi-circular inner elastic (e.g. stretchable and/or deformable) band which spans approximately half of the circumference of the portion of the person's body.

In an example, a ring or band can have an undulating circumferential shape. In another example, a wearable device can comprise: a circumferentially-undulating ring or band, a first spectroscopic sensor at the proximal (most center-facing) portion of a first undulation, wave, and/or protrusion in the circumferentially-undulating band, and a second spectroscopic sensor at the proximal (most center-facing) portion of a second undulation, wave, and/or protrusion in the circumferentially-undulating band. In an example, the interior circumference of a ring or band can have a plurality of inward (e.g. center) facing sinusoidal undulations and/or protrusions. In an example, the interior circumference of a ring or band can have a plurality of inward (e.g. center) facing sinusoidal undulations and/or protrusions, wherein there are spectroscopic sensors on the undulations or protrusions.

FIG. 1 shows an example of a wearable device with a plurality of close-fitting biometric sensors. In an example, a biometric sensor can be a spectroscopic sensor which comprises a light emitter and a light receiver. In an spectroscopic sensor, a light emitter emits light into body tissue and a light receiver receives this light after the light has been transmitted through (and/or been reflected by) body tissue. Changes in light characteristics such as its spectral distribution which are caused by transmission of the light through body tissue are then analyzed to estimate the values of biometric parameters and/or to identify physiological conditions.

In FIG. 1, a series of biometric sensors are evenly distributed around the circumference-center-facing surface (e.g. the inner circumference) of a wearable band. In another example, biometric sensors can be distributed around only a portion (e.g. between 40% and 70%) of the circumference-center-facing surface (e.g. the inner circumference) of a wearable band. In examples throughout this disclosure, the word "ring" can be substituted for the word "band" and it is to be understood that these designs can be applied to either finger ring or a wrist band.

FIG. 1 shows this device from a side perspective, as it would appear encircling a lateral cross-section of a portion of a person's body such as a finger or wrist. This device is an example of an arcuate wearable ring or band with a circumferentially-distributed array of biometric sensors. The example shown in FIG. 1 can be described as a wearable device with a plurality of close-fitting biometric sensors comprising: an attachment member (such as a ring or band) which is configured to span the circumference of a portion of a person's body; an enclosure which is part of the attachment member; a first biometric sensor at a first location on the enclosure which records biometric data concerning the person's body tissue; and a second biometric sensor at a second location on the enclosure which records biometric data concerning the person's body tissue.

In an example, an attachment member or band can be a finger ring. In an example, a biometric sensor can be a spectroscopic sensor which further comprises a light emitter and a light receiver. In this case, the example shown in FIG. 1 can be described as a wearable device with a plurality of close-fitting spectroscopic sensors comprising: a finger ring; an enclosure which is part of the ring; a first spectroscopic sensor at a first location in or on the enclosure which records biometric data concerning the person's body tissue; and a second spectroscopic sensor at a second location in or on the enclosure which records biometric data concerning the person's body tissue.

The example shown in FIG. 1 can be also be described as a wearable device with a plurality of close-fitting spectroscopic sensors comprising: a finger ring; a first spectroscopic sensor at a first location on the inner circumference of the ring; and a second spectroscopic sensor at a second location on the inner circumference of the ring, wherein the spectroscopic sensors record biometric data concerning the person's body tissue. In an example, the spectroscopic sensors can be distributed so as to collectively span the entire inner circumference of the ring. In an example, the spectroscopic sensors can be distributed so as to collectively span between 40% and 70% of the inner circumference of the ring.

In an example, there can be a plurality of spectroscopic sensors on the inner circumference of a ring. In an example, spectroscopic sensors can be evenly distributed (e.g. equally distanced) around the inner circumference of a ring. In an example, there can be six or eight spectroscopic sensors on the inner circumference of a ring. In an example, there can be a plurality of sets of spectroscopic sensors on the inner circumference of a ring. In an example, each set can comprise light emitters which emit light with at least three different wavelengths and/or colors selected from the group consisting of: near-infrared light emitter; infra light emitter; red light emitter; and green light emitter. In an example, sets of spectroscopic sensors can be evenly distributed (e.g. equally distanced) around the inner circumference of a ring. In an example, there can be six or eight sets of spectroscopic sensors on the inner circumference of a ring.

The wearable device shown in FIG. 1 includes: a ring or band 101, an enclosure 102, and spectroscopic sensors 103, 104, 105, 106, 107, and 108. In an example, this device can further comprise one or more components selected from the group consisting of: a data processor; a battery and/or energy harvesting unit; a display screen; a data transmitter; and a data receiver. Relevant variations discussed elsewhere in this disclosure or in priority-linked disclosures can also apply to this example.

Figure 2:
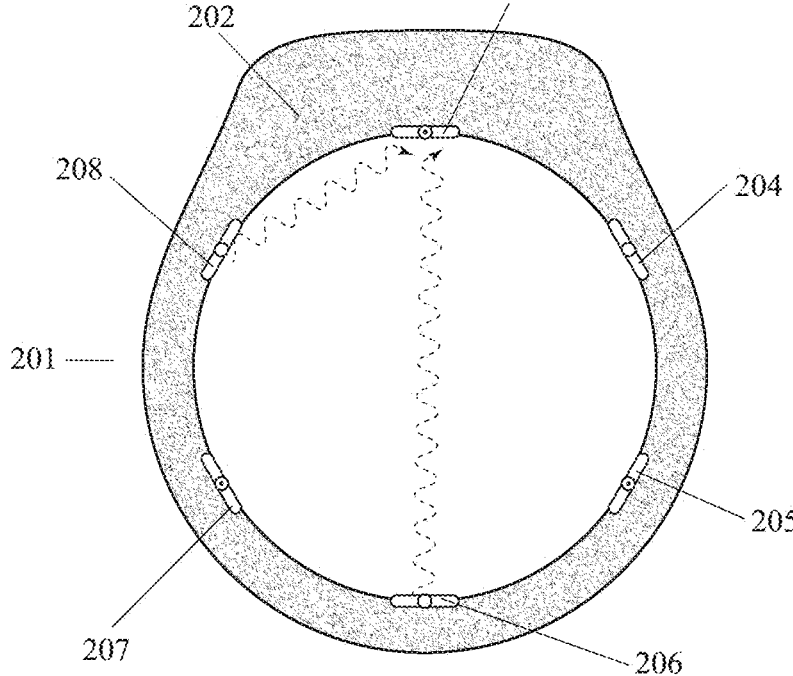
FIG. 2 shows a ring or band wherein different spectroscopic sensors project light into body tissue at different angles.

FIG. 2 shows another example of a wearable device with a plurality of close-fitting biometric sensors. This figure shows the device from a side perspective as it would appear encircling a lateral cross-section of a portion of a person's body such as a wrist or finger. The example shown in FIG. 2 is like the one shown in FIG. 1, except that different spectroscopic sensors direct light energy into body tissue at different angles.

The example shown in FIG. 2 can be described as a wearable device with a plurality of close-fitting biometric sensors comprising: an attachment member (such as a band or ring) which spans the circumference of a portion of a person's body; an enclosure which is part of the attachment member; a first spectroscopic sensor which is configured to project a beam of light into body tissue at a first angle; and a second spectroscopic sensor which is configured to project a beam of light into body tissue at a second angle, wherein the first angle differs from the second angle by at least 10 degrees.

In an example, an attachment member or band can be a finger ring. In an example, a biometric sensor can be a spectroscopic sensor which further comprises a light emitter and a light receiver. In this case, the example shown in FIG. 2 can be described as a wearable device with a plurality of close-fitting spectroscopic sensors comprising: a finger ring; an enclosure which is part of the ring; a first spectroscopic sensor which is configured to project a beam of light into finger tissue at a first angle; and a second spectroscopic sensor in the enclosure which is configured to project a beam of light into finger tissue at a second angle, wherein the first angle differs from the second angle by at least 10 degrees.

In an example, a wearable device with a plurality of close-fitting spectroscopic sensors can comprise: a finger ring; a first spectroscopic sensor which is configured to project a beam of light with a first wavelength and/or color into finger tissue at a first angle; and a second spectroscopic sensor which is configured to project a beam of light with a second wavelength and/or color into finger tissue at a second angle, wherein the first angle differs from the second angle by at least 10 degrees.

In an example, light emitters which emit light with different wavelengths and/or colors can be configured to emit light into body tissue at different angles. In an example, light emitters which emit light with different wavelengths and/or colors can be configured to emit light into body tissue at different angles relative to the inner circumference of the device. In an example, light emitters which emit light with different wavelengths and/or colors can be configured to emit light into body tissue at different angles relative to the surface of a person's body.

In an example, the angle at which a light emitter of a spectroscopic sensor emits light into body tissue can be a function of the location of the emitter on the inner circumference of a ring or band. In an example, the angle at which a light emitter of a spectroscopic sensor emits light into body tissue can be a function of the polar coordinate (e.g. radial location) of the emitter on the inner circumference of a ring or band. In an example, one or more light emitters on the dorsal side of a ring or band can emit light into body tissue at different angles than one or more light emitters on the ventral side of the ring or band.

The example shown in FIG. 2 includes: ring or band 201, enclosure 202, and spectroscopic sensors 203, 204, 205, 206, 207, and 208. In an example, this device can further comprise one or more components selected from the group consisting of: a data processor; a battery and/or energy harvesting unit; a display screen; a data transmitter; and a data receiver. Relevant variations discussed elsewhere in this disclosure or in priority-linked disclosures can also apply to this example.

FIG. 3 shows another example of a wearable device with close-fitting biometric sensors. This figure shows the device from a side perspective, as it would appear encircling a lateral cross-section of a portion of a person's body such as a wrist or finger. The example shown in FIG. 3 is an arcuate wearable device with a moving (e.g. rotating and/or pivoting) light-projecting spectroscopic sensor. Movement (e.g. rotation and/or pivoting) of the spectroscopic sensor changes the angle at which it projects light into a portion of a person's body. A spectroscopic sensor can scan different regions and/or depths of body tissue when the angle at which it projects light into the body is changed in an iterative and/or oscillating manner. The upper portion of FIG. 3 shows this device at a first time. The lower portion of FIG. 3 shows this device at a second time, after movement (e.g. rotation and/or pivoting) of the spectroscopic sensor has changed the angle at which it projects light into the person's body.

The example shown in FIG. 3 can be described as a wearable device with close-fitting biometric sensors comprising: an attachment member (such as a band or ring) which spans the circumference of a portion of a person's body; an enclosure which is part of the attachment member; and a rotating (e.g. rotating and/or pivoting) light-projecting spectroscopic sensor, wherein this sensor is rotated (e.g. rotated and/or pivoted) relative to the enclosure, and wherein rotation (e.g. rotation and/or pivoting) of this sensor relative to the enclosure changes the angle at which the sensor projects light into a portion of a person's body.

In an example, an attachment member can be a band or ring. In an example, a biometric sensor can be a spectroscopic sensor which further comprises a light emitter and a light receiver. In this case, the example shown in FIG. 3 can be described as a wearable device with a close-fitting spectroscopic sensor comprising: a finger ring; and a rotating (e.g. rotating and/or pivoting) light-projecting spectroscopic sensor on the ring, wherein this sensor is rotated (e.g. rotated and/or pivoted) relative to the ring, and wherein rotation (e.g. rotation and/or pivoting) of this spectroscopic sensor relative to the ring changes the angle at which the sensor projects light onto the surface of a portion of the person's finger.

This example can also be described as a wearable device with a close-fitting spectroscopic sensor comprising: a finger ring; and a rotating light-projecting spectroscopic sensor which scans the tissue of the person's finger. In an example, rotation (e.g. rotation and/or pivoting) of the light-projecting spectroscopic sensors causes the sensor to scan different depths and/or regions of body tissue as the light projection angles change. In an example, a light projection angle can be changed in an iterative and/or oscillating manner. In an example, a light projection angle can be changed in a sinusoidally-oscillating manner.

In an example, the angle at which light emitted from a spectroscopic sensor enters body tissue can be changed by direct movement (e.g. rotation and/or pivoting) of the spectroscopic sensor. In an example, the angle at which light emitted from a spectroscopic sensor enters body tissue can be changed by direct movement (e.g. rotation and/or pivoting) of the spectroscopic sensor by an electromagnetic actuator. In an example, a band or ring can comprise a plurality of actuators and a plurality of spectroscopic sensors, wherein each spectroscopic sensor can be individually moved (e.g. rotated and/or pivoted) by a different actuator. In an example, the angle at which light emitted from a spectroscopic sensor enters body tissue can be changed by movement (e.g. rotation and/or pivoting) of a movable component to which the spectroscopic sensor is attached.

In an example, the angle at which light emitted from a spectroscopic sensor enters body tissue can be changed indirectly by movement (e.g. pivoting and/or rotation) of a reflective component (e.g. a mirror) which reflects this light. In an example, a band or ring can comprise a plurality of (micro)mirrors and a plurality light emitters, wherein light beams from each light emitter are individually redirected (e.g. reflected) by a different (micro)mirror. In an example, a band or ring can include a digital micromirror array which redirects (e.g. reflects) light beams from spectroscopic sensors toward a person's body at different angles. In an example, the angle at which light emitted from a spectroscopic sensor enters body tissue can be changed indirectly by movement (e.g. pivoting and/or rotation) of a refractive component (e.g. a prism, lens, or optical filter) which refracts this light. In an example, a band or ring can comprise a plurality of (micro)prisms and a plurality light emitters, wherein light beams from each light emitter are individually redirected (e.g. refracted) by a different (micro) prism.

In an example, a wearable device such as a band or ring can have actuators and spectroscopic sensors, wherein an actuator rotates and/or pivots a spectroscopic sensor at a fixed location on the inner circumference of the device. In an example, a wearable device can comprise actuators which rotate and/or pivot light emitters at fixed locations on the inner circumference of the device. In an example, a wearable device can comprise actuators which rotate and/or pivot light receivers at fixed locations on the inner circumference of the device.

The wearable device shown in FIG. 3 includes: a band or ring 301, an enclosure 302, and a rotating (e.g. rotating and/or pivoting) light-projecting spectroscopic sensor 303. In an example, this device can further comprise one or more components selected from the group consisting of: a data processor; a battery and/or energy harvesting unit; a display screen; a data transmitter; and a data receiver. Relevant variations discussed elsewhere in this disclosure or in priority-linked disclosures can also apply to this example.

Figure 4:
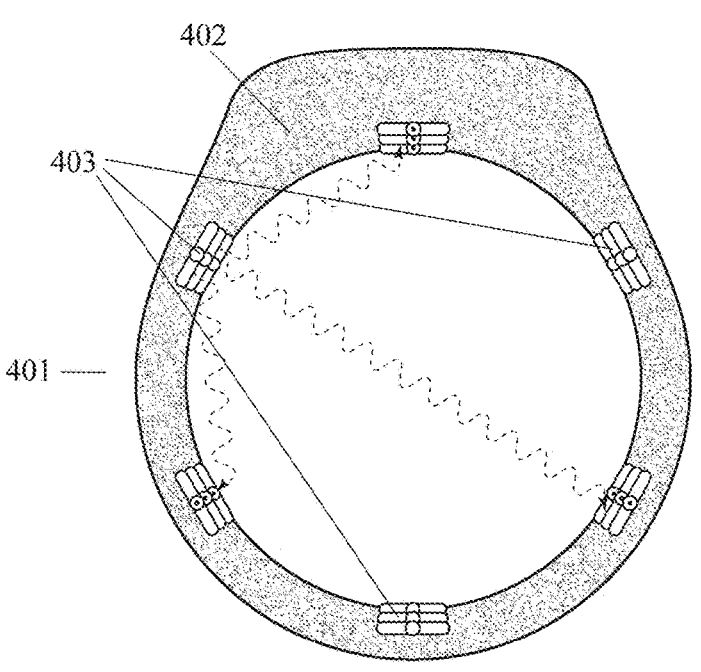
FIG. 4 shows a ring or band with a two-dimensional array of spectroscopic sensors in which sensor locations differ circumferentially and laterally.

FIG. 4 shows another example of a wearable device with a plurality of close-fitting biometric sensors. This figure shows the device from a non-perpendicular lateral perspective, as it would appear encircling a lateral cross-section of a portion of a person's body such as a wrist or finger. The example shown in FIG. 4 is an arcuate wearable device with a two-dimensional array of spectroscopic sensors. Sensors in this two-dimensional array differ in location circumferentially (they are at different locations around the circumference of the device) and laterally (they are at different locations along axes which are perpendicular to the circumference of the device).

The example shown in FIG. 4 can be described as a wearable device with a plurality of close-fitting biometric sensors comprising: an attachment member, such as a ring or band, which is configured to span the circumference of a portion of a person's body; an enclosure which is part of the attachment member; and a two-dimensional sensor array which is part of the enclosure, wherein sensors in this two-dimensional array differ in location along a portion of the circumference of the device, and wherein sensors in this two-dimensional array differ in location along axes which are perpendicular to the circumference of the device.

In an example, an attachment member or band can be a ring. In an example, a biometric sensor can be a spectroscopic sensor which further comprises a light emitter and a light receiver. In this case, the example shown in FIG. 4 can be described as a wearable device with a plurality of close-fitting spectroscopic sensors comprising: a finger ring; an enclosure which is part of the attachment member; and a two-dimensional spectroscopic sensor array which is part of (or on) the enclosure, wherein spectroscopic sensors in this two-dimensional array differ in location along a portion of the circumference of the device, and wherein spectroscopic sensors in this two-dimensional array differ in location along axes which are perpendicular to the circumference of the device.

In an example, a two-dimensional array of sensors can comprise a circle-and-row array, wherein circles are around the inner circumference of the device and rows are across the width of the device (e.g. orthogonal to the circles). In an example, rows in this array can comprise light emitters and light receivers. In an example, rows of this array can comprise light emitters which emit light with different wavelengths and/or colors. In an example, a circle-and-row array can comprise rows with two light emitters and one light receiver. In an example, a circle-and-row array can comprise rows with three light emitters selected from the group consisting of: infrared light emitter; near-infrared light emitter; red light emitter; and green light emitter.

In an example, a row of optical components along a line which is perpendicular (e.g. orthogonal) to a circumference (e.g. circle) of a ring can comprise light emitters of different colors. In an example, a row of optical components along a line which is perpendicular (e.g. orthogonal) to a circumference (e.g. circle) of a ring can comprise a light receiver between light emitters, wherein the light emitters emit light with different wavelengths and/or colors. In an example, a row of optical components along a line which is perpendicular (e.g. orthogonal) to a circumference (e.g. circle) of a ring can comprise a light emitter between light receivers.

The example shown in FIG. 4 includes: a band or ring 401, an enclosure 403, and a two-dimensional spectroscopic sensor array 403. In an example, this device can further comprise one or more components selected from the group consisting of: a data processor; a battery and/or energy harvesting unit; a display screen; a data transmitter; and a data receiver. Relevant variations discussed elsewhere in this disclosure or in priority-linked disclosures can also apply to this example.

Figure 5:
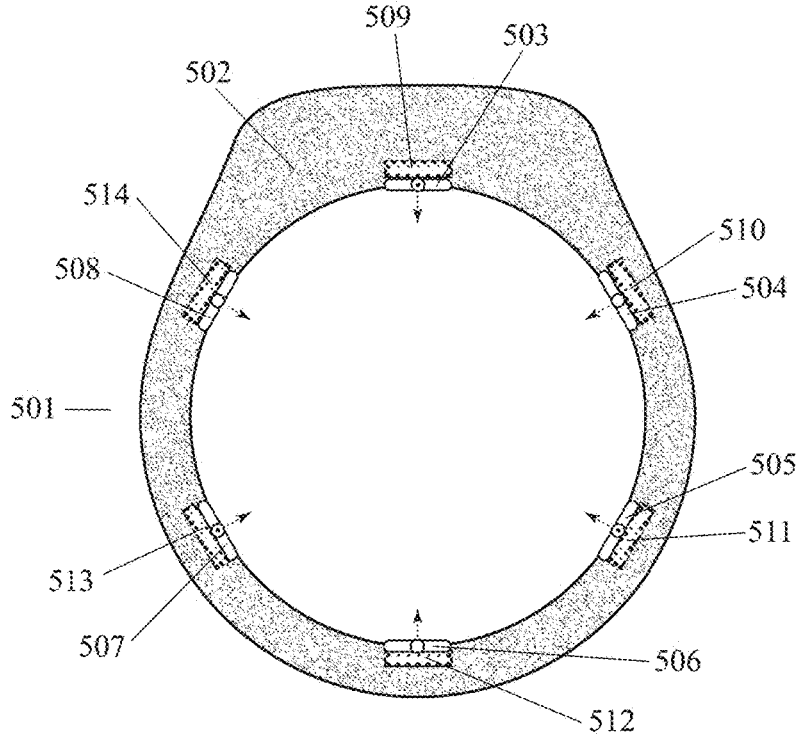
FIG. 5 shows a ring or band with a plurality of spectroscopic sensors and a plurality of actuators, wherein the actuators change the distance and/or pressure between the sensors and a person's body.

FIG. 5 shows an example of a wearable device with a plurality of close-fitting biometric sensors. This figure shows the device from a side perspective, as it would appear encircling a lateral cross-section of a portion of a person's body such as a wrist or finger. In this example, the spectroscopic sensors are on the circumference-center-facing portion of an enclosure.

The example shown in FIG. 5 is an arcuate wearable device with a plurality of spectroscopic sensors and a plurality of actuators, wherein each of these spectroscopic sensors can be individually pushed toward (or retracted away from) a person's body surface by an actuator. This can help to keep the spectroscopic sensors in close contact with a body surface, even if a portion of the device is shifted away from the body surface. In an example, the plurality of actuators enable the distances between each of these sensors and a person's body surface to be individually (and independently) adjusted.

In an example, actuators can be electromagnetic actuators. In an example, each of the spectroscopic sensors can be individually (and independently) pushed toward (or retracted away from) a person's body by an electromagnetic actuator. In an example, actuators can be pneumatic actuators. In an example, each of the spectroscopic sensors can be individually (and independently) pushed toward (or retracted away from) a person's body by a pneumatic actuator. In an example, actuators can be hydraulic actuators. In an example, each of the spectroscopic sensors can be individually (and independently) pushed toward (or retracted away from) a person's body by a hydraulic actuator.

In an example, actuators can be spring actuators. In an example, each of the spectroscopic sensors can be individually (and independently) pushed toward (or retracted away from) a person's body by a spring mechanism. In an example, actuators can be solenoids. In an example, each of the spectroscopic sensors can be individually (and independently) pushed toward (or retracted away from) a person's body by a solenoid. In an example, actuators can be pistons or telescoping mechanisms. In an example, each of the spectroscopic sensors can be individually (and independently) pushed toward (or retracted away from) a person's body by a piston or telescoping mechanism.

In an example, actuators can be electromagnets. In an example, each of the spectroscopic sensors can be individually (and independently) pushed toward (or retracted away from) a person's body by an electromagnet. In an example, actuators can be expandable chambers filled with a flowable substance. In an example, each of the spectroscopic sensors can be individually (and independently) pushed toward (or retracted away from) a person's body by an expandable chamber filled with a flowable substance.

The example shown in FIG. 5 can be described as a wearable device with a plurality of close-fitting biometric sensors comprising: an attachment member, such as a band or ring, which is configured to span the circumference of a portion of a person's body; an enclosure which is part of the attachment member; and a plurality of sensors which are part of the enclosure, wherein each sensor in this plurality of sensors can be pushed toward (or retracted away from) the body surface by an actuator to keep the sensors in close contact with the body surface.

In an example, an attachment member or band can be a ring. In an example, a biometric sensor can be a spectroscopic sensor which further comprises a light emitter and a light receiver. In this case, a wearable device with a plurality of close-fitting spectroscopic sensors can comprise: a finger ring; a plurality of actuators on the ring; and a plurality of spectroscopic sensors on the ring, wherein each spectroscopic sensor can be pushed toward (or retracted away from) a person's body surface by an actuator.

In an example, this wearable device can be described as comprising: a finger ring; and a plurality of spectroscopic sensors, wherein the distance between each spectroscopic sensor and a person's body surface is individually (and independently) adjusted by an actuator. In an example, this distance adjustment can be used to keep sensors in close contact with a person's body, even if the device shifts. In an example, distance adjustment can be used to select the sensor distances which yield the best-quality biometric information. In an example, distance adjustment can be used to set sensors at different distances for (sequentially) emitting light with different wavelengths and/or colors.

The example shown in FIG. 5 includes: a band or ring 501; an enclosure 502; a plurality of spectroscopic sensors (503, 504, 505, 506, 507, and 508); and a plurality of electromagnetic actuators, hydraulic mechanisms, pneumatic mechanisms, or spring mechanisms (509, 510, 511, 512, 513, and 514) which can push the sensors toward (or retract them away from) the center of the device through which a portion of a person's body extends. In an example, this device can further comprise one or more components selected from the group consisting of: a data processor; a battery and/or energy harvesting unit; a display screen; a data transmitter; and a data receiver.

In an example, a wearable device can comprise actuators and spectroscopic sensors, wherein the actuators can individually and independently change (e.g. adjust) the distances between the sensors and the surface of a person's body. In an example, a wearable device can comprise light emitters and actuators which can individually and independently change (e.g. adjust) the distances between the light emitters and the surface of a person's body. In an example, a wearable device can comprise light receivers and actuators which can individually and independently change (e.g. adjust) the distances between the light emitters and the surface of a person's body. Relevant variations discussed elsewhere in this disclosure or in priority-linked disclosures can also apply to this example.

Figures 6, 7:
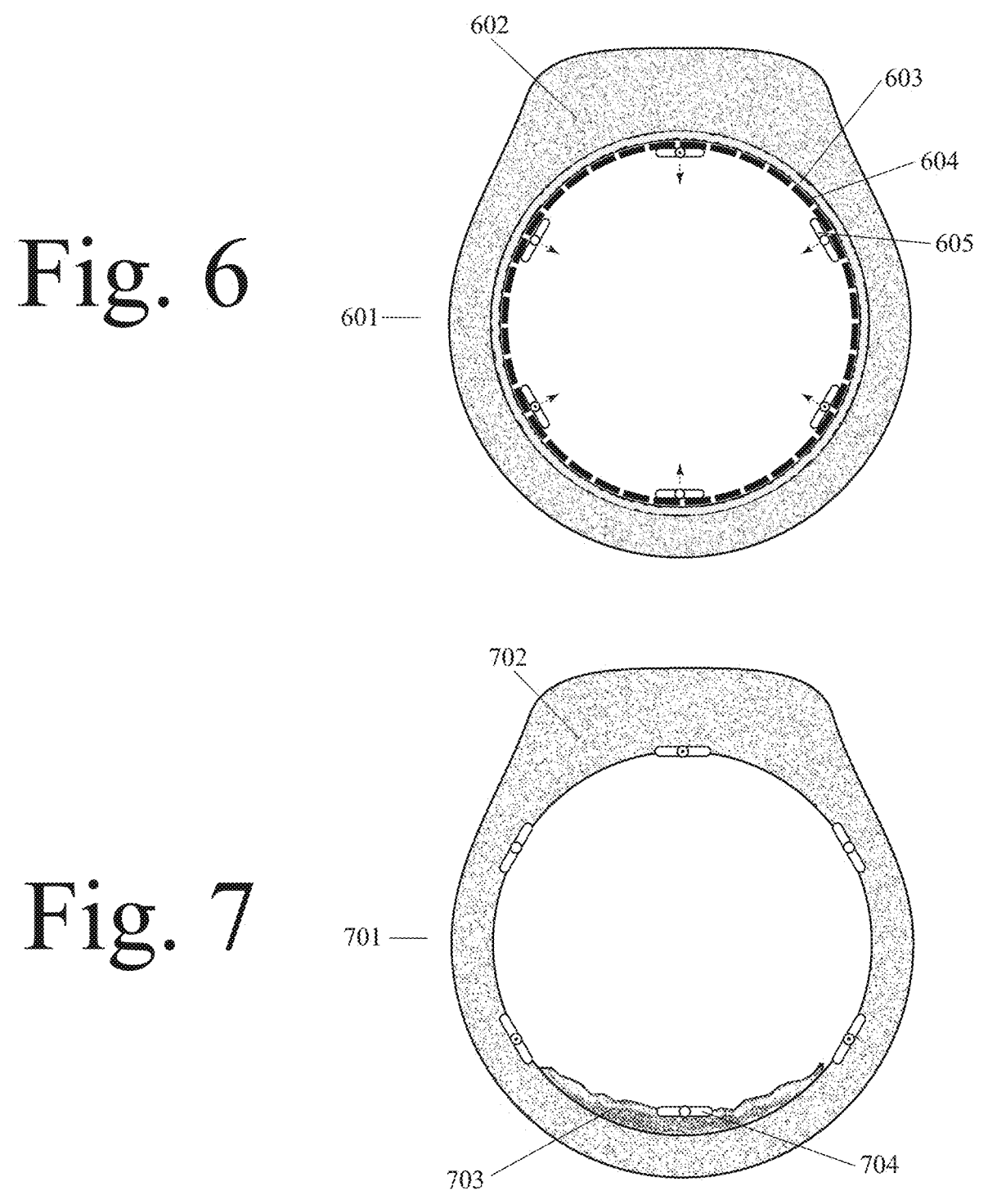

FIG. 6 shows an example of a wearable device with one or more close-fitting biometric sensors. This figure shows the device from a side perspective, as it would appear encircling a lateral cross-section of a portion of a person's body such as a wrist or finger. The example shown in FIG. 6 has multiple layers: an outer (outward-facing) circumferential layer, a middle circumferential layer, and an inner (body-facing) circumferential layer. The middle layer is sandwiched between the outer and inner layers. In an example, the layers can be nested and/or concentric. The middle circumferential layer is expandable (e.g. inflatable). The biometric sensors are located on the body-facing side of the inner layer. Accordingly, when the middle layer is expanded (e.g. inflated), it pushes the inner layer toward the portion of the person's body. This enables adjustment of the distance (and potentially pressure as well) between the biometric sensors and the person's body.

The example shown in FIG. 6 can be described as an arcuate wearable device with a biometric sensor on a circumference-center-facing portion of the device, wherein this circumference-center-facing portion is moved by an middle expandable (e.g. inflatable) portion so that the sensor remains in close contact with the surface of a portion of a person's body. In this example, the expandable (e.g. inflatable) portion is sandwiched between a rigid outward-facing portion (e.g. layer) and an inner circumference-center-facing portion (e.g. layer) of the device. Expanding (e.g. inflating) or contracting (e.g. shrinking) the expandable portion adjusts the distance between biometric sensors and the surface of the person's body.

The example shown in FIG. 6 can also be described as a wearable device with one or more close-fitting biometric sensors comprising: a band or ring which is configured to span the circumference of a portion of a person's body; a rigid outward-facing portion of the band or ring; an inner circumference-center-facing portion of the band or ring; and an expandable (e.g. inflatable) middle portion of the band or ring, wherein the expandable (e.g. inflatable) middle portion is sandwiched between the rigid outward-facing portion and the inner circumference-center-facing portion, wherein the inner circumference-center-facing portion moves relative to the rigid outward facing portion when the expandable (e.g. inflatable) middle portion is expanded or contracted; and a biometric sensor on the inner circumference-center-facing portion which is configured to record biometric data concerning the person's body tissue.

In an example, an attachment member or band can be a ring. In an example, a biometric sensor can be a spectroscopic sensor which further comprises a light emitter and a light receiver. In this case, the example shown in FIG. 6 can be described as a wearable device comprising: a finger ring; a rigid outward-facing portion of the ring; an inner circumference-center-facing portion of the ring; an expandable (e.g. inflatable) middle portion of the ring, wherein the expandable (e.g. inflatable) middle portion is sandwiched between the rigid outward-facing portion and the inner circumference-center-facing portion, and wherein the inner circumference-center-facing portion moves relative to the rigid outward-facing portion when the expandable (e.g. inflatable) middle portion is expanded or contracted; and a spectroscopic sensor on the inner circumference-centerfacing portion which is configured to record biometric data concerning the person's body tissue.

In an example, this device can also be described as a ring comprising: a rigid outer layer; a middle expandable (e.g. inflatable) layer; an inner (circumference-center-facing) layer; and one or more spectroscopic sensors on the inner layer. Expansion of the middle layer pushes the spectroscopic sensors toward the surface of a person's body. Contraction of the middle layer retracts the spectroscopic sensors away from the surface of the person's body. This enables adjustment of the distance between spectroscopic sensors and the surface of the person's body to improve the quality of biometric data obtained by the sensors. This design also enables adjustment of the fit of the ring in response to (temporary) changes in the diameter of a person's finger.

In an example, the expandable (e.g. inflatable) layer and/or the inner (circumference-center-facing) layer of this device can span the entire circumference of the device. In an example, the expandable (e.g. inflatable) layer and/or the inner (circumference-center-facing) layer of this device can span a portion of the circumference of the device. In an example, the expandable (e.g. inflatable) layer and/or the inner (circumference-center-facing) layer of this device can span between 40% and 70% of the circumference of the device.

In an example, a middle expandable portion (e.g. layer) can be expanded by being filled with a flowable substance (e.g. a liquid, gel, or gas). In an example, a ring can further comprise a pump which pumps a flowable substance (e.g. a liquid, gel, or gas) into or out of a middle expandable portion (e.g. layer). In an example, a middle expandable portion (e.g. layer) can be expanded by the application of thermal energy. In an example, a middle expandable portion (e.g. layer) can be expanded by the application of electromagnetic (e.g. electrical) energy.

The example shown in FIG. 6 includes: a band or ring 601; a rigid outward-facing portion 602 of the band or ring; an inner circumference-center-facing portion 604 of the band or ring; an expandable (e.g. inflatable) middle portion 603 of the band or ring which is sandwiched between the rigid outward-facing portion and the inner circumference-center-facing portion; and a spectroscopic sensor 605 on the inner circumference-center-facing portion of the enclosure. In an example, this device can further comprise one or more components selected from the group consisting of: a data processor; a battery and/or energy harvesting unit; a display screen; a data transmitter; and a data receiver. Relevant variations discussed elsewhere in this disclosure or in priority-linked disclosures can also apply to this example.

FIG. 7 shows an example of a wearable device with one or more close-fitting biometric sensors. This figure shows the device from a side perspective, as it would appear encircling a lateral cross-section of a portion of a person's body such as a wrist or finger. This device has an elastic member (e.g. deformable chamber) that is filled with a fluid, gel, or gas and a biometric sensor which is attached to the circumference-center-facing side of this elastic member. Having a biometric sensor attached to the circumference-center-facing wall of an elastic member (e.g. deformable chamber) can help to keep the sensor in close contact with the surface of a portion of a person's body.

The example shown in FIG. 7 can be described as a wearable device with one or more close-fitting biometric sensors comprising: an attachment member (such as a band or ring) which is configured to span the circumference of a portion of a person's body; an enclosure which is part of the attachment member; an elastic member (e.g. deformable chamber) filled with a fluid, gel, or gas which is attached to (or part of) the enclosure; and a biometric sensor which is configured to record biometric data concerning the person's body tissue, wherein this sensor is on a circumference-center-facing side of the elastic member.

In an example, an attachment member or band can be a ring. In an example, a biometric sensor can be a spectroscopic sensor which further comprises a light emitter and a light receiver. In this case, the example shown in FIG. 7 can be described as a wearable device with one or more close-fitting spectroscopic sensors comprising: a finger ring; an enclosure which is part of the ring; an elastic member filled with a fluid, gel, or gas which is attached to (or part of) the enclosure; and a spectroscopic sensor which is configured to record biometric data concerning the person's body tissue, wherein this sensor is on a circumference-center-facing wall of the elastic member.

The example shown in FIG. 7 can also be described as a wearable device with one or more close-fitting spectroscopic sensors comprising: a finger ring; an enclosure which is part of the ring; a deformable chamber filled with a fluid, gel, or gas which is attached to (or part of) the enclosure; and a spectroscopic sensor which is configured to record biometric data concerning the person's body tissue, wherein this sensor is on a circumference-center-facing side of the deformable chamber.

In an example, an expandable member and/or deformable chamber can span the entire inner circumference of a ring. In an example, an expandable member and/or deformable chamber can span between 50% and 80% of the inner circumference of a ring. In an example, an expandable member and/or deformable chamber can be filled with a fluid. In an example, an expandable member and/or deformable chamber can be filled with a gel. In an example, an expandable member and/or deformable chamber can be filled with a gas. In an example, a ring can have an expandable member and/or deformable layer around a portion of its inner circumference. In an example, there can be one or more spectroscopic sensors on the center-facing side of this expandable member and/or deformable layer.

With respect to specific components, the example shown in FIG. 7 includes: band or ring 701; enclosure 702; elastic member and/or deformable layer 703 which is filled with a fluid, gel, or gas; and biometric sensor 704 which is attached to the circumference-center-facing wall of the elastic member. In an example, this device can further comprise one or more components selected from the group consisting of: a data processor; a battery and/or energy harvesting unit; a display screen; a data transmitter; and a data receiver. Relevant variations discussed elsewhere in this disclosure or in priority-linked disclosures can also apply to this example.

Figure 8:
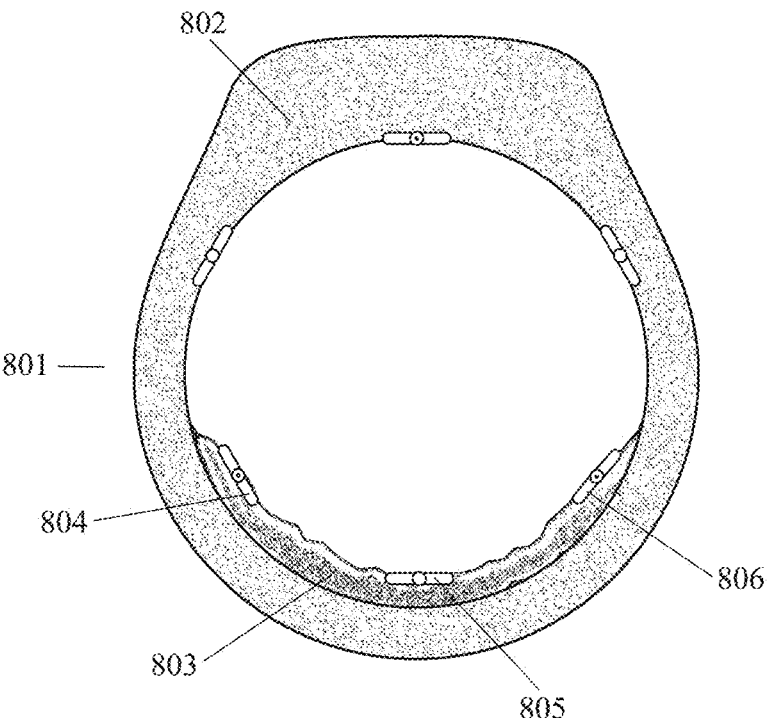
FIG. 8 shows a ring or band with spectroscopic sensors on the center-facing side of an elastic, compressible, expandable, and/or deformable member on a portion of its inner circumference.

FIG. 8 shows an example of a wearable device with one or more close-fitting biometric sensors. This figure shows the device from a side perspective, as it would appear encircling a lateral cross-section of a portion of a person's body such as a wrist or finger. The example shown in FIG. 8 is like the one shown in FIG. 7, except that in FIG. 8 there are multiple biometric sensors on the circumference-center-facing slide of an elastic member and/or deformable layer.

In an example, there can be a plurality of biometric sensors on the center-facing side of an elastic member and/or deformable layer on the interior circumference of a band or ring. In this example, there are a plurality of biometric sensors on the center-facing side of an elastic member and/or deformable layer on the interior circumference of a band or ring, wherein the elastic member and/or deformable layer is filled with a flowable substance (e.g. a liquid, gel, or gas). In this example, there are a plurality of biometric sensors on the center-facing side of an elastic member and/or deformable layer on the interior circumference of a band or ring, wherein the elastic member and/or deformable layer is made from compressible foam.

In this example, there is one continuous elastic member and/or deformable layer on the inner circumference of a wearable band or ring. In this example, the elastic member and/or deformable layer spans between 20% and 60% of the inner circumference of the band or ring. In another example, there can be a plurality of separate elastic members and/or deformable layers on the inner circumference of a wearable band or ring. In another example, there can be a plurality of separate elastic members and/or deformable layers on the inner circumference of a wearable band or ring, wherein the elastic members and/or deformable layers collectively span between 20% and 60% of the inner circumference of the band or ring. In an example, there can be a plurality of separate elastic members and/or deformable layers on the inner circumference of a wearable band or ring, wherein each elastic member and/or deformable layer spans between 5% and 15% of the inner circumference of the band or ring. In an example, there can be a separate elastic member and/or deformable layer for each spectroscopic sensor on the band or ring.

The example shown in FIG. 8 includes: a band 801; an enclosure 802; an elastic member and/or deformable layer 803 which is filled with a fluid, gel, or gas; and biometric sensors 804, 805, and 806 which are on the circumference-center-facing side of the elastic member. In an example, this device can further comprise one or more components selected from the group consisting of: a data processor; a battery and/or energy harvesting unit; a display screen; a data transmitter; and a data receiver.

In an example, an attachment member or band can be a ring. In an example, a biometric sensor can be a spectroscopic sensor which further comprises a light emitter and a light receiver. In this case, the example shown in FIG. 8 can be described as comprising: a ring; an enclosure; an elastic member and/or deformable layer; and spectroscopic sensors which are attached to the circumference-center-facing wall of the elastic member. In an example, the elastic member and/or deformable layer can be filled with a liquid, gel, or gas. In an example, the elastic member and/or deformable layer can comprise compressible foam. This example can be described as comprising: a ring; an enclosure; a deformable member; and spectroscopic sensors which are attached to the circumference-center-facing side of the deformable member. Relevant variations discussed elsewhere in this disclosure or in priority-linked disclosures can also apply to this example.

Figure 9:
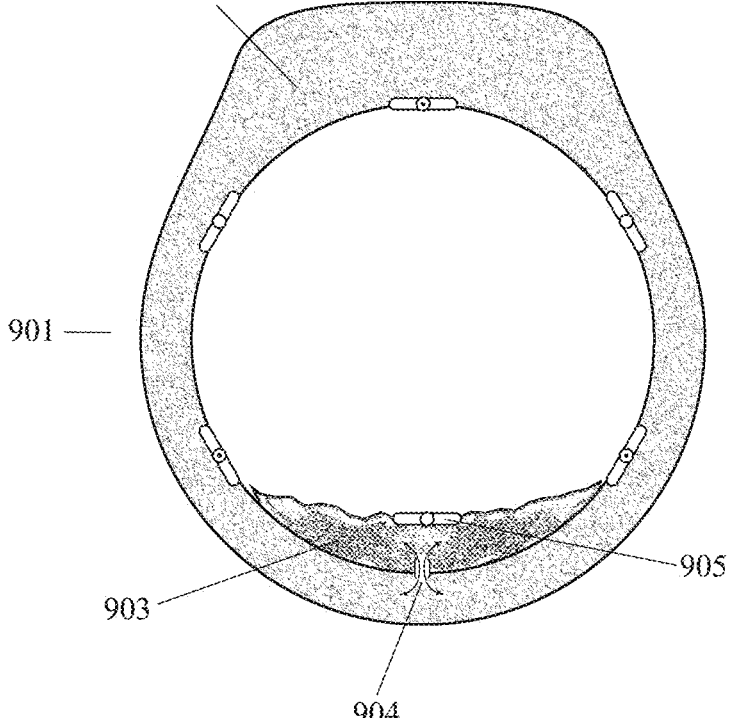
FIG. 9 shows a ring or band with a plurality of spectroscopic sensors and an expandable chamber on its inner circumference, where a flowable substance is pumped into, or out of, the chamber.

FIG. 9 shows an example of a wearable device with one or more close-fitting biometric sensors. This figure shows the device from a side perspective, as it would appear encircling a lateral cross-section of a portion of a person's body such as a wrist or finger. The example shown in FIG. 9 is like the one shown in FIG. 8, except that the device in FIG. 9 includes a micropump which can pump a flowable substance (e.g. fluid, gel, or gas) into (or out of) the elastic member (e.g. expandable chamber).

The elastic member (e.g. expandable chamber) and the associated pump enable automatic adjustment of the size and/or internal pressure of the elastic member in order to better adjust the proximity of a biometric sensor to the surface of the portion of a person's body. When the flowable substance is pumped into the elastic member, this pushes the biometric sensor toward the person's body (e.g. decreasing the distance and/or increasing the pressure between the sensor and the body). When the flowable substance is pumped out from the elastic member, this retracts the biometric sensor away from the person's body (e.g. increasing the distance and/or decreasing the pressure between the sensor and the body).

With respect to specific components, the example shown in FIG. 9 includes: a ring or band 901; an enclosure 902; an elastic member (e.g. expandable chamber) 903 which is filled with a flowable substance (e.g. fluid, gel, or gas); a biometric sensor 905 which is attached to the circumference-center-facing side of the elastic member; and a pump 904 which pumps the flowable substance (e.g. fluid, gel, or gas) into (or out of) the elastic member. In an example, this device can further comprise one or more components selected from the group consisting of: a data processor; a battery and/or energy harvesting unit; a display screen; a data transmitter; and a data receiver.

In an example, a ring or band can comprise a first elastic member (e.g. expandable chamber) on the inner circumference of the ring or band and a second elastic member (e.g. expandable chamber) in the interior (e.g. hollow enclosure) of the ring or band, wherein the flowable substance is pumped (one direction or the other) between the first elastic member and the second elastic member. When the flowable substance is pumped from the second elastic member into the first elastic member, this pushes one or more biometric sensors toward the person's body. When the flowable substance is pumped from the first elastic member into the second elastic member, this retracts the one or more biometric sensors away from the person's body.

In an example, the attachment member can be a ring. In an example, the biometric sensor can be a spectroscopic sensor which further comprises a light emitter and a light receiver. In this case, the example shown in FIG. 9 can be described as comprising: a ring; an enclosure; an elastic member which is filled with a fluid, gel, or gas; a spectroscopic sensor which is on the circumference-center-facing wall of the elastic member; and a micropump which pumps fluid, gel, or gas into (or out of) the elastic member. Relevant variations discussed elsewhere in this disclosure or in priority-linked disclosures can also apply to this example.

Figure 10:
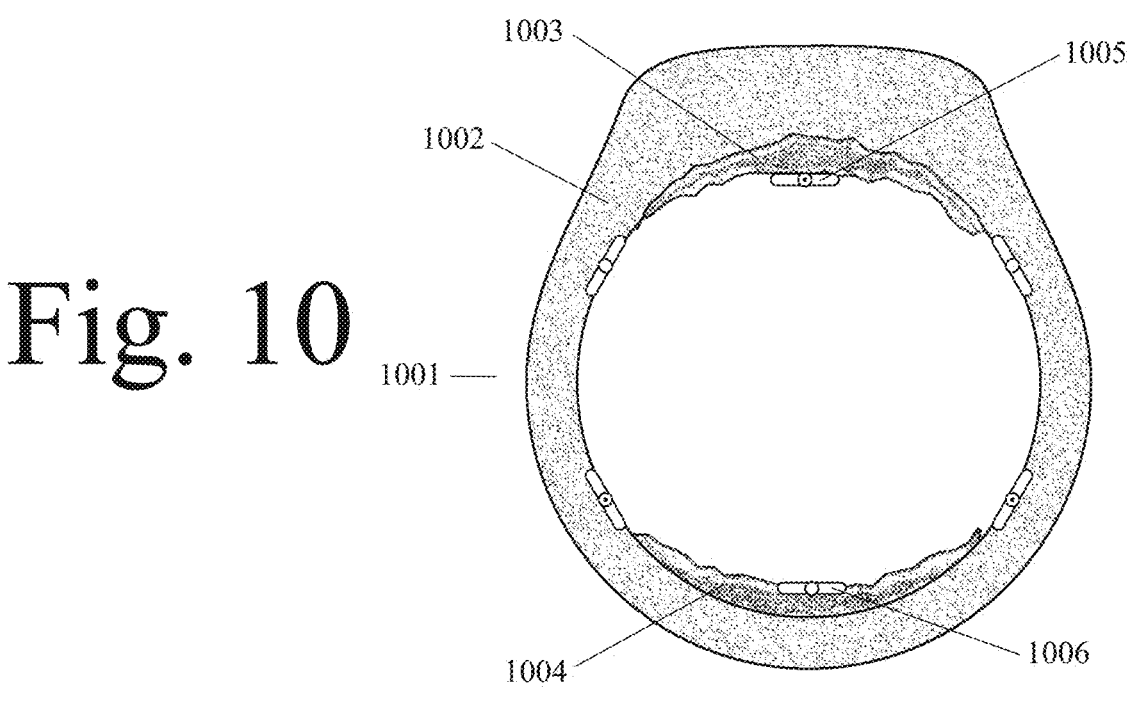
FIG. 10 shows a ring or band with a plurality of spectroscopic sensors and two elastic, compressible, expandable, and/or deformable members on different portions of its inner circumference.

FIG. 10 shows an example of a wearable device with one or more close-fitting biometric sensors. This figure shows the device from a side perspective, as it would appear encircling a lateral cross-section of a portion of a person's body such as a wrist or finger. This wearable device comprises: an attachment member such as a band or ring which is configured to span the circumference of a portion of a person's body; elastic members (e.g. deformable chambers) filled with a flowable substance (e.g. a liquid, gel, or gas), wherein these elastic members are part of (or attached to) the circumference-center-facing side of the attachment member; and biometric sensors, wherein each sensor is part of (or attached to) a circumference-center-facing side of an elastic member.

The example shown in FIG. 10 includes: a band 1001; an enclosure 1002; a first elastic member 1003 which is filled with a fluid, gel, or gas; a first biometric sensor 1005 which is attached to the circumference-center-facing wall of the first elastic member; a second elastic member 1004 which is filled with a fluid, gel, or gas; and a second biometric sensor 1006 which is attached to the circumference-center-facing wall of the second elastic member. In an example, this device can further comprise one or more components selected from the group consisting of: a data processor; a battery and/or energy harvesting unit; a display screen; a data transmitter; and a data receiver.

In an example, an attachment member or band can be a ring. In an example, a biometric sensor can be a spectroscopic sensor which further comprises a light emitter and a light receiver. In this case, the example shown in FIG. 10 can be described as comprising: a ring; an enclosure; a first elastic member which is filled with a fluid, gel, or gas; a first spectroscopic sensor on the circumference-center-facing wall of the first elastic member; a second elastic member which is filled with a fluid, gel, or gas; and a second spectroscopic sensor on the circumference-center-facing wall of the second elastic member.

In this example, first and second elastic members (e.g. deformable chambers) are diametrically opposite each other with respect to the inner circumference of the band or ring. In an example, first and second elastic members (e.g. deformable chambers) can be on opposite sides of the inner circumference of the band or ring. In an example, a first elastic member (deformable chamber) can be on the dorsal side of the inner circumference of a band or ring and a second elastic member (deformable chamber) can be on the ventral side of this circumference. In an example, a first elastic member (deformable chamber) can be on the right side of the inner circumference of a band or ring and a second elastic member (deformable chamber) can be on the left side of this circumference.

This example can also be described as comprising: a ring; an enclosure; a first deformable member; a first spectroscopic sensor which is attached to the circumference-center-facing wall of the first deformable member; a second deformable member; and a second spectroscopic sensor which is attached to the circumference-center-facing wall of the second deformable member. Relevant variations discussed elsewhere in this disclosure or in priority-linked disclosures can also apply to this example.

Figure 11:
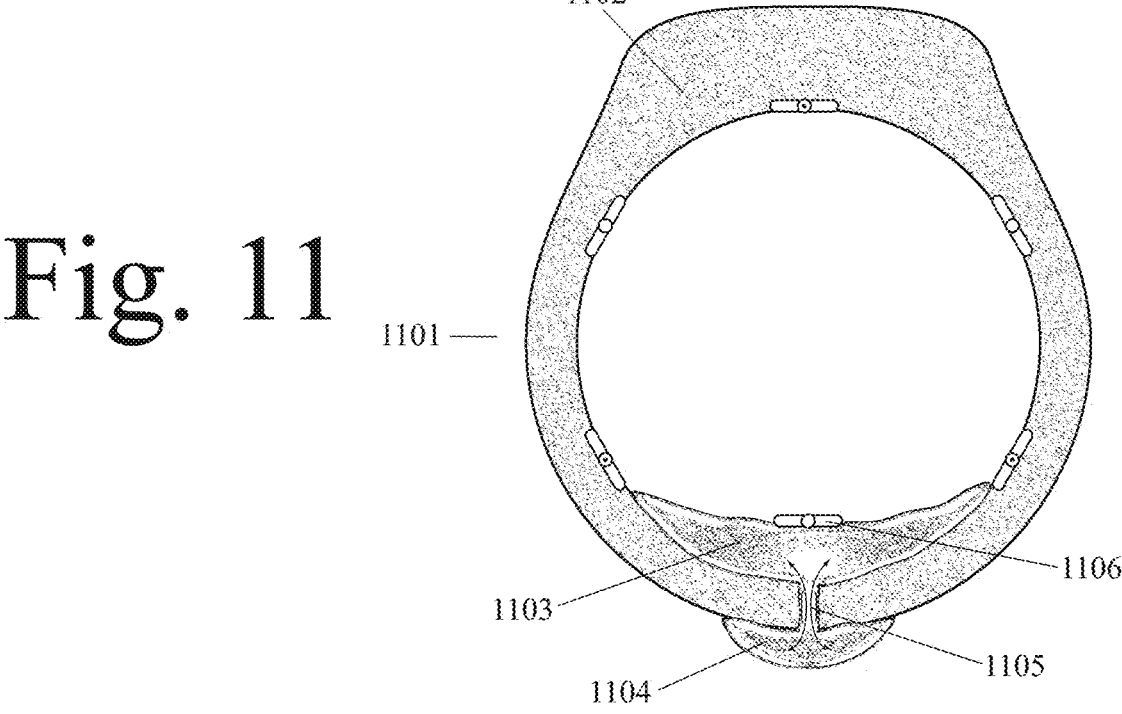
FIG. 11 shows a ring or band with a plurality of spectroscopic sensors, a first expandable chamber on its inner circumference, and a second expandable chamber on its outer circumference, where a flowable substance is pumped between the two chambers.

FIG. 11 shows an example of a wearable device with one or more close-fitting biometric sensors. This figure shows the device from a side perspective, as it would appear encircling a lateral cross-section of a portion of a person's body such as a wrist or finger. The example in FIG. 11 like the one shown in FIG. 10, except that the device in FIG. 11 also includes an outer elastic member (on the outward-facing surface of the attachment member) and a channel through which a flowable substance (e.g. fluid, gel, or gas) can flow from the inner elastic member to the outer elastic member, or vice versa. When a flowable substance flows from the outer elastic member into the inner elastic member, this pushes one or more biometric sensors toward the person's body. When the flowable substance flows from the inner elastic member into the outer elastic member, this retracts the one or more biometric sensors away from the person's body.

In an example, the ring or band can include a pump which pumps flowable substance from an outer elastic member through a channel into an inner elastic member, or vice versa. In an example, flow of a flowable substance from an outer elastic member through a channel into an inner elastic member, or vice versa, can be done automatically by a pump, thereby adjusting the fit of the ring or band and/or changing the distance (and/or pressure) between biometric sensors and the person's body. In an example, flow of a flowable substance from an outer elastic member through a channel into an inner elastic member, or vice versa, can be done manually by the person wearing the device. In an example, flow of a flowable substance from an outer elastic member through a channel into an inner elastic member, or vice versa, can be done manually by the person wearing the device, thereby adjusting the fit of the ring or band and/or changing the distance (and/or pressure) between biometric sensors and the person's body.

The example shown in FIG. 11 includes: a ring or band 1101; an enclosure 1102; one or more outward-facing elastic members 1104 which are filled with a flowable substance (e.g. fluid, gel, or gas); one or more circumference-center-facing elastic members 1103 which are filled with the flowable substance; one or more channels 1105 through which the flowable substance can flow from an outward-facing elastic member to a circumference-center-facing elastic member, or vice versa; and one or more biometric sensors 1106 on a circumference-center-facing side of a circumference-center-facing elastic member. In an example, this device can further comprise one or more components selected from the group consisting of: a data processor; a battery and/or energy harvesting unit; a display screen; a data transmitter; and a data receiver.

In an example, the attachment member can be a ring. In an example, the biometric sensor can be a spectroscopic sensor which further comprises a light emitter and a light receiver. In this case, the example shown in FIG. 11 can be described as comprising: a ring; an enclosure; one or more outward-facing elastic members which are filled with a fluid, gel, or gas; one or more circumference-center-facing elastic members which are filled with the fluid, gel, or gas; one or more channels through which the fluid, gel, or gas can flow from an outward-facing elastic member to a circumference-center-facing elastic member, or vice versa; and one or more spectroscopic sensors on a circumference-center-facing wall of a circumference-center-facing elastic member. Relevant variations discussed elsewhere in this disclosure or in priority-linked disclosures can also apply to this example.

FIG. 12 shows another example of a wearable device with one or more close-fitting biometric sensors. This figure shows the device from a side perspective, as it would appear encircling a lateral cross-section of a portion of a person's body such as a wrist or finger. The upper portion of FIG. 12 shows this device at a first time. The lower portion of FIG. 12 shows this device at a second time after the sensors have been moved so that their polar coordinate and/or radial locations on the inner circumference of the device have been changed. FIG. 12 can be described as a wearable device with biometric sensors which slide around the inner circumference of the device in order to adjust the positions from which the biometric sensors measure data concerning body tissue. Such moveable sensors enable a user to find the best positions around the circumference of the device from which to collect biometric data. They also enable the device to compensate to measure the same body regions if the device is unintentionally moved (e.g. shifted or rotated) relative to a portion of a person's body.

The device shown in FIG. 12 includes: a ring or band 1201; and biometric sensors 1202 and 1203 which move (e.g. slide) around a portion of the circumference of the ring or band. In an example, this device can further comprise one or more components selected from the group consisting of: a data processor; a battery and/or energy harvesting unit; a display screen; a data transmitter; and a data receiver.

In an example, this device can further comprise one or more circumferentially-sliding members to which one or more biometric sensors are attached, wherein the sensors slide around a portion of the circumference of the band when the sliding member slide around this circumference. In an example, a band or ring can further comprise a circumferential track (or channel) along which biometric sensors and/or sliding members travel. In an example, a biometric sensor can be slid along this track (or channel) to a desired radial location in the inner circumference of a band or ring and then locked into place there. In an example, a biometric sensor can be automatically slid along this track (and then locked in place) by an actuator. In an example, a biometric sensor can be manually slid along this track (and then locked in place).

In an example, an attachment member or band can be a ring. In an example, a biometric sensor can be a spectroscopic sensor which further comprises a light emitter and a light receiver. In this case, this example can be described as including: a finger ring; an enclosure; and spectroscopic sensors which slide around a portion of the inner circumference of the finger ring. In this case, a wearable device can comprise: a finger ring; a track or channel around the inner circumference of the finger ring; and one or more spectroscopic sensors which slide around the track or channel to different radial locations on the inner circumference of the finger ring. In an example, the ring can include an actuator which automatically moves the sensors along the track or channel. In another example, the sensors can be manually moved along the track or channel.

In an example, a wearable device such as a band or ring can have actuators and spectroscopic sensors, wherein an actuator moves (e.g. slides) a spectroscopic sensor (along a track or channel) around a portion of the inner circumference of the device. In an example, a wearable device can comprise actuators which move (e.g. slide) light emitters (along a track or channel) around a portion of the inner circumference of the device. In an example, a wearable device can comprise actuators which move (e.g. slide) light receivers (along a track or channel) around a portion of the inner circumference of the device. Relevant variations discussed elsewhere in this disclosure or in priority-linked disclosures can also apply to this example.

FIG. 13 shows an example of a wearable device with one or more close-fitting biometric sensors. This figure shows the device from a side perspective, as it would appear encircling a lateral cross-section of a portion of a person's body such as a wrist or finger. The upper portion of FIG. 13 shows this device at a first time when a rotating and/or pivoting ball to which a sensor is attached has a first orientation. The lower portion of FIG. 13 shows this device at a second time when the rotating and/or pivoting ball to which the sensor is attached has been moved (e.g. rotated and/or pivoted) into a second orientation.

The example shown in FIG. 13 can be described as an arcuate wearable device with a light-projecting spectroscopic sensor on a moving (e.g. rotating and/or pivoting) ball. Moving (e.g. rotating and/or pivoting) the ball changes the angle at which the spectroscopic sensor projects light onto a person's body. In an example, the ball can be rotated and/or rotated in different directions so that the range of projection beams can comprises a conic or frustal shape in three-dimensional space. In an example, the device can include an actuator which moves (e.g. rotates and/or pivots) the ball to which the sensor is attached. In an example, this actuator can be an electromagnetic actuator. In an example, this actuator can be a MEMS actuator.

The example shown in FIG. 13 is a wearable device with a close-fitting spectroscopic sensor comprising: (a) an attachment member, such as a band or ring, which is configured to span the circumference of a portion of a person's body; (b) an enclosure which is part of the attachment member; (c) a moving (e.g. rotating and/or pivoting)

ball which is part of (or attached to) the enclosure; and (d) a light-projecting spectroscopic sensor which is part of (or attached to) the ball.

The example shown in FIG. 13 includes: band 1301, enclosure 1302, moving (e.g. rotating and/or pivoting) ball 1303, and spectroscopic sensor 1304 which is part of (or attached to) the ball. In an example, this device can further comprise one or more components selected from the group consisting of: a data processor; a battery and/or energy harvesting unit; a display screen; a data transmitter; and a data receiver.

In an example, a band can comprise a finger ring. In this case, this example can be described as comprising: a finger ring; a moving (e.g. rotating and/or pivoting) ball; and a spectroscopic sensor which is part of (or attached to) the rotating ball. In an example, movement (e.g. rotation or pivoting) of the ball can cause the spectroscopic sensor to scan different regions and/or depths of body tissue as the light projection angles change.

In an example, this device can be described as a wearable device with a close-fitting spectroscopic sensor comprising: a finger ring; a moving (e.g. rotating and/or pivoting) ball; and a light-projecting spectroscopic sensor on the ball, wherein movement (e.g. rotation and/or pivoting) of the ball causes the spectroscopic sensor to scan the tissue of the person's finger. In an example, rotation (e.g. rotation and/or pivoting) of the ball causes the sensor to scan different depths and/or regions of body tissue as the light projection angles change. In an example, the ball can be moved (e.g. rotated and/or pivoted) back and forth in an iterative and/or oscillating manner. In an example, the ball can be moved (e.g. rotated and/or pivoted) in a sinusoidally-oscillating manner.

In an example, a rotating and/or pivoting ball to which a spectroscopic sensor is attached can be located on the dorsal side of a wearable band or ring. In an example, a rotating and/or pivoting ball to which a spectroscopic sensor is attached can be located on the ventral side of a wearable band or ring. In an example, a band or ring can have a plurality of rotating and/or pivoting balls to which a plurality of spectroscopic sensors are attached. In an example, a plurality of rotating and/or pivoting balls can be distributed around the inner circumference of a band or finger. Relevant variations discussed elsewhere in this disclosure or in priority-linked disclosures can also apply to this example.

Figure 14:
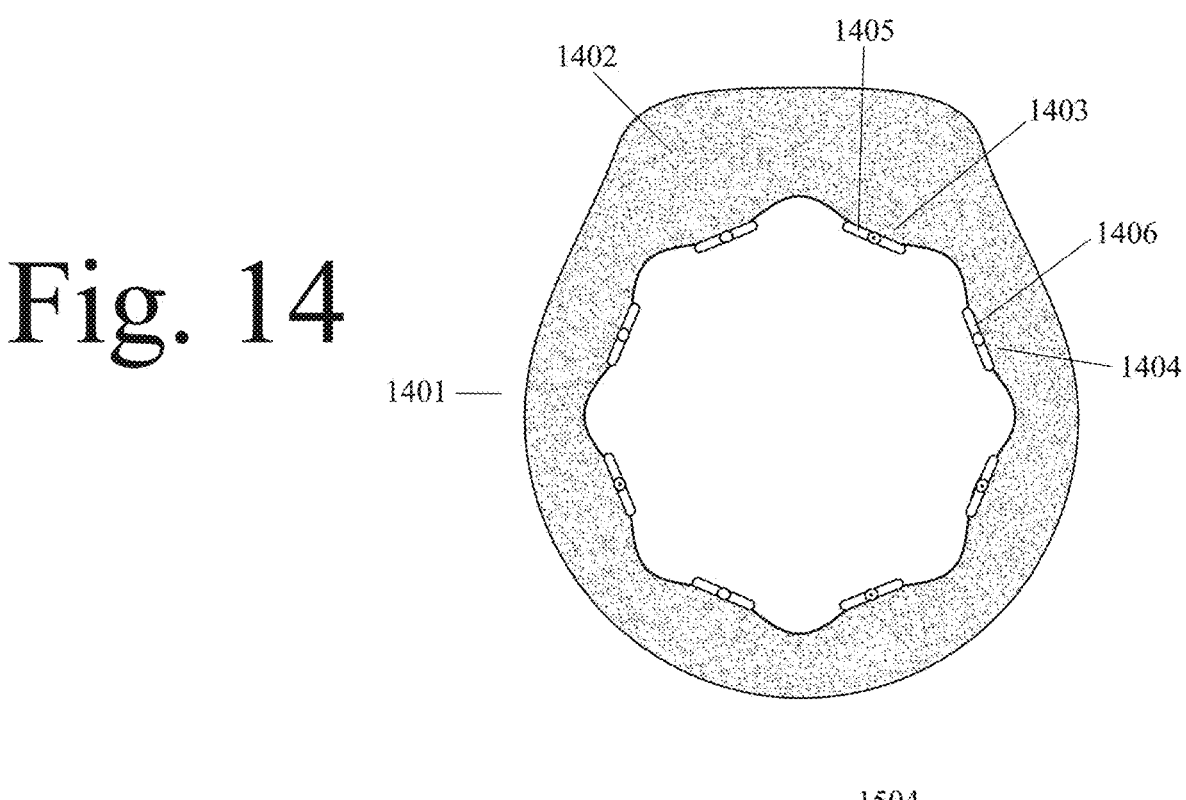
FIG. 14 shows a ring or band with a plurality of spectroscopic sensors and eight center-facing undulations, waves, and/or protrusions.

FIG. 14 shows an example of a wearable device with one or more close-fitting biometric sensors. This figure shows the device from a side perspective, as it would appear encircling a lateral cross-section of a portion of a person's body such as a wrist or finger. The example shown in FIG. 14 is a wearable device with a circumferentially-undulating band with biometric sensors on the proximal portions of undulating waves and/or protrusions. A band with such a circumferentially-undulating structure can help to keep a plurality of biometric sensors in close proximity to the surface of a portion of a person's body. In an example, the device can be a ring. In an example, a circumferentially-undulating attachment member can have a repeating wave pattern. In an example, a circumferentially-undulating attachment member can have a sinusoidal wave pattern.

The example shown in FIG. 14 can be described as a wearable device with close-fitting biometric sensors comprising: a circumferentially-undulating attachment member such as a band or ring which spans the circumference of a portion of a person's body such as a wrist or finger; and a plurality of biometric sensors which collect data concerning body tissue, wherein each biometric sensor is located at a proximal portion of an undulation, and wherein the proximal portion of an undulation is the portion of an undulating wave which is closest to the circumferential center of the device.

The device shown in FIG. 14 includes: a circumferentially-undulating band 1401, an enclosure 1402, a first biometric sensor 1405 at the proximal portion of a first wave 1403 in the circumferentially-undulating band, and a second biometric sensor 1406 at the proximal portion of a second wave 1404 in the circumferentially-undulating band. In an example, this device can further comprise one or more components selected from the group consisting of: a data processor; a battery and/or energy harvesting unit; a display screen; a data transmitter; and a data receiver.

In an example, an attachment member or band can be a ring. In an example, a biometric sensor can be a spectroscopic sensor which further comprises a light emitter and a light receiver. In this case, this example can be described as comprising: a ring with a circumferentially-undulating surface; an enclosure; a first spectroscopic sensor at the proximal portion of a first wave in the circumferentially-undulating surface; and a second spectroscopic sensor at the proximal portion of a second wave in the circumferentially-undulating surface.

In an example, this device can also be described as comprising: a ring with a plurality of inward-facing protrusions around its inner circumference; a first spectroscopic sensor on a first inward-facing protrusion; and a second spectroscopic sensor on a second inward-facing protrusion, wherein inward-facing means facing toward the center of the device through which a portion of a person's body extends. In this example, a ring has eight inward-facing protrusions. In an example, a ring can have eight inward-facing protrusions with spectroscopic sensors, wherein there are light emitters on a first set of four protrusions and light receivers on a second set of four protrusions. In an example, light emitters and light receivers can be diametrically-opposite each other on the inner circumference of the ring. Relevant variations discussed elsewhere in this disclosure or in priority-linked disclosures can also apply to this example.

Figure 15:
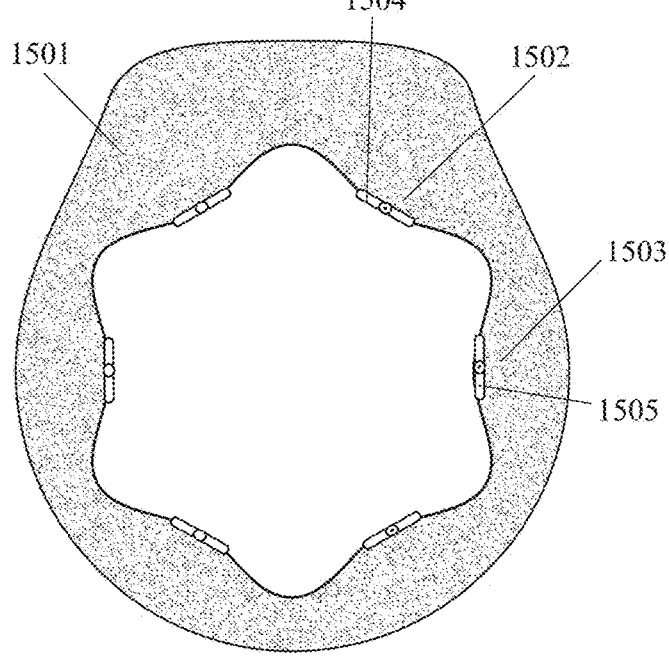
FIG. 15 shows a ring or band with a plurality of spectroscopic sensors and six center-facing undulations, waves, and/or protrusions.

FIG. 15 shows an example of a wearable device with one or more close-fitting biometric sensors. This figure shows the device from a side perspective, as it would appear encircling a lateral cross-section of a portion of a person's body such as a wrist or finger. The example shown in FIG. 15 is a circumferentially-undulating band or ring with six sinusoidal waves and/or inward-facing protrusions and biometric sensors on the proximal portions of these waves and/or protrusions.

The example shown in FIG. 15 can be described as a wearable device with one or more close-fitting biometric sensors comprising: a circumferentially-undulating attachment member with six waves and/or protrusions which spans the circumference of a portion of a person's body; and a plurality of biometric sensors which collect data concerning body tissue, wherein each biometric sensor is located at the proximal portion of an undulation and/or protrusion, and wherein the proximal portion of an undulation and/or protrusion is the portion of an undulating wave which is closest to the circumferential center of the device.

The example shown in FIG. 15 includes: circumferentially-undulating band 1501 with six waves and/or protrusions, a first biometric sensor 1504 at the proximal portion of a first wave and/or protrusion 1502 in the circumferentially-undulating band; and a second biometric sensor 1505 at the proximal portion of a second wave and/or protrusions 1503 in the circumferentially-undulating band. In an example, this device can further comprise one or more components selected from the group consisting of: a data processor; a battery and/or energy harvesting unit; a display screen; a data transmitter; and a data receiver.

In an example, an attachment member of band can be a ring. In an example, a biometric sensor can be a spectroscopic sensor which further comprises a light emitter and a light receiver. In an example, an array of spectroscopic sensors can comprise light emitters and light receivers which are diametrically-opposite each other around the inner circumference of the ring. In an example, an array of three spectroscopic sensors can comprise three light emitters and three light receivers which are diametrically-opposite each other around the inner circumference of the ring.

In an example, a light emitter or light receiver of a spectroscopic sensor can be on the most-proximal (e.g. closest to the center) surface of a wave and/or protrusion on an inner circumference of a band or ring. In an example, a wave and/or protrusion on an inner circumference of a band or ring can be deformable. In an example, a band or ring can comprise a plurality of deformable inward-facing waves and/or protrusions around the inner circumference of the band or ring. In an example, a light emitter or light receiver of a spectroscopic sensor can be within a wave and/or protrusion on an inner circumference of a band or ring, wherein the wave and/or protrusion transmits light (e.g. is transparent).

In an example, this device can be described as comprising: a circumferentially-undulating ring with six waves, a first spectroscopic sensor at the proximal portion of a first wave in the circumferentially-undulating ring; and a second spectroscopic sensor at the proximal portion of a second wave in the circumferentially-undulating ring. Relevant variations discussed elsewhere in this disclosure or in priority-linked disclosures can also apply to this example.

Figures 16, 17:
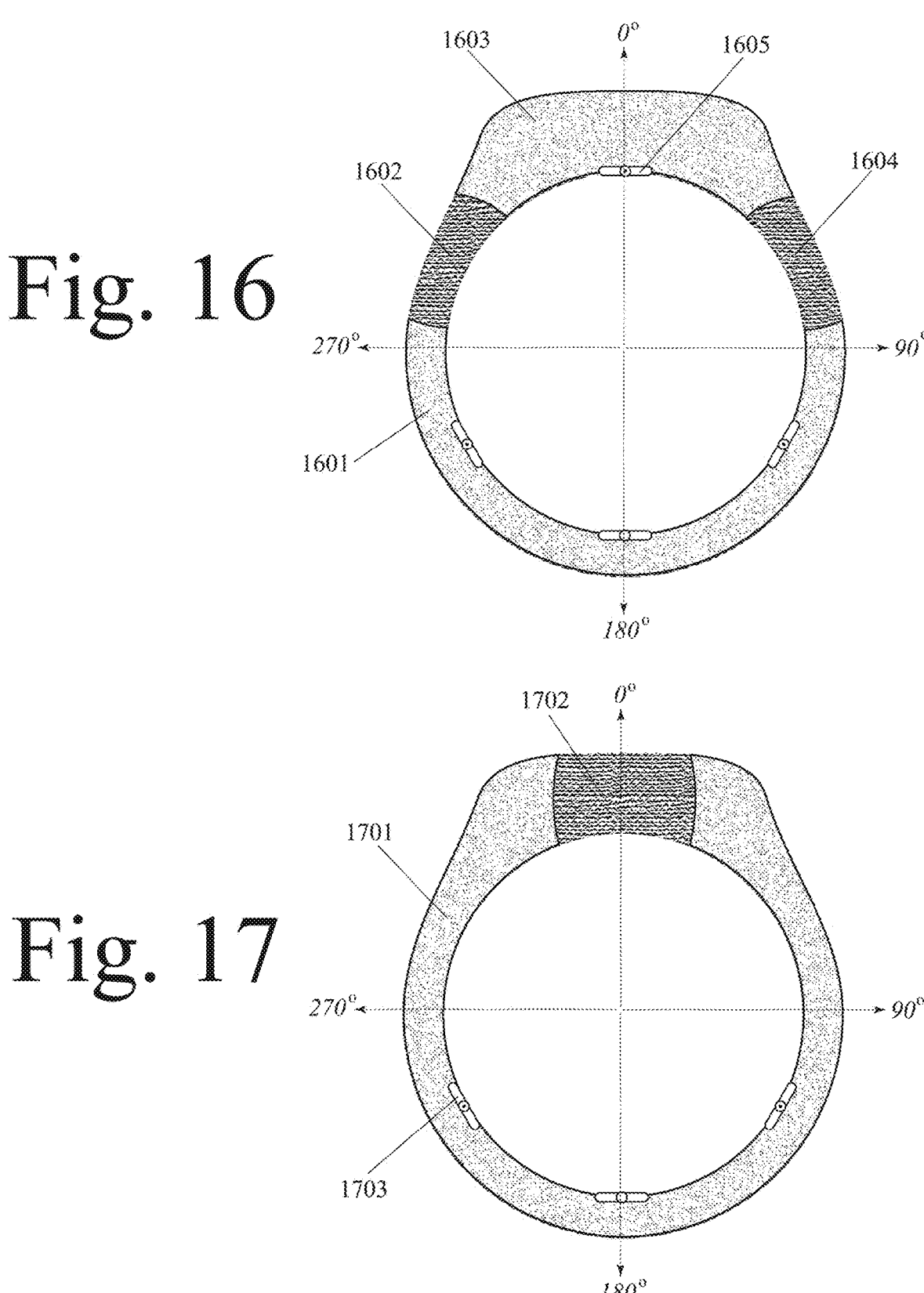
FIG. 16 shows a ring or band with a plurality of spectroscopic sensors, two rigid segments, and two flexible segments.
FIG. 17 shows a ring or band with a plurality of spectroscopic sensors, a rigid segment, and a flexible segment, wherein the flexible segment is smaller than the rigid segment.

FIG. 16 shows an example of a wearable device with one or more close-fitting biometric sensors. This figure shows the device from a side perspective, as it would appear encircling a lateral cross-section of a portion of a person's body such as a wrist or finger. The example shown in FIG. 16 is a wearable device with: one or more biometric sensors; one or more inelastic (e.g. rigid and/or inflexible) portions or segments; and one or more elastic (e.g. stretchable, articulated, and/or flexible) portions or segments. This segmented structure can: help the device to expand and contract with temporary changes in the size of a portion of a person's body (e.g. due to water weight gain or loss); and maintain good contact between the biometric sensors and the person's body during these changes. This, in turn, enables consistently accurate collection of biometric data.

The device in FIG. 16 can be described as a wearable device with one or more close-fitting biometric sensors comprising: an attachment member such as a band or ring which spans the circumference of a portion of a person's body, wherein this attachment member further comprises one or more elastic (e.g. stretchable, articulated, and/or flexible) portions or segments and one or more inelastic (e.g. rigid and/or inflexible) portions or segments; and one or more biometric sensors which collect data concerning body tissue.

In an example, a wearable device with one or more close-fitting biometric sensors can comprise: an attachment member which spans the circumference of a portion of a person's body, wherein this attachment member further comprises one or more elastic (e.g. stretchable, articulated, and/or flexible) portions or segments on the dorsal side of a portion of a person's body and one or more inelastic (e.g. rigid and/or inflexible) portions or segments on the ventral surface of the portion of the person's body; and one or more biometric sensors which collect data concerning body tissue.

The device shown in FIG. 16 is a band or ring with two elastic (e.g. stretchable, articulated, and/or flexible) portions or segments and two inelastic (e.g. rigid and/or inflexible) portions. In an example, a band or ring can comprise one elastic (e.g. stretchable, articulated, and/or flexible) portion or segment and two inelastic (e.g. rigid and/or inflexible) portions.

FIG. 16 shows polar or compass coordinates which can be used to more-precisely specify the configuration of the device. The 0-degree coordinate is located at the most-dorsal point of the circumference of the band or ring. The 180-degree coordinate is located at the most-ventral point of the circumference of the band or ring. Using these polar coordinates, a wearable device with one or more close-fitting biometric sensors can comprise: an attachment member which spans the circumference of a portion of a person's body, wherein this attachment member further comprises (a) an elastic first portion with a first level of elasticity which spans at least 35 degrees (clockwise) between the 270-degree and 0-degree positions, (b) an elastic second portion with a second level of elasticity which spans at least 35 degrees (clockwise) between the 0-degree and 90-degree positions, (c) an inelastic third portion with a third level of elasticity which spans at least 35 degrees (clockwise) between the 90-degree and 180-degree positions, and (d) an inelastic fourth portion with a fourth level of elasticity which spans at least 35 degrees (clockwise) between the 180-degree and 270-degree positions, and wherein each of the first and second elasticity levels is greater than each of the third and fourth elasticity levels; an enclosure that is configured to be worn (clockwise) between the 270-degree and 90-degree positions; and one or more biometric sensors which collect data concerning body tissue which are part of (or attached to) the enclosure.

In an example, a wearable device with one or more close-fitting biometric sensors can comprise: (a) an attachment member which is configured to span at least 60% of the circumference of a portion of a person's body wherein this attachment member further comprises an elastic first portion with a first level of elasticity which spans at least 35 degrees (clockwise) between the 270-degree and 0-degree positions; an elastic second portion with a second level of elasticity which spans at least 35 degrees (clockwise) between the 0-degree and 90-degree positions, an inelastic third portion with a third level of elasticity which spans at least 35 degrees (clockwise) between the 90-degree and 180-degree positions, an inelastic fourth portion with a fourth level of elasticity which spans at least 35 degrees (clockwise) between the 180-degree and 270-degree positions, and wherein each of the first and second elasticity levels is greater than each of the third and fourth elasticity levels; (b) an enclosure that is connected between the elastic first and second portions; and (c) one or more biometric sensors which collect data concerning body tissue which are part of (or attached to) the enclosure.

In an example, a wearable device with one or more close-fitting biometric sensors can comprise: (a) an attachment member which is configured to span at least 60% of the circumference of a portion of a person's body wherein this attachment member further comprises an elastic first portion with a first level of elasticity which spans at least 35 degrees (clockwise) between the 270-degree and 0-degree positions; an elastic second portion with a second level of elasticity which spans at least 35 degrees (clockwise) between the 0-degree and 90-degree positions, an inelastic third portion with a third level of elasticity which spans at least 35 degrees (clockwise) between the 90-degree and 180-degree positions, an inelastic fourth portion with a fourth level of elasticity which spans at least 35 degrees (clockwise) between the 180-degree and 270-degree positions, and wherein each of the first and second elasticity levels is greater than each of the third and fourth elasticity levels; (b) an enclosure that is connected between the elastic first and second portions of the attachment member; and (c) one or more biometric sensors which collect data concerning body tissue which are part of (or attached to) the enclosure.

The wearable device shown in FIG. 16 includes: a first inelastic (e.g. rigid and/or inflexible) portion or segment 1601 of an attachment member; a first elastic (e.g. flexible, stretchable, or articulated) portion or segment 1602 of an attachment member; a second inelastic portion or segment 1603 of an attachment member; a second elastic portion or segment 1604 of the attachment member; and one or more biometric sensors including 1605. In an example, this device can further comprise one or more components selected from the group consisting of: a data processor; a battery and/or energy harvesting unit; a display screen; a data transmitter; and a data receiver.

This example can also be described a wearable device comprising: a band with one or more inelastic (e.g. rigid and/or inflexible) portions or segments and one or more elastic (e.g. flexible, stretchable, or articulated) portions or segments; and one or more biometric sensors on the inelastic portions (or sections) of the band.

In an example, an attachment member or band can comprise a finger ring. In an example, biometric sensors can be spectroscopic sensors. In this case, the example shown in FIG. 16 can be described as a wearable device comprising: a finger ring with one or more inelastic (e.g. rigid and/or inflexible) portions or segments and one or more elastic (e.g. stretchable, articulated, and/or flexible) portions or segments; and one or more spectroscopic sensors on the one or more inelastic portions of the finger ring.

In an example, a finger ring can comprise an elastic (e.g. flexible, stretchable, or articulated) portion on the dorsal side of the finger ring, an inelastic (e.g. rigid and/or inflexible) portion on the ventral side of the finger ring, and one or more spectroscopic sensors on the inelastic portion. In another example, a finger ring can comprise an elastic (e.g. flexible, stretchable, or articulated) portion on the ventral side of the finger ring, an inelastic (e.g. rigid and/or inflexible) portion on the dorsal side of the finger ring, and one or more spectroscopic sensors on the inelastic portion.

In an example, a finger ring can comprise an elastic (e.g. elastic, stretchable, or articulated) portion, an inelastic (e.g. rigid and/or inflexible) portion, and one or more spectroscopic sensors, wherein the elastic portion spans between 5% and 25% of the circumference of the finger ring. In an example, a finger ring can comprise an elastic (e.g. elastic, stretchable, or articulated) portion, a rigid portion, and one or more spectroscopic sensors, wherein the elastic portion spans between 5% and 25% of the circumference of the finger ring. In an example, a finger ring can comprise a flexible (e.g. elastic, stretchable, or articulated) portion, a rigid portion, and one or more spectroscopic sensors, wherein the flexible portion spans between 5% and 25% of the circumference of the finger ring. In an example, a finger ring can comprise an articulated portion, a rigid portion, and one or more spectroscopic sensors, wherein the articulated portion spans between 5% and 25% of the circumference of the finger ring.

In an example, a finger ring can comprise a flexible (e.g. elastic, stretchable, or articulated) portion, a rigid (e.g. inflexible) portion, and one or more spectroscopic sensors, wherein the flexible portion is located between the 270-degree and 0-degree polar coordinates. In an example, a finger ring can comprise two flexible (e.g. elastic, stretchable, or articulated) portions, a rigid (e.g. inflexible) portion, and one or more spectroscopic sensors, wherein a first flexible portion is located between the 270-degree and 0-degree polar coordinates, and wherein a second flexible portion is located between the 0-degree and 90-degree polar coordinates. Relevant variations discussed elsewhere in this disclosure or in priority-linked disclosures can also apply to this example.

FIG. 17 shows an example of a wearable device with one or more close-fitting biometric sensors. This figure shows the device from a side perspective, as it would appear encircling a lateral cross-section of a portion of a person's body such as a wrist or finger. The example shown in FIG. 17 is a wearable device with one or more biometric sensors and a band with a rigid (e.g. inelastic and/or inflexible) portion and a flexible (e.g. elastic, stretchable, and/or articulated) portion. This structure can help to keep the sensors fitting closely against the portion of a person's body. This, in turn, can enable more-consistent collection of data concerning body tissue.

The device in FIG. 17 can be described as a wearable device with one or more close-fitting biometric sensors comprising: an attachment member (e.g. band) which is configured to span at least 60% of the circumference of a portion of a person's body, wherein this attachment member further comprises a flexible (e.g. elastic, stretchable, and/or articulated) portion and a rigid (e.g. inelastic and/or inflexible) portion; and one or more biometric sensors which collect data concerning body tissue.

In an example, a wearable device with one or more close-fitting biometric sensors can comprise: a band which is configured to span at least 60% of the circumference of a portion of a person's body, wherein this band (e.g. ring) further comprises a flexible (e.g. elastic, stretchable, and/or articulated) portion on the dorsal side of (the circumference of) the portion of the person's body and a rigid (e.g. inelastic and/or inflexible) portion which spans the rest of (the circumference of) the portion of the person's body; and one or more biometric sensors which collect data concerning body tissue.

As discussed elsewhere in this disclosure, an attachment and/or band can comprise a finger ring. As discussed elsewhere in this disclosure, a biometric sensor can be a spectroscopic sensor. In this case, a wearable device with one or more close-fitting biometric sensors can comprise: a finger ring which is configured to span at least 60% of the circumference of a person's finger, wherein this ring further comprises a flexible (e.g. elastic, stretchable, and/or articulated) portion on the dorsal side of (the circumference of) a person's finger and a rigid (e.g. inelastic and/or inflexible) portion which spans the rest of (the circumference of) the person's finger; and one or more spectroscopic sensors which collect data concerning body tissue.

The wearable device shown in FIG. 17 includes: a rigid (e.g. inelastic and/or inflexible) portion 1701 of a band (e.g. ring); a flexible (e.g. elastic, stretchable, and/or articulated) portion 1702 of the band (e.g. ring); and one or more biometric sensors including 1703. In an example, this device can further comprise one or more components selected from the group consisting of: a data processor; a battery and/or energy harvesting unit; a display screen; a data transmitter; and a data receiver.

In an example, a finger ring can comprise a flexible (e.g. elastic, stretchable, and/or articulated) portion on the dorsal side of the finger ring, a rigid (e.g. inelastic and/or inflexible) portion on the ventral side of the finger ring, and one or more spectroscopic sensors on the rigid portion. In another example, a finger ring can comprise a flexible (e.g. elastic, stretchable, and/or articulated) portion on the ventral side of the finger ring, a rigid (e.g. inelastic and/or inflexible) portion on the dorsal side of the finger ring, and one or more spectroscopic sensors on the rigid portion.

In an example, a finger ring can comprise an elastic (e.g. elastic, stretchable, or articulated) portion, a rigid (e.g. inelastic and/or inflexible) portion, and one or more spectroscopic sensors, wherein the flexible portion spans between 5% and 25% of the circumference of the finger ring. In an example, a finger ring can comprise an elastic (e.g. elastic, stretchable, or articulated) portion, a rigid portion, and one or more spectroscopic sensors, wherein the flexible portion spans between 5% and 25% of the circumference of the finger ring.

In an example, a finger ring can comprise a flexible (e.g. elastic, stretchable, or articulated) portion, a rigid portion, and one or more spectroscopic sensors, wherein the flexible portion spans between 5% and 25% of the circumference of the finger ring. In an example, a finger ring can comprise an articulated portion, a rigid portion, and one or more spectroscopic sensors, wherein the articulated portion spans between 5% and 25% of the circumference of the finger ring. In an example, a finger ring can comprise a flexible (e.g. elastic, stretchable, or articulated) portion, a rigid (e.g. inflexible) portion, and one or more spectroscopic sensors, wherein the flexible portion is located between the 270-degree and 0-degree polar coordinates. Relevant variations discussed elsewhere in this disclosure or in priority-linked disclosures can also apply to this example.

Figure 18:
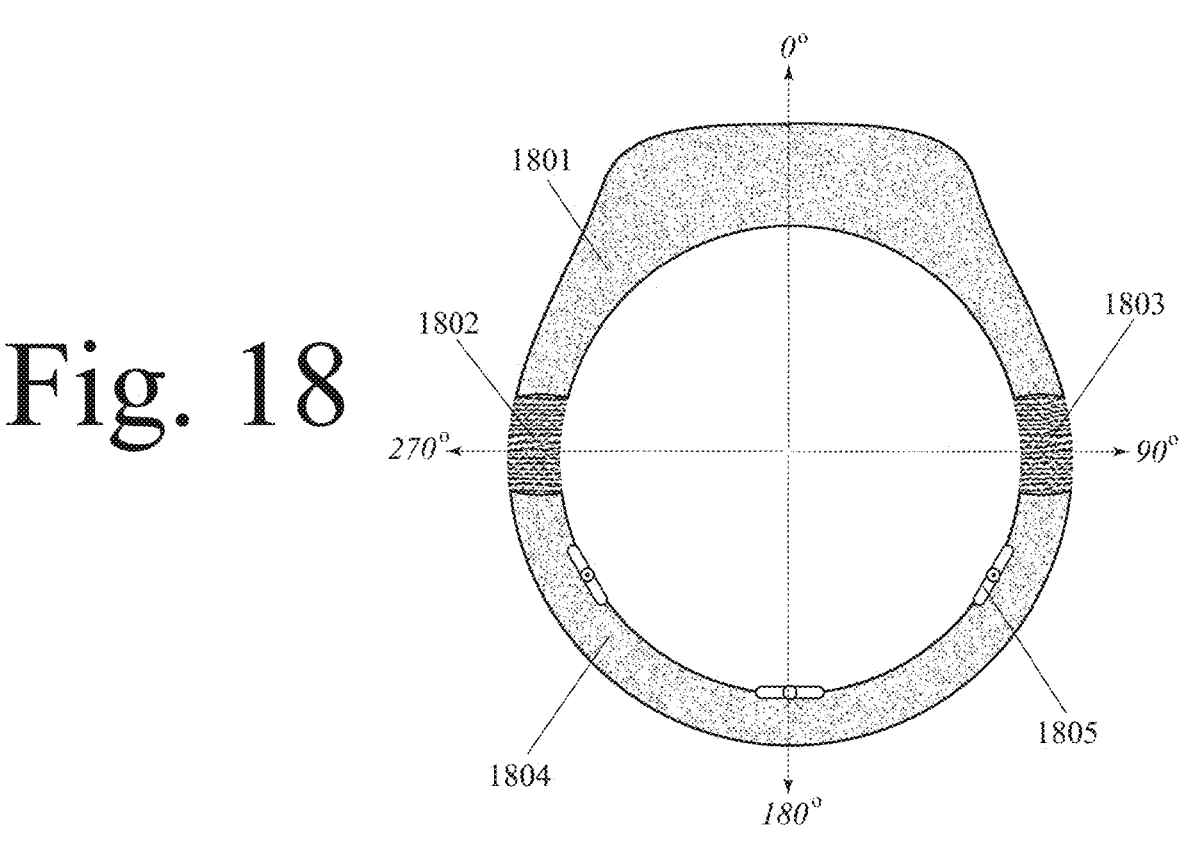
FIG. 18 shows a ring or band with a plurality of spectroscopic sensors, dorsal and ventral rigid segments, and right and left flexible segments.

FIG. 18 shows an example of a wearable device with one or more close-fitting biometric sensors. This figure shows the device from a side perspective, as it would appear encircling a lateral cross-section of a portion of a person's body such as a wrist or finger. The example shown in FIG. 18 is a wearable device with one or more biometric sensors and a band with two rigid (e.g. inelastic and/or inflexible) portions and two flexible (e.g. elastic, stretchable, and/or articulated) portions. This structure can help to keep the sensors fitting closely against the portion of a person's body. This, in turn, can enable more-consistent collection of data concerning body tissue.

The device in FIG. 18 can be described as a wearable device with one or more close-fitting biometric sensors comprising: an attachment member (e.g. band) which is configured to span at least 60% of the circumference of a portion of a person's body, wherein this attachment member further comprises two flexible (e.g. elastic, stretchable, and/or articulated) portions and two rigid (e.g. inelastic and/or inflexible) portions; and one or more biometric sensors which collect data concerning body tissue.

In an example, a wearable device with one or more close-fitting biometric sensors can comprise: a band which is configured to span at least 60% of the circumference of a portion of a person's body, wherein this band (e.g. ring) further comprises a first flexible (e.g. elastic, stretchable, and/or articulated) portion on the right side of (the circumference of) the portion of the person's body, a second flexible portion on the left side of the (circumference of) the portion of the person's body, a first rigid (e.g. inelastic and/or inflexible) portion on the dorsal side of (the circumference of) the portion of the person's body, a second rigid (e.g. inelastic and/or inflexible) portion on the ventral side of (the circumference of) the portion of the person's body; and one or more biometric sensors which collect data concerning body tissue.

As discussed elsewhere in this disclosure, an attachment member and/or band can comprise a finger ring. As discussed elsewhere in this disclosure, a biometric sensor can be a spectroscopic sensor. In this case, this example can be described as a wearable device with one or more close-fitting biometric sensors comprising: a finger ring which is configured to span at least 60% of the circumference of a person's finger, wherein this finger ring (further comprises a first flexible (e.g. elastic, stretchable, and/or articulated) portion on the right side of (the circumference of) the person's finger, a second flexible portion on the left side of the (circumference of) the person's finger, a first rigid (e.g. inelastic and/or inflexible) portion on the dorsal side of (the circumference of) the person's finger, a second rigid (e.g. inelastic and/or inflexible) portion on the ventral side of (the circumference of) the person's finger; and one or more spectroscopic sensors which collect data concerning body tissue.

The wearable device shown in FIG. 18 includes: a first rigid (e.g. inelastic and/or inflexible) portion 1804 of a ring; a second rigid portion 1801 of the ring; a first flexible (e.g. elastic, stretchable, and/or articulated) portion 1802 of the ring; a second flexible (e.g. elastic, stretchable, and/or articulated) portion 1803 of the ring; and one or more spectroscopic sensors including sensor 1805. In an example, this device can further comprise one or more components selected from the group consisting of: a data processor; a battery and/or energy harvesting unit; a display screen; a data transmitter; and a data receiver. In an example, a finger ring can comprise two elastic (e.g. elastic, stretchable, or articulated) portions, two rigid (e.g. inelastic and/or inflexible) portions, and one or more spectroscopic sensors, wherein the flexible portions collectively spans between 5% and 25% of the circumference of the finger ring. Relevant variations discussed elsewhere in this disclosure or in priority-linked disclosures can also apply to this example.

Figure 19:
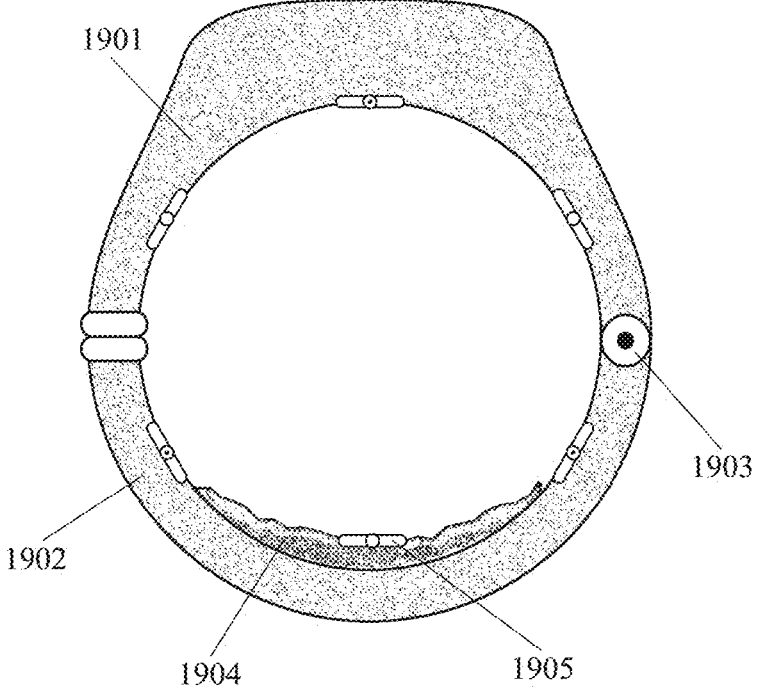
FIG. 19 shows a clam-shell-type ring or band with a plurality of spectroscopic sensors and an elastic, compressible, expandable, and/or deformable member on a portion of its inner circumference.

FIG. 19 shows another example of a wearable device with one or more close-fitting biometric sensors. This figure shows the device from a side perspective, as it would appear encircling a lateral cross-section of a portion of a person's body such as a wrist or finger. This example includes a clamshell design for a wearable band or ring with biometric sensors. The example shown in FIG. 19 includes: movable segments 1901 and 1902 of an attachment member (e.g. band); hinge 1903 which connects the movable segments; compressible (e.g. deformable) member 1904 on the interior of one of the segments; and biometric sensors including 1905. In an example, this device can further comprise one or more components selected from the group consisting of: a data processor; a battery and/or energy harvesting unit; a display screen; a data transmitter; and a data receiver.

In an example, a compressible (e.g. deformable) member can be an elastic (e.g. stretchable and/or deformable) member which is filled with a fluid, gel, or gas. In an example, a compressible (e.g. deformable) member can be a pneumatic or hydraulic chamber which is filled with a fluid, gel, or gas. In an example, a compressible (e.g. deformable) member can be a balloon. In an example, a compressible (e.g. deformable) member can be made from foam.

As discussed elsewhere in this disclosure, an attachment member and/or band can comprise a finger ring. As discussed elsewhere in this disclosure, a biometric sensor can be a spectroscopic sensor. In this case, this example can be described as a wearable device with one or more close-fitting biometric sensors comprising: movable segments of a finger ring; a hinge which connects the movable segments; compressible (e.g. deformable) foam on the interior of one of the segments; and spectroscopic sensors. Relevant variations discussed elsewhere in this disclosure or in priority-linked disclosures can also apply to this example.

Figures 20, 21:
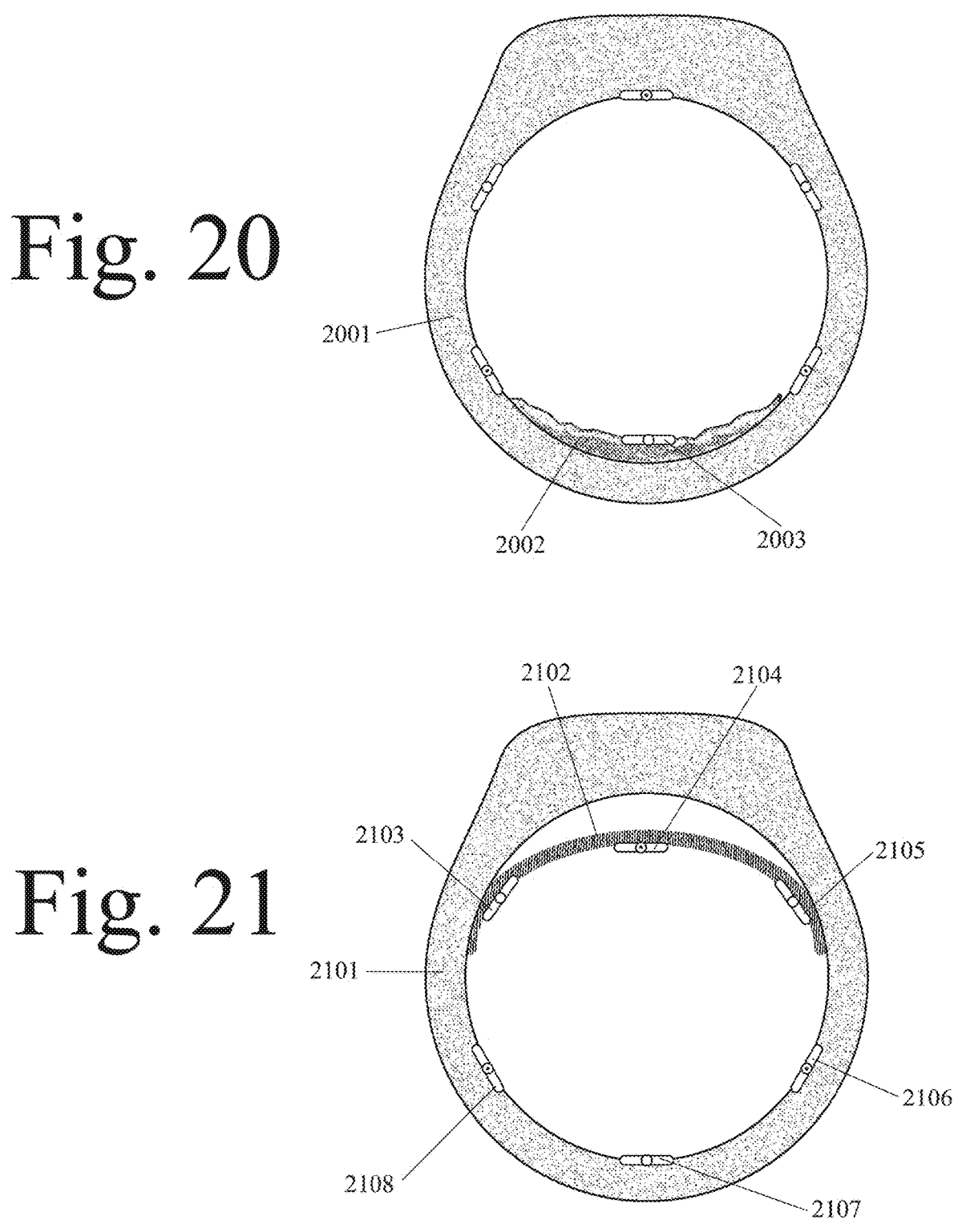

FIG. 20 shows another example of a wearable device with one or more close-fitting biometric sensors. This figure shows the device from a side perspective, as it would appear encircling a lateral cross-section of a portion of a person's body such as a wrist or finger. The example shown in FIG. 20 includes: wearable band 2001; compressible (e.g. deformable) member 2002 on the interior of the band; and biometric sensors including 2003. In an example, this device can further comprise one or more components selected from the group consisting of: a data processor; a battery and/or energy harvesting unit; a display screen; a data transmitter; and a data receiver.

In an example, a compressible (e.g. deformable) member can be an elastic (e.g. stretchable and/or deformable) member which is filled with a fluid, gel, or gas. In an example, a compressible (e.g. deformable) member can be a pneumatic or hydraulic chamber which is filled with a fluid, gel, or gas. In an example, a compressible (e.g. deformable) member can be a balloon. In an example, a compressible (e.g. deformable) member can be made from foam.

As discussed elsewhere in this disclosure, an attachment member or band can be a finger ring. As discussed elsewhere in this disclosure, a biometric sensor can be a spectroscopic sensor. In this case, this example can be described as a wearable device with one or more close-fitting biometric sensors comprising: a finger ring; compressible (e.g. deformable) foam on the inner circumference of the finger ring; and one or more spectroscopic sensors. In an example, the one or more of the spectroscopic sensors can be on the body-facing side of the compressible (e.g. deformable) foam. Relevant variations discussed elsewhere in this disclosure or in priority-linked disclosures can also apply to this example.

FIG. 21 shows an example of a wearable device with one or more close-fitting biometric sensors. This figure shows the device from a side perspective, as it would appear encircling a lateral cross-section of a portion of a person's body such as a wrist or finger. This example can be described as a wearable device with a partially-circumferential inner elastic band and biometric sensors. In an example, this device can comprise an outer inelastic (e.g. rigid and/or inflexible) band with a first elasticity level which spans the circumference of a portion of a person's body (e.g. wrist or finger) and an inner elastic (e.g. stretchable and/or deformable) band with a second elasticity level which spans only a portion of this circumference.

In an example, this device can have an outer inelastic (e.g. rigid and/or inflexible) band with a first elasticity level which spans a first percentage of the circumference of a portion of a person's body (e.g. wrist or finger) and an inner elastic (e.g. stretchable and/or deformable) band with a second elasticity level which spans a second percentage of the circumference, wherein the second percentage is less than the first percentage and the second elasticity level is greater than the first elasticity level.

In the device shown in FIG. 21, an outer inelastic band (e.g. ring) spans the entire circumference of a portion of a person's body and a semi-circular inner elastic band (interior relative to the outer inelastic band) spans only a portion (e.g. slightly less than half) of this circumference. This design can provide an overall semi-rigid structure, but also keep biometric sensors close against the body surface for consistent collection of biometric data.

The example shown in FIG. 21 can be described as a wearable device with one or more close-fitting biometric sensors comprising: an outer inelastic (e.g. rigid and/or inflexible) band which is configured to span a first percentage of a portion of a person's body and which has a first elasticity level; an inner elastic (e.g. stretchable and/or deformable) band which is configured to span a second percentage of a portion of a person's body and which has a second elasticity level, wherein the second percentage is less than the first percentage, and wherein the second elasticity level is greater than the first elasticity level; and one or more biometric sensors which are configured to collect data concerning body tissue. In an example, one or more of the biometric sensors can be part of (or attached to) the inner elastic band. In an example, one or more of the biometric sensors can be part of (or attached to) the outer inelastic band.

In an example, a wearable device with one or more close-fitting biometric sensors can comprise: an outer inelastic band with a first arcuate length and a first elasticity level; an inner elastic band with a second arcuate length and a second elasticity level, wherein the inner elastic band is located on the concave side of the outer elastic band, wherein the second length is less than the first length, and wherein the second elasticity level is greater than the first elasticity level; and one or more biometric sensors which are configured to collect data concerning body tissue. The example shown in FIG. 21 includes: an outer inelastic (e.g. rigid and/or inflexible) band 2101; an inner elastic (e.g. stretchable and/or deformable) band 2102; and biometric sensors 2103, 2104, 2105, 2106, 2107, and 2108.

The word "ring" can be substituted for the word "band" in this disclosure. Also, as discussed elsewhere in this disclosure, a biometric sensor can be a spectroscopic sensor. In this case, this example can be described as a wearable device with one or more close-fitting biometric sensors comprising: a rigid finger ring; an inner elastic (e.g. stretchable and/or deformable) band which spans a portion of the inner circumference of the finger ring; and one or more spectroscopic sensors which are configured to collect data concerning body tissue. In an example, the one or more spectroscopic sensors can be on the inner elastic band. In an example, the one or more spectroscopic sensors can be on the inner circumference of the rigid portion of the finger ring. In an example, the ends of the inner elastic band can be attached to the outer rigid finger ring.

In an example, an outer inelastic band or ring can span Y % of the circumference of a portion of a person's body (e.g. finger) and an inner elastic band can span X % of the circumference of the portion of a person's body (e.g. finger), wherein Y % is at least 20 percentage points greater than X %. In an example, Y % can be 75% and X % can be 50%. In an example, Y % can be 100% and X % can be 50%. In an example, the inner elastic band can span between 25% and 50% of the circumference of a portion of a person's body (e.g. finger). In an example, an inner elastic band can be configured to span part of the ventral surface of a portion of a person's body. In an example, an inner elastic band can be configured to span part of the dorsal surface of a portion of a person's body.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this disclosure or in priority-linked disclosures can also be applied to this example.

I claim:

1. A wearable device comprising:

a ring or band; and a plurality of spectroscopic sensors on the inner circumference of the ring or band;

wherein the spectroscopic sensors further comprise light emitters and light receivers, wherein the device further comprises a first light emitter which is configured to project a beam of light with a first wavelength or color into finger tissue at a first angle and a second light emitter which is configured to project a beam of light with a second wavelength or color into finger tissue at a second angle, and wherein the first angle differs from the second angle by at least 10 degrees.

* * * * *